US006489124B1

(12) United States Patent
Foldes et al.

(10) Patent No.: US 6,489,124 B1
(45) Date of Patent: Dec. 3, 2002

(54) HUMAN NR2A BINDING ASSAY

(75) Inventors: Robert Foldes, Willowdale; Robert Fantaske; Sally-Lin Adams, both of Toronto; Rajender Kamboj, Mississauga, all of (CA)

(73) Assignee: NPS Allelix Corp., Mississauga (CA)

( * ) Notice: Subject to any disclaimer, the term of this patent is extended or adjusted under 35 U.S.C. 154(b) by 0 days.

(21) Appl. No.: 08/217,704

(22) Filed: Mar. 25, 1994

Related U.S. Application Data

(63) Continuation-in-part of application No. 07/987,953, filed on Dec. 11, 1992, now abandoned.

(51) Int. Cl.$^7$ ................................................ G01N 33/53
(52) U.S. Cl. ......................... 435/7.2; 435/7.1; 435/7.21
(58) Field of Search ................ 435/6, 7.1, 7.2, 435/7.21, 69.1, 252.3, 320.1; 436/507

(56) References Cited

FOREIGN PATENT DOCUMENTS

| CA | 2148599 | 5/1994 |
|---|---|---|
| WO | WO 93 23536 A | 11/1993 |
| WO | WO 94/11501 | 5/1994 |
| WO | WO 94 24284 A | 10/1994 |

OTHER PUBLICATIONS

P.N.A.S. 88:7557–7561, Sep. 1941 Puckett et al.*
Schofield et al., FEBS Letters 244(2):361–364, Feb. 1989.*
Grenningloh et al., The EMBO J. 9(3):771–776, Jun. 1990.*
McNamara et al., J. of Neuroscience 12(7):2555–2562, Jul. 1992.*
Blackstone et al., Annals of Neurology 31(6):680–682, Jun. 1992.*
Hess et al. "Cloning, Functional Expression, and Pharmacological Characterization of Human NMDAR1 . . . " Biophysical Journal, vol. 66, p. 435, Mar. 6, 1994.
Karp et al. "Molecular Cloning and Chromosomal Localization of the Key Subunit of the Human N–Methyl . . . " The Journal of Biological Chemistry, vol. 268, No. 5, pp. 3728–3733, 1993.
Kutsuwada et al. "Molecular Diversity of the NMDA Receptor Channel" Nature, vol. 358, pp. 36–41, 1992.
Sugihara et al. "Structures and Properties of Seven Isoforms of the NMDA Receptor Generated by Alternative . . . " Biochemical and Biophysical Research Communications, vol. 185, No. 3, pp. 826–832, 1992.
Foldes et al. "Human N–Methyl–D–Aspartate Receptor Modulatory Subunit hNR2A: Cloning and Sequencing of the . . . " Biochimica et Biophysica Acta, vol. 1223, pp. 155–159, 1994.
Nakanishi, S. "Molecular Diversity of Glutamate Receptors and Implications for Brain Function" Science, vol. 258, pp. 597–603, 1992.

Hess et al. "Cloning and Functional Characterization of Human Heteromeric N–Methyl–D–Aspartate Receptors" The Journal of Pharmacology and Experimental Therapeutics, vol. 278, No. 2, pp. 808–816, 1996.
Anantharam et al. FEBS Letters, 1992, 305(1):27 "Combinatorial RNA splicing alters the surface charge on the NMDA receptor".
Barnett et al. Nucl Acids Res, 1990, 18:3094 "Rapid generation of DNA fragments by PCR amplification of crude, synthetic oligonucleotides".
Burnashev Cell Physiol Biochem, 1993, 3:318 "Recombinant ionotropic glutamate receptors: functional distinctions imparted by different subunits".
Collins et al. Genomics, 1993, 17:237 "Mapping of the human NMDA receptor subunit (NMDAR1) and the proposed NMDA receptor glutamate–binding subunit (NMDARA1) to chromosomes 9q34.3 and chromosome 8, respectively".
Durand et al. Proc Natl Acad Sci, 1992, 89:9359 "Cloning of an apparent splice variant of the rat N–methyl–D–aspartate receptor NMDAR1 with altered sensitivity of polyamines and activators of protein kinase C".
Durand et al. Proc Natl Acad Sci, 1993, 90:6731 "Splice variants of the N–methyl–D–aspartate receptor NR1 identify domains involved in regulation by polyamines and protein kinase C".
Foldes et al. Gene, 1993, 131:293 "Cloning and sequence analysis of cDNAs encoding human hippocampus N–methyl–D–asparate receptor subunits:evidence for alternative RNA splicing".
Hall et al. Trends Pharmacol Sci, 1993, 14:376 "Receptor subtypes or species homologues: relevance to drug discovery".
Hollman et al. Nature, 1989, 342:643 "Cloning by functional expression of a member of the glutamate receptor family".
Hollmann et al. Neuron, 1993, 10:943 "Zinc potentiates agonist–induced currents at certain splice variants of the NMDA receptor".

(List continued on next page.)

Primary Examiner—John Ulm
(74) Attorney, Agent, or Firm—Foley & Lardner

(57) ABSTRACT

Neurotransmission by excitatory amino acids (EAAs) such as glutamate is mediated via membrane-bound surface receptors. This neurotransmission has been found to be modulated by certain modulatory proteins. DNA coding for a family of such modulatory proteins has now been isolated and the modulatory proteins have been characterized. Herein described are recombinant cell lines which produce these modulatory proteins as heterologous membrane-bound products. Also described are related aspects of the invention, which are of commercial significance, including the use of cell lines which express the modulatory proteins either homomerically, or heteromerically in a complex with an NMDA receptor, as a tool for discovery of compounds which affect the function of the modulatory proteins.

15 Claims, 38 Drawing Sheets

OTHER PUBLICATIONS

Figure 2A:
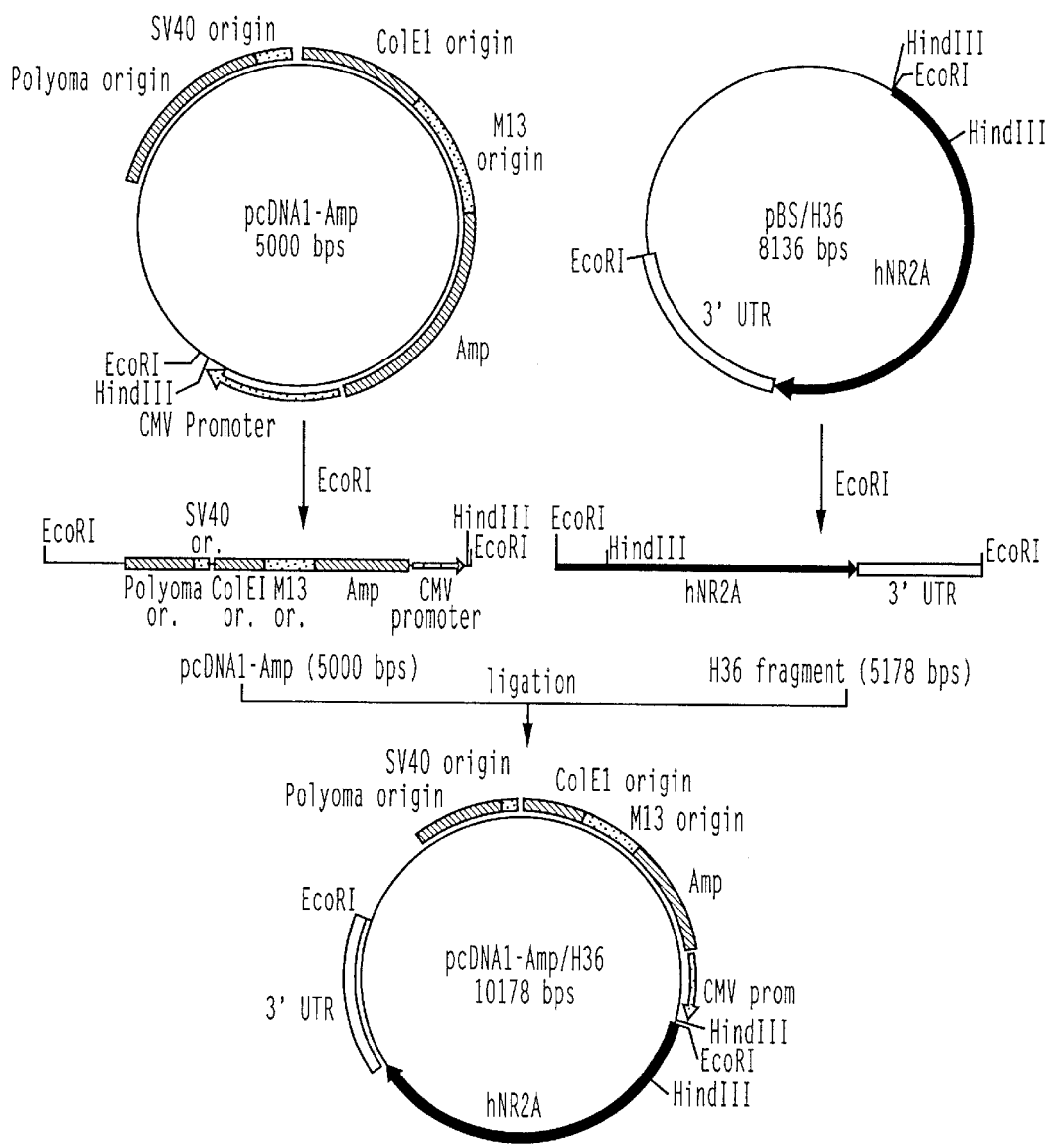

Ikeda et al. FEBS Letters, 1992, 313(1):34 "Cloning and expression of the ε4 subunit of the NMDA receptor channel".

Ishii et al. J Biol Chem, 1993, 268(4):2836 "Molecular characterization of the family of the N–methyl–D–aspartate receptor subunits".

Karp et al. J Biol Chem, 1993, 268(5):3728 "Molecular cloning and chromosomal localization of the key subunit of the human N–methyl–D–aspartate receptor".

Kopke et al. Protein Science, 1993, 2:2066 "Characterization of the NR1, NR2A, and NR2C receptor proteins".

Kusiak et al. Molecular Brain Research, 1993, 20:64 "A splice variant of the N–methyl–D–aspartate (NMDAR1) receptor".

Kutsuwada et al. Nature, 1992, 358:36 "Molecular diversity of the NMDA receptor channel".

Meguro et al. Nature, 1992, 357:70 "Functional characterization of a heteromeric NMDA receptor channel expressed from cloned cDNAs".

Mikkelsen et al. Brain Research, 1993, 632:329 "Distribution of N–methyl D–aspartate (NMDA) receptor mRNAs in the rat suprachiasmatic nucleus".

Monyer et al. Science, 1992, 256:1217 "Heteromic NMDA receptors: molecular and functional distinction of subtypes".

Mori et al. NeuroReport, 1993, 4:519 "Involvement of the carboxyl–terminal region in modulation by TPA of the NMDA receptor channel".

Moriyoshi et al. Nature, 1991, 354:31 Molecular cloning and characterization of the rat NMDA receptor.

Nakanishi et al. Proc Natl Sci, 1992, 89:8552 "Alternative splicing generates functionally distinct N–methyl–D–aspartate receptors".

Oksenberg et al. Nature 1992, 360:161 "A single amino–acid difference confers major pharmacological variation between human and rodent 5–HT1B receptors".

Planells–Cases Proc Natl Sci, 1993, 90:5057 "Molecular cloning, functional expression, and pharmacological characterization of an N–methyl–D–aspartate receptor subunit from human brain".

Pollard et al. NeuroReport, 1993, 4:411 "Transient expression of the NR2C subunit of the NMDA receptor in developing rat brain".

Pratt et al. Neuroscience, 1993, 57(2):307 "Differential regulation of N–methyl–D–aspartate receptor subunit messenger RNAs in kindling–induced epileptogenesis".

Raditsch et al. FEBS Letters, 1993, 324(1):63 "Subunit–specific block of cloned NMDA receptors by argiotoxin$_{636}$".

Sheng et al. Nature, 1994, 368:144 "Changing subunit composition of heteromeric NMDA receptors during development of rat cortex".

Sugahara et al. Biochem Biophys Res Comm, 1992, 185(3):826 "Structure and properties of seven isoforms of the NMDA receptor generated by alternative splicing".

Takano et al. Biochem Biophys Res Comm, 1993, 1997(2):922 "Chromosomal localization of the ε1, ε3 and ζ1 subunit genes of the human NMDA receptor channel".

Tingley et al. Nature, 1993, 364:70 "Regulation of NMDA receptor phosphorylation by alternative splicing of the C–terminal domain".

Ultsch et al. FEBS Letters, 1993, 324(2):171 "Glutamate receptors of Drosophila melangogaster".

Wafford et al. NeuroReport, 1993, 4:1347 "Preferential co–assmebly of recombinant NMDA receptors composed of three different subunits".

Wahlestedt et al. Nature, 1993, 363:260 "Antisense oligodeoxynucleotides to NMDA–R1 receptor channel protect cortical neurons from excitotoxicity and reduce focal ischaemic infarctions".

Watanabe et al. NeuroReport, 1992, 3:1138 "Developmental changes in distribution of NMDA receptor channel subunit mRNAs".

Watanabe et al. J Comparative Neurology, 1993, 338:377 "Distinct distributions of five N–methyl–D–aspartate receptor channel subunit mRNAs in the forebrain".

Williams Molecular Pharmacology, 1993, 44:851 "Ifenprodil discriminates subtypes of the N–methyl–D–aspartate receptor: selectivity and mechanisms at recombinant heteromeric receptors".

Williams et al. Neuron, 1993, 10:267 "Developmental switch in the expression of NMDA receptors occurs in vivo and in vitro".

Yamakura et al. NeuroReport, 1993, 4:687 "Different sensitivities of NMDA receptor channel subtypes to non–competitive antagonists".

Yamakura et al. Biochem Biophys Res Comm, 1993, 196(3):1537 "Phosphorylation of the carboxyl–terminal domain of the ζ1 subunit is not responsible for potentiation by TPA of the NMDA receptor channel".

Yamazaki et al. FEBS Letters, 1992, 300(1):39 "Cloning, expression and modulation of a mouse NMDA receptor subunit".

\* cited by examiner

FIG. 1A

```
      EcoRI
        ↓
      GAATTCCGACAGCGCGGGACAGCCAGGGGAGCGCGCTGGGGCCGCAGCATGCGGGAACCC
  1   ----------+---------+---------+---------+---------+---------+   60
      CTTAAGGCTGTCGCGCCCTGTCGGTCCCCTCGCGCGACCCCGGCGTCGTACGCCCTTGGG

GCTAAACCCGGTGGCTGCTGAGGCGGCCGAGATGCTCGTGCGCGCAGCGCGCCCCACTGC
 61   ----------+---------+---------+---------+---------+---------+  120
      CGATTTGGGCCACCGACGACTCCGCCGGCTCTACGAGCACGCGCGTCGCGCGGGGTGACG 1                           (SEQ ID NO:2)  M  G  R  V  G  Y         6
      ATCCTCGACCTTCTCGGGCTACAGGGACCGTCAGTGGCGACTATGGGCAGAGTGGGCTAT
121   ----------+---------+---------+---------+---------+---------+  180
      TAGGAGCTGGAAGAGCCCGATGTCCCTGGCAGTCACCGCTGATACCCGTCTCACCCGATA

7    W  T  L  V  L  P  A  L  L  V  W  R  G  P  A  P  S  A  A       26
      TGGACCCTGCTGGTGCTGCCGGCCCTTCTGGTCTGGCGCGGTCCGGCGCCGAGCGCGGCG
181   ----------+---------+---------+---------+---------+---------+  240
      ACCTGGGACGACCACGACGGCCGGGAAGACCAGACCGCGCCAGGCCGCGGCTCGCGCCGC

27    A  E  K  G  P  P  A  L  N  I  A  V  M  L  G  H  S  H  D  V    46
      GCGGAGAAGGGTCCCCCCGCGCTAAATATTGCGGTGATGCTGGGTCACAGCCACGACGTG
241   ----------+---------+---------+---------+---------+---------+  300
      CGCCTCTTCCCAGGGGGGCGCGATTTATAACGCCACTACGACCCAGTGTCGGTGCTGCAC

47    T  E  R  E  L  R  T  L  W  G  P  E  Q  A  A  G  L  P  L  D    66
      ACAGAGCGCGAACTTCGAACACTGTGGGGCCCCGAGCAGGCGGCGGGGCTGCCCCTGGAC
301   ----------+---------+---------+---------+---------+---------+  360
      TGTCTCGCGCTTGAAGCTTGTGACACCCCGGGGCTCGTCCGCCGCCCCGACGGGGACCTG
```

FIG. 1B

```
 67 V  N  V  V  A  L  L  M  N  R  T  D  P  K  S  L  I  T  H  V      86
    GTGAACGTGGTAGCTCTGCTGATGAACCGCACCGACCCCAAGAGCCTCATCACGCACGTG
361 ----------+----------+----------+----------+----------+----------+  420
    CACTTGCACCATCGAGACGACTACTTGGCGTGGCTGGGGTTCTCGGAGTAGTGCGTGCAC

87 C  D  L  M  S  G  A  R  I  H  G  L  V  F  G  D  D  T  D  Q     106
    TGCGACCTCATGTCCGGGGCACGCATCCACGGCCTCGTGTTTGGGGACGACACGGACCAG
421 ----------+----------+----------+----------+----------+----------+  480
    ACGCTGGAGTACAGGCCCCGTGCGTAGGTGCCGGAGCACAAACCCCTGCTGTGCCTGGTC

107 E  A  V  A  Q  M  L  D  F  I  S  S  H  T  F  V  P  I  L  G     126
    GAGGCCGTAGCCCAGATGCTGGATTTTATCTCCTCCCACACCTTCGTCCCCATCTTGGGC
481 ----------+----------+----------+----------+----------+----------+  540
    CTCCGGCATCGGGTCTACGACCTAAAATAGAGGAGGGTGTGGAAGCAGGGGTAGAACCCG

127 I  H  G  G  A  S  M  I  M  A  D  K  D  P  T  S  T  F  F  Q     146
    ATTCATGGGGGCGCATCTATGATCATGGCTGACAAGGATCCGACGTCTACCTTCTTCCAG
541 ----------+----------+----------+----------+----------+----------+  600
    TAAGTACCCCCGCGTAGATACTAGTACCGACTGTTCCTAGGCTGCAGATGGAAGAAGGTC

147 F  G  A  S  I  Q  Q  Q  A  T  V  M  L  K  I  M  Q  D  Y  D     166
    TTTGGAGCGTCCATCCAGCAGCAAGCCACGGTCATGCTGAAGATCATGCAGGATTATGAC
601 ----------+----------+----------+----------+----------+----------+  660
    AAACCTCGCAGGTAGGTCGTCGTTCGGTGCCAGTACGACTTCTAGTACGTCCTAATACTG

EcoRI
167 W  H  V  F  S  L  V  T  T  I  F  P  G  Y  R  E↓ F  I  S  F     186
    TGGCATGTCTTCTCCCTGGTGACCACTATCTTCCCTGGCTACAGGGAATTCATCAGCTTC
661 ----------+----------+----------+----------+----------+----------+  720
    ACCGTACAGAAGAGGGACCACTGGTGATAGAAGGGACCGATGTCCCTTAAGTAGTCGAAG
```

FIG. 1C

```
187  V  K  T  T  V  D  N  S  F  V  G  W  D  M  Q  N  V  I  T  L    206
     GTCAAGACCACAGTGGACAACAGCTTTGTGGGCTGGGACATGCAGAATGTGATCACACTG
721  ----------+---------+---------+---------+---------+---------+   780
     CAGTTCTGGTGTCACCTGTTGTCGAAACACCCGACCCTGTACGTCTTACACTAGTGTGAC

207  D  T  S  F  E  D  A  K  T  Q  V  Q  L  K  K  I  H  S  S  V    226
     GACACTTCCTTTGAGGATGCAAAGACACAAGTCCAGCTGAAGAAGATCCACTCTTCTGTC
781  ----------+---------+---------+---------+---------+---------+   840
     CTGTGAAGGAAACTCCTACGTTTCTGTGTTCAGGTCGACTTCTTCTAGGTGAGAAGACAG

227  I  L  L  Y  C  S  K  D  E  A  V  L  I  L  S  E  A  R  S  L    246
     ATCTTGCTCTACTGTTCCAAAGACGAGGCTGTTCTCATTCTGAGTGAGGCCCGCTCCCTT
841  ----------+---------+---------+---------+---------+---------+   900
     TAGAACGAGATGACAAGGTTTCTGCTCCGACAAGAGTAAGACTCACTCCGGGCGAGGGAA

247  G  L  T  G  Y  D  F  F  W  I  V  P  S  L  V  S  G  N  T  E    266
     GGCCTCACCGGGTATGATTTCTTCTGGATTGTCCCCAGCTTGGTCTCTGGGAACACGGAG
901  ----------+---------+---------+---------+---------+---------+   960
     CCGGAGTGGCCCATACTAAAGAAGACCTAACAGGGGTCGAACCAGAGACCCTTGTGCCTC

267  L  I  P  K  E  F  P  S  G  L  I  S  V  S  Y  D  D  W  D  Y    286
     CTCATCCCAAAAGAGTTTCCATCGGGACTCATTTCTGTCTCCTACGATGACTGGGACTAC
961  ----------+---------+---------+---------+---------+---------+  1020
     GAGTAGGGTTTTCTCAAAGGTAGCCCTGAGTAAAGACAGAGGATGCTACTGACCCTGATG

287  S  L  E  A  R  V  R  D  G  I  G  I  L  T  T  A  A  S  S  M    306
     AGCCTGGAGGCGAGAGTGAGGGACGGCATTGGCATCCTAACCACCGCTGCATCTTCTATG
1021 ----------+---------+---------+---------+---------+---------+  1080
     TCGGACCTCCGCTCTCACTCCCTGCCGTAACCGTAGGATTGGTGGCGACGTAGAAGATAC
```

FIG. 1D

```
307  L   E   F   S   Y   I   P   E   A   K   A   S   C   Y   G   Q   M   E   R    326
     CTGGAGAAGTTCTCCTACATCCCCGAGGCCAAGGCCAGCTGCTACGGGCAGATGGAGAGG
1081 ----------+---------+---------+---------+---------+---------+  1140
     GACCTCTTCAAGAGGATGTAGGGGCTCCGGTTCCGGTCGACGATGCCCGTCTACCTCTCC

327  P   E   V   P   M   H   T   L   H   P   F   M   V   N   V   T   W   D   G   K    346
     CCAGAGGTCCCGATGCACACCTTGCACCCATTTATGGTCAATGTTACATGGGATGGCAAA
1141 ----------+---------+---------+---------+---------+---------+  1200
     GGTCTCCAGGGCTACGTGTGGAACGTGGGTAAATACCAGTTACAATGTACCCTACCGTTT

347  D   L   S   F   T   E   E   G   Y   Q   V   H   P   R   L   V   V   I   V   L    366
     GACTTATCCTTCACTGAGGAAGGCTACCAGGTGCACCCCAGGCTGGTGGTGATTGTGCTG
1201 ----------+---------+---------+---------+---------+---------+  1260
     CTGAATAGGAAGTGACTCCTTCCGATGGTCCACGTGGGGTCCGACCACCACTAACACGAC

367  N   K   D   R   E   W   E   K   V   G   K   W   E   N   H   T   L   S   L   R    386
     AACAAAGACCGGGAATGGGAAAAGGTGGGCAAGTGGGAGAACCATACGCTGAGCCTGAGG
1261 ----------+---------+---------+---------+---------+---------+  1320
     TTGTTTCTGGCCCTTACCCTTTTCCACCCGTTCACCCTCTTGGTATGCGACTCGGACTCC

387  H   A   V   W   P   R   Y   K   S   F   S   D   C   E   P   D   D   N   H   L    406
     CACGCCGTGTGGCCCAGGTACAAGTCCTTCTCCGACTGTGAGCCGGATGACAACCATCTC
1321 ----------+---------+---------+---------+---------+---------+  1380
     GTGCGGCACACCGGGTCCATGTTCAGGAAGAGGCTGACACTCGGCCTACTGTTGGTAGAG

407  S   I   V   T   L   E   E   A   P   F   V   I   V   E   D   I   D   P   L   T    426
     AGCATCGTCACCCTGGAGGAGGCCCCATTCGTCATCGTGGAAGACATAGACCCCCTAACC
1381 ----------+---------+---------+---------+---------+---------+  1440
     TCGTAGCAGTGGGACCTCCTCCGGGGTAAGCAGTAGCACCTTCTGTATCTGGGGGATTGG
```

FIG. 1E

```
427 E   T   C   V   R   N   T   V   P   C   R   K   F   V   K   I   N   N   S   T  446
    GAGACGTGTGTGAGGAACACCGTGCCATGTCGGAAGTTCGTCAAAATCAACAATTCAACC
1441 ---------+---------+---------+---------+---------+---------+ 1500
    CTCTGCACACACTCCTTGTGGCACGGTACAGCCTTCAAGCAGTTTTAGTTGTTAAGTTGG
                                                         HindIII 447 N   E   G   M   N   V   K   K   C   C   K   G   F   C   I   D   I   L   K   K↓ 466
    AATGAGGGGATGAATGTGAAGAAATGCTGCAAGGGGTTCTGCATTGATATTCTGAAGAAG
1501 ---------+---------+---------+---------+---------+---------+ 1560
    TTACTCCCCTACTTACACTTCTTTACGACGTTCCCCAAGACGTAACTATAAGACTTCTTC 467 L   S   R   T   V   K   F   T   Y   D   L   Y   L   V   T   N   G   K   H   G  486
    CTTTCCAGAACTGTGAAGTTTACTTACGACCTCTATCTGGTGACCAATGGGAAGCATGGC
1561 ---------+---------+---------+---------+---------+---------+ 1620
    GAAAGGTCTTGACACTTCAAATGAATGCTGGAGATAGACCACTGGTTACCCTTCGTACCG 487 K   K   V   N   N   V   W   N   G   M   I   G   E   V   V   Y   Q   R   A   V  506
    AAGAAAGTTAACAATGTGTGGAATGGAATGATCGGTGAAGTGGTCTATCAACGGGCAGTC
1621 ---------+---------+---------+---------+---------+---------+ 1680
    TTCTTTCAATTGTTACACACCTTACCTTACTAGCCACTTCACCAGATAGTTGCCCGTCAG 507 M   A   V   G   S   L   T   I   N   E   E   R   S   E   V   V   D   F   S   V  526
    ATGGCAGTTGGCTCGCTCACCATCAATGAGGAACGTTCTGAAGTGGTGGACTTCTCTGTG
1681 ---------+---------+---------+---------+---------+---------+ 1740
    TACCGTCAACCGAGCGAGTGGTAGTTACTCCTTGCAAGACTTCACCACCTGAAGAGACAC 527 P   F   V   E   T   G   I   S   V   M   V   S   R   S   N   G   T   V   S   P  546
    CCCTTTGTGGAAACGGGAATCAGTGTCATGGTTTCAAGAAGTAATGGCACCGTCTCACCT
1741 ---------+---------+---------+---------+---------+---------+ 1800
    GGGAAACACCTTTGCCCTTAGTCACAGTACCAAAGTTCTTCATTACCGTGGCAGAGTGGA
```

FIG. 1F

```
547  S  A  F  L  E  P  F  S  A  S  V  W  V  M  M  F  V  M  L  L   566
     TCTGCTTTTCTAGAACCATTCAGCGCCTCTGTCTGGGTGATGATGTTTGTGATGCTGCTC
1801 ----------+---------+---------+---------+---------+---------+ 1860
     AGACGAAAAGATCTTGGTAAGTCGCGGAGACAGACCCACTACTACAAACACTACGACGAG

567  I  V  S  A  I  A  V  F  V  F  E  Y  F  S  P  V  G  Y  N  R   586
     ATTGTTTCTGCCATAGCTGTTTTTGTCTTTGAATACTTCAGCCCTGTTGGATACAACAGA
1861 ----------+---------+---------+---------+---------+---------+ 1920
     TAACAAAGACGGTATCGACAAAAACAGAAACTTATGAAGTCGGGACAACCTATGTTGTCT

587  N  L  A  K  G  K  A  P  H  G  P  S  F  T  I  G  K  A  I  W   606
     AACTTAGCCAAAGGGAAAGCACCCCATGGGCCTTCTTTTACAATTGGAAAAGCTATATGG
1921 ----------+---------+---------+---------+---------+---------+ 1980
     TTGAATCGGTTTCCCTTTCGTGGGGTACCCGGAAGAAAATGTTAACCTTTTCGATATACC

607  L  L  W  G  L  V  F  N  N  S  V  P  V  Q  N  P  K  G  T  T   626
     CTTCTTTGGGGCCTGGTGTTCAATAACTCCGTGCCTGTCCAGAATCCTAAAGGGACCACC
1981 ----------+---------+---------+---------+---------+---------+ 2040
     GAAGAAACCCCGGACCACAAGTTATTGAGGCACGGACAGGTCTTAGGATTTCCCTGGTGG

627  S  K  I  M  V  S  V  W  A  F  F  A  V  I  F  L  A  S  Y  T   646
     AGCAAGATCATGGTATCTGTATGGGCCTTCTTCGCTGTCATATTCCTGGCTAGCTACACA
2041 ----------+---------+---------+---------+---------+---------+ 2100
     TCGTTCTAGTACCATAGACATACCCGGAAGAAGCGACAGTATAAGGACCGATCGATGTGT

647  A  N  L  A  A  F  M  I  Q  E  E  F  V  D  Q  V  T  G  L  S   666
     GCCAATCTGGCTGCCTTCATGATCCAAGAGGAATTTGTGGACCAAGTGACCGGCCTCAGT
2101 ----------+---------+---------+---------+---------+---------+ 2160
     CGGTTAGACCGACGGAAGTACTAGGTTCTCCTTAAACACCTGGTTCACTGGCCGGAGTCA
```

FIG. 1G

```
667  D   K   K   F   Q   R   P   H   D   Y   S   P   P   F   R   F   G   T   V   P   686
     GACAAAAAGTTTCAGAGACCTCATGACTATTCCCCACCTTTTCGATTTGGGACAGTGCCT
2161 ----------+---------+---------+---------+---------+---------+ 2220
     CTGTTTTTCAAAGTCTCTGGAGTACTGATAAGGGGTGGAAAAGCTAAACCCTGTCACGGA

687  N   G   S   T   E   R   N   I   R   N   N   Y   P   Y   M   H   Q   Y   M   T   706
     AATGGAAGCACGGAGAGAAACATTCGGAATAACTATCCCTACATGCATCAGTACATGACC
2221 ----------+---------+---------+---------+---------+---------+ 2280
     TTACCTTCGTGCCTCTCTTTGTAAGCCTTATTGATAGGGATGTACGTAGTCATGTACTGG

707  K   F   N   Q   K   G   V   E   D   A   L   V   S   L   K   T   G   K   L   D   726
     AAATTTAATCAGAAAGGAGTAGAGGACGCCTTGGTCAGCCTGAAAACGGGGAAGCTGGAC
2281 ----------+---------+---------+---------+---------+---------+ 2340
     TTTAAATTAGTCTTTCCTCATCTCCTGCGGAACCAGTCGGACTTTTGCCCCTTCGACCTG

727  A   F   I   Y   D   A   A   V   L   N   Y   K   A   G   R   D   E   G   C   K   746
     GCTTTCATCTACGATGCCGCAGTCTTGAATTACAAGGCTGGGAGGGATGAAGGCTGCAAG
2341 ----------+---------+---------+---------+---------+---------+ 2400
     CGAAAGTAGATGCTACGGCGTCAGAACTTAATGTTCCGACCCTCCCTACTTCCGACGTTC

747  L   V   T   I   G   S   G   Y   I   F   A   T   T   G   Y   G   I   A   L   Q   766
     CTGGTGACCATCGGGAGTGGGTACATCTTTGCCACCACCGGTTATGGAATTGCCCTTCAG
2401 ----------+---------+---------+---------+---------+---------+ 2460
     GACCACTGGTAGCCCTCACCCATGTAGAAACGGTGGTGGCCAATACCTTAACGGGAAGTC

767  K   G   S   P   W   K   R   Q   I   D   L   A   L   L   Q   F   V   G   D   G   786
     AAAGGCTCTCCTTGGAAGAGGCAGATCGACCTGGCCTTGCTTCAGTTTGTGGGTGATGGT
2461 ----------+---------+---------+---------+---------+---------+ 2520
     TTTCCGAGAGGAACCTTCTCCGTCTAGCTGGACCGGAACGAAGTCAAACACCCACTACCA
```

FIG. 1H

```
787  E  M  E  E  L  E  T  L  W  L  T  G  I  C  H  N  E  K  N  E      806
     GAGATGGAGGAGCTGGAGACCCTGTGGCTCACTGGGATCTGCCACAACGAGAAGAACGAG
2521 ----------+----------+----------+----------+----------+----------+  2580
     CTCTACCTCCTCGACCTCTGGGACACCGAGTGACCCTAGACGGTGTTGCTCTTCTTGCTC

807  V  M  S  S  Q  L  D  I  D  N  M  A  G  V  F  Y  M  L  A  A      826
     GTGATGAGCAGCCAGCTGGACATTGACAACATGGCGGGCGTATTCTACATGCTGGCTGCC
2581 ----------+----------+----------+----------+----------+----------+  2640
     CACTACTCGTCGGTCGACCTGTAACTGTTGTACCGCCCGCATAAGATGTACGACCGACGG

827  A  M  A  L  S  L  I  T  F  I  W  E  H  L  F  Y  W  K  L  R      846
     GCCATGGCCCTTAGCCTCATCACCTTCATCTGGGAGCACCTCTTCTACTGGAAGCTGCGC
2641 ----------+----------+----------+----------+----------+----------+  2700
     CGGTACCGGGAATCGGAGTAGTGGAAGTAGACCCTCGTGGAGAAGATGACCTTCGACGCG

847  F  C  F  T  G  V  C  S  D  R  P  G  L  L  F  S  I  S  R  G      866
     TTCTGTTTCACGGGCGTGTGCTCCGACCGGCCTGGGTTGCTCTTCTCCATCAGCAGGGGC
2701 ----------+----------+----------+----------+----------+----------+  2760
     AAGACAAAGTGCCCGCACACGAGGCTGGCCGGACCCAACGAGAAGAGGTAGTCGTCCCCG

867  I  Y  S  C  I  H  G  V  H  I  E  E  K  K  K  S  P  D  F  N      886
     ATCTACAGCTGCATTCATGGAGTGCACATTGAAGAAAAGAAGAAGTCTCCAGACTTCAAT
2761 ----------+----------+----------+----------+----------+----------+  2820
     TAGATGTCGACGTAAGTACCTCACGTGTAACTTCTTTTCTTCTTCAGAGGTCTGAAGTTA

887  L  T  G  S  Q  S  N  M  L  K  L  L  R  S  A  K  N  I  S  S      906
     CTGACGGGATCCCAGAGCAACATGTTAAAACTCCTCCGGTCAGCCAAAAACATTTCCAGC
2821 ----------+----------+----------+----------+----------+----------+  2880
     GACTGCCCTAGGGTCTCGTTGTACAATTTTGAGGAGGCCAGTCGGTTTTTGTAAAGGTCG
```

FIG. 1I

```
907  M   S   N   M   N   S   S   R   M   D   S   P   K   R   A   A   D   F   I   Q   926
     ATGTCCAACATGAACTCCTCAAGAATGGACTCACCCAAAAGAGCTGCTGACTTCATCCAA
2881 ----------+---------+---------+---------+---------+---------+  2940
     TACAGGTTGTACTTGAGGAGTTCTTACCTGAGTGGGTTTTCTCGACGACTGAAGTAGGTT

927  R   G   S   L   I   M   D   M   V   S   D   K   G   N   L   M   Y   S   D   N   946
     AGAGGTTCCCTCATCATGGACATGGTTTCAGATAAGGGGAATTTGATGTACTCAGACAAC
2941 ----------+---------+---------+---------+---------+---------+  3000
     TCTCCAAGGGAGTAGTACCTGTACCAAAGTCTATTCCCCTTAAACTACATGAGTCTGTTG

947  R   S   F   Q   G   K   E   S   I   F   G   D   N   M   N   E   L   Q   T   F   966
     AGGTCCTTTCAGGGGAAAGAGAGCATTTTTGGAGACAACATGAACGAACTCCAAACATTT
3001 ----------+---------+---------+---------+---------+---------+  3060
     TCCAGGAAAGTCCCCTTTCTCTCGTAAAAACCTCTGTTGTACTTGCTTGAGGTTTGTAAA

967  V   A   N   R   Q   K   D   N   L   N   N   Y   V   F   Q   G   Q   H   P   L   986
     GTGGCCAACCGGCAGAAGGATAACCTCAATAACTATGTATTCCAGGGACAACATCCTCTT
3061 ----------+---------+---------+---------+---------+---------+  3120
     CACCGGTTGGCCGTCTTCCTATTGGAGTTATTGATACATAAGGTCCCTGTTGTAGGAGAA

987  T   L   N   E   S   N   P   N   T   V   E   V   A   V   S   T   E   S   K   A   1006
     ACTCTCAATGAGTCCAACCCTAACACGGTGGAGGTGGCCGTGAGCACAGAATCCAAAGCG
3121 ----------+---------+---------+---------+---------+---------+  3180
     TGAGAGTTACTCAGGTTGGGATTGTGCCACCTCCACCGGCACTCGTGTCTTAGGTTTCGC

1007 N   S   R   P   R   Q   L   W   K   K   S   V   D   S   I   R   Q   D   S   L   1026
     AACTCTAGACCCCGGCAGCTGTGGAAGAAATCCGTAGATTCCATACGCCAGGATTCACTA
3181 ----------+---------+---------+---------+---------+---------+  3240
     TTGAGATCTGGGGCCGTCGACACCTTCTTTAGGCATCTAAGGTATGCGGTCCTAAGTGAT
```

FIG. 1J

```
1027  S   Q   N   P   V   S   Q   R   D   E   A   T   A   E   N   R   T   H   S   L   1046
      TCCCAGAATCCAGTCTCCCAGAGGGATGAGGCAACAGCAGAGAATAGGACCCACTCCCTA
3241  ----------+---------+---------+---------+---------+---------+  3300
      AGGGTCTTAGGTCAGAGGGTCTCCCTACTCCGTTGTCGTCTCTTATCCTGGGTGAGGGAT

1047  K   S   P   R   Y   L   P   E   E   M   A   H   S   D   I   S   E   T   S   N   1066
      AAGAGCCCTAGGTATCTTCCAGAAGAGATGGCCCACTCTGACATTTCAGAAACGTCAAAT
3301  ----------+---------+---------+---------+---------+---------+  3360
      TTCTCGGGATCCATAGAAGGTCTTCTCTACCGGGTGAGACTGTAAAGTCTTTGCAGTTTA

1067  R   A   T   C   H   R   E   P   D   N   S   K   N   H   K   T   K   D   N   F   1086
      CGGGCCACGTGCCACAGGGAACCTGACAACAGTAAGAACCACAAAACCAAGGACAACTTT
3361  ----------+---------+---------+---------+---------+---------+  3420
      GCCCGGTGCACGGTGTCCCTTGGACTGTTGTCATTCTTGGTGTTTTGGTTCCTGTTGAAA

1087  K   R   S   V   A   S   K   Y   P   K   D   C   S   E   V   E   R   T   Y   L   1106
      AAAAGGTCAGTGGCCTCCAAATACCCCAAGGACTGTAGTGAGGTCGAGCGCACCTACCTG
3421  ----------+---------+---------+---------+---------+---------+  3480
      TTTTCCAGTCACCGGAGGTTTATGGGGTTCCTGACATCACTCCAGCTCGCGTGGATGGAC

1107  K   T   K   S   S   S   P   R   D   K   I   Y   T   I   D   G   E   K   E   P   1126
      AAAACCAAATCAAGCTCCCCTAGAGACAAGATCTACACTATAGATGGTGAGAAGGAGCCT
3481  ----------+---------+---------+---------+---------+---------+  3540
      TTTTGGTTTAGTTCGAGGGGATCTCTGTTCTAGATGTGATATCTACCACTCTTCCTCGGA

1127  G   F   H   L   D   P   P   Q   F   V   E   N   V   T   L   P   E   N   V   D   1146
      GGTTTCCACTTAGATCCACCCCAGTTTGTTGAAAATGTGACCCTGCCCGAGAACGTGGAC
3541  ----------+---------+---------+---------+---------+---------+  3600
      CCAAAGGTGAATCTAGGTGGGGTCAAACAACTTTTACACTGGGACGGGCTCTTGCACCTG
```

FIG. 1K

```
1147  F  P  D  P  Y  Q  D  P  S  E  N  F  R  K  G  D  S  T  L  P   1166
      TTCCCGGACCCCTACCAGGATCCCAGTGAAAACTTCCGCAAGGGGGACTCCACGCTGCCA
3601  ----------+----------+----------+----------+----------+----------+  3660
      AAGGGCCTGGGGATGGTCCTAGGGTCACTTTTGAAGGCGTTCCCCCTGAGGTGCGACGGT

1167  M  N  R  N  P  L  H  N  E  E  G  L  S  N  N  D  Q  Y  K  L   1186
      ATGAACCGGAACCCCTTGCATAATGAAGAGGGGCTTTCCAACAACGACCAGTATAAACTC
3661  ----------+----------+----------+----------+----------+----------+  3720
      TACTTGGCCTTGGGGAACGTATTACTTCTCCCCGAAAGGTTGTTGCTGGTCATATTTGAG

1187  Y  S  K  H  F  T  L  K  D  K  G  S  P  H  S  E  T  S  E  R   1206
      TACTCCAAGCACTTCACCTTGAAAGACAAGGGTTCCCCGCACAGTGAGACCAGCGAGCGA
3721  ----------+----------+----------+----------+----------+----------+  3780
      ATGAGGTTCGTGAAGTGGAACTTTCTGTTCCCAAGGGGCGTGTCACTCTGGTCGCTCGCT

1207  Y  R  Q  N  S  T  H  C  R  S  C  L  S  N  M  P  T  Y  S  G   1226
      TACCGGCAGAACTCCACGCACTGCAGAAGCTGCCTTTCCAACATGCCCACCTATTCAGGC
3781  ----------+----------+----------+----------+----------+----------+  3840
      ATGGCCGTCTTGAGGTGCGTGACGTCTTCGACGGAAAGGTTGTACGGGTGGATAAGTCCG

1227  H  F  T  M  R  S  P  F  K  C  D  A  C  L  R  M  G  N  L  Y   1246
      CACTTCACCATGAGGTCCCCCTTCAAGTGCGATGCCTGCCTGCGGATGGGGAATCTCTAT
3841  ----------+----------+----------+----------+----------+----------+  3900
      GTGAAGTGGTACTCCAGGGGGAAGTTCACGCTACGGACGGACGCCTACCCCTTAGAGATA

1247  D  I  D  E  D  Q  M  L  Q  E  T  G  N  P  A  T  G  E  Q  V   1266
      GACATCGATGAAGACCAGATGCTTCAGGAGACAGGTAACCCAGCCACCGGGGAGCAGGTC
3901  ----------+----------+----------+----------+----------+----------+  3960
      CTGTAGCTACTTCTGGTCTACGAAGTCCTCTGTCCATTGGGTCGGTGGCCCCTCGTCCAG
```

FIG. 1L

```
1267  Y   Q   Q   D   W   A   Q   N   N   A   L   Q   L   Q   K   N   K   L   R   I    1286
      TACCAGCAGGACTGGGCACAGAACAATGCCCTTCAATTACAAAAGAACAAGCTAAGGATT
3961  ----------+---------+---------+---------+---------+---------+                    4020
      ATGGTCGTCCTGACCCGTGTCTTGTTACGGGAAGTTAATGTTTTCTTGTTCGATTCCTAA

1287  S   R   Q   H   S   Y   D   N   I   V   D   K   P   R   E   L   D   L   S   R    1306
      AGCCGTCAGCATTCCTACGATAACATTGTCGACAAACCTAGGGAGCTAGACCTTAGCAGG
4021  ----------+---------+---------+---------+---------+---------+                    4080
      TCGGCAGTCGTAAGGATGCTATTGTAACAGCTGTTTGGATCCCTCGATCTGGAATCGTCC

1307  P   S   R   S   I   S   L   K   D   R   E   R   L   L   E   G   N   F   Y   G    1326
      CCCTCCCGGAGCATAAGCCTCAAGGACAGGGAACGGCTTCTGGAGGGAAATTTTTACGGC
4081  ----------+---------+---------+---------+---------+---------+                    4140
      GGGAGGGCCTCGTATTCGGAGTTCCTGTCCCTTGCCGAAGACCTCCCTTTAAAAATGCCG

1327  S   L   F   S   V   P   S   S   K   L   S   G   K   K   S   S   L   F   P   Q    1346
      AGCCTGTTTAGTGTCCCCTCAAGCAAAACTCTCGGGGAAAAAAAGCTCCCTTTTCCCCCAA
4141  ----------+---------+---------+---------+---------+---------+                    4200
      TCGGACAAATCACAGGGGAGTTCGTTTGAGAGCCCCTTTTTTTCGAGGGAAAAGGGGGTT

1347  G   L   E   D   S   K   R   S   K   S   L   L   P   D   H   T   S   D   N   P    1366
      GGTCTGGAGGACAGCAAGAGGAGCAAGTCTCTCTTGCCAGACCACACCTCCGATAACCCT
4201  ----------+---------+---------+---------+---------+---------+                    4260
      CCAGACCTCCTGTCGTTCTCCTCGTTCAGAGAGAACGGTCTGGTGTGGAGGCTATTGGGA

1367  F   L   H   S   H   R   D   D   Q   R   L   V   I   G   R   C   P   S   D   P    1386
      TTCCTCCACTCCCACAGGGATGACCAACGCTTGGTTATTGGGAGATGCCCCTCGGACCCT
4261  ----------+---------+---------+---------+---------+---------+                    4320
      AAGGAGGTGAGGGTGTCCCTACTGGTTGCGAACCAATAACCCTCTACGGGGAGCCTGGGA
```

FIG. 1M

```
1387  Y  K  H  S  L  P  S  Q  A  V  N  D  S  Y  L  R  S  S  L  R   1406
      TACAAACACTCGTTGCCATCCCAGGCGGTGAATGACAGCTATCTTCGGTCGTCCTTGAGG
4321  ----------+----------+----------+----------+----------+----------+  4380
      ATGTTTGTGAGCAACGGTAGGGTCCGCCACTTACTGTCGATAGAAGCCAGCAGGAACTCC

1407  S  T  A  S  Y  C  S  R  D  S  R  G  H  N  D  V  Y  I  S  E   1426
      TCAACGGCATCGTACTGTTCCAGGGACAGTCGGGGCCACAATGATGTGTATATTTCGGAG
4381  ----------+----------+----------+----------+----------+----------+  4440
      AGTTGCCGTAGCATGACAAGGTCCCTGTCAGCCCCGGTGTTACTACACATATAAAGCCTC

1427  H  V  M  P  Y  A  A  N  K  N  N  M  Y  S  T  P  R  V  L  N   1446
      CATGTTATGCCTTATGCTGCAAATAAGAATAATATGTACTCTACCCCCAGGGTTTTAAAT
4441  ----------+----------+----------+----------+----------+----------+  4500
      GTACAATACGGAATACGACGTTTATTCTTATTATACATGAGATGGGGGTCCCAAAATTTA

1447  S  C  S  N  R  R  V  Y  K  K  M  P  S  I  E  S  D  V          1464
      TCCTGCAGCAATAGACGCGTGTACAAGAAAATGCCTAGTATCGAATCTGATGTTTAAAAA
4501  ----------+----------+----------+----------+----------+----------+  4560
      AGGACGTCGTTATCTGCGCACATGTTCTTTTACGGATCATAGCTTAGACTACAAATTTTT

TCTTCCATTAATGTTTTATCTATAGGGAAATATACGTAATGGCCAATGTTCTGGAGGGTA
4561  ----------+----------+----------+----------+----------+----------+  4620
      AGAAGGTAATTACAAAATAGATATCCCTTTATATGCATTACCGGTTACAAGACCTCCCAT

AATGTTGGATGTCCAATAGTGCCCTGCTAAGAGGAAGAAGATGTAGGGAGGTATTTTGTT
4621  ----------+----------+----------+----------+----------+----------+  4680
      TTACAACCTACAGGTTATCACGGGACGATTCTCCTTCTTCTACATCCCTCCATAAAACAA
```

FIG. 1N

```
         GTTGTTGTTGTTGGCTCTTTTGCACACGGCTTCATGCCATAATCTTCCACTCAAGGAATC
4681     ------------+----------+----------+----------+----------+    4740
         CAACAACAACAACCGAGAAAACGTGTGCCGAAGTACGGTATTAGAAGGTGAGTTCCTTAG

TTGTGAGGTGTGTGCTGAGCATGGCAGACACCAGATAGGTGAGTCCTTAACCAAAAATAA
4741     ------------+----------+----------+----------+----------+    4800
         AACACTCCACACACGACTCGTACCGTCTGTGGTCTATCCACTCAGGAATTGGTTTTTATT

CTAACTACATAAGGGCAAGTCTCCGGGACATGCCTACTGGGTATGTTGGCAATAATGATG
4801     ------------+----------+----------+----------+----------+    4860
         GATTGATGTATTCCCGTTCAGAGGCCCTGTACGGATGACCCATACAACCGTTATTACTAC

CATTGGATGCCAATGGTGATGTTATGATTTCCTATATTCCAAATTCCATTAAGGTCAGCC
4861     ------------+----------+----------+----------+----------+    4920
         GTAACCTACGGTTACCACTACAATACTAAAGGATATAAGGTTTAAGGTAATTCCAGTCGG

CACCATGTAATTTTCTCATCAGAAATGCCTAATGGTTTCTCTAATACAGAATAAGCAATA
4921     ------------+----------+----------+----------+----------+    4980
         GTGGTACATTAAAAGAGTAGTCTTTACGGATTACCAAAGAGATTATGTCTTATTCGTTAT

TGGTGTGCATGTAAACCTGACACAGACAAAATAAAAACAGTTAAGAATGCATCTGCACTG
4981     ------------+----------+----------+----------+----------+    5040
         ACCACACGTACATTTGGACTGTGTCTGTTTTATTTTTGTCAATTCTTACGTAGACGTGAC

TAGTCGGATTTGAACATGTGCAAGAGATTAGGAAGTTTGGCTCGTAACAGTTTCAGCTTT
5041     ------------+----------+----------+----------+----------+    5100
         ATCAGCCTAAACTTGTACACGTTCTCTAATCCTTCAAACCGAGCATTGTCAAAGTCGAAA

CTTGTTATGCCTTCCATCACAGCCCAGGCTCACCCCAAGAACTCCAGGCTCCCCTAAAGA
5101     ------------+----------+----------+----------+----------+    5160
         GAACAATACGGAAGGTAGTGTCGGGTCCGAGTGGGGTTCTTGAGGTCCGAGGGGATTTCT
```

FIG. 10

```
          ATAGCAAATCAGTGTGTTCGTGATGACTGTGCTACCTTCATTATAGTTCATTTCCAAGAC
5161      ---------+---------+---------+---------+---------+---------+      5220
          TATCGTTTAGTCACACAAGCACTACTGACACGATGGAAGTAATATCAAGTAAAGGTTCTG

ACATCTGGAGCCAAAGGCCCGAGGGACCCTCAGGTGGGGAGAGCTACAGGAATCTCTTTG
5221      ---------+---------+---------+---------+---------+---------+      5280
          TGTAGACCTCGGTTTCCGGGCTCCCTGGGAGTCCACCCCTCTCGATGTCCTTAGAGAAAC

GATGTTGATGTGTGTTTCTCTCTACCCTCGGCTTCGATGGTCTTGTTCAGAGCTGCATAA
5281      ---------+---------+---------+---------+---------+---------+      5340
          CTACAACTACACACAAAGAGAGATGGGAGCCGAAGCTACCAGAACAAGTCTCGACGTATT

ACTAACACATTTATGTCTCCGAGATCTAAGTGTGGATCTTCTGTCTGTGACACAGTGGCC
5341      ---------+---------+---------+---------+---------+---------+      5400
          TGATTGTGTAAATACAGAGGCTCTAGATTCACACCTAGAAGACAGACACTGTGTCACCGG

ATTGTAGTTTATCCCGAAGACGCCTATGTACGTAAGTTTGCATTTCCTCCCTTCTGGTGA
5401      ---------+---------+---------+---------+---------+---------+      5460
          TAACATCAAATAGGGCTTCTGCGGATACATGCATTCAAACGTAAAGGAGGGAAGACCACT

TGACTCAGGGTTGTATAGTATCTGTTACCCCTTCCCTCCCAGAGTAACCATAACTCGTTC
5461      ---------+---------+---------+---------+---------+---------+      5520
          ACTGAGTCCCAACATATCATAGACAATGGGGAAGGGAGGGTCTCATTGGTATTGAGCAAG

CGTTTCCAAACAGCCATGGTGGTGTCCAATTAGCTGTGTATCGCTCTTCCCAGAGTTGTT
5521      ---------+---------+---------+---------+---------+---------+      5580
          GCAAAGGTTTGTCGGTACCACCACAGGTTAATCGACACATAGCGAGAAGGGTCTCAACAA
```

FIG. 1P

```
           AATGTGGTGACATGCACCAACAGCCGTATGTGTACTGTGATCTGTAAGAAGTACAATGCC
    5581   ----------+---------+---------+---------+---------+---------+   5640
           TTACACCACTGTACGTGGTTGTCGGCATACACATGACACTAGACATTCTTCATGTTACGG

ATCTGTCTGCCGAAGGCTAGCATGGTTTTAGGTTTATCTTCCTTCACATCCAGAAATTCT
    5641   ----------+---------+---------+---------+---------+---------+   5700
           TAGACAGACGGCTTCCGATCGTACCAAAATCCAAATAGAAGGAAGTGTAGGTCTTTAAGA

GTTGGACACTCACTTCCACCCCAAACTCCTCAAATCAAAAGCCTTCAAAACACGAGGCAC
    5701   ----------+---------+---------+---------+---------+---------+   5760
           CAACCTGTGAGTGAAGGTGGGGTTTGAGGAGTTTAGTTTTCGGAAGTTTTGTGCTCCGTG

TCTTGGATCTACCCTGAGTATCCTCCAAACTGTGGATACAGTTTAGTGAGACAAGCAATT
    5761   ----------+---------+---------+---------+---------+---------+   5820
           AGAACCTAGATGGGACTCATAGGAGGTTTGACACCTATGTCAAATCACTCTGTTCGTTAA

TCTCCCTTCTGAGTTATTCTCTCTGTTGGTGGCAAACCACTTCATAGCACCAACAGAGAT
    5821   ----------+---------+---------+---------+---------+---------+   5880
           AGAGGGAAGACTCAATAAGAGAGACAACCACCGTTTGGTGAAGTATCGTGGTTGTCTCTA

GTAGGAAAAATTCCTCAAAGTATTTGTCATTTCTGAGTCGCCTGCATTATCCCATTCTTA
    5881   ----------+---------+---------+---------+---------+---------+   5940
           CATCCTTTTTAAGGAGTTTCATAAACAGTAAAGACTCAGCGGACGTAATAGGGTAAGAAT

TTCTCCTCAAACCTGTGCATATATGACATGAAATGATATCCATTTTTTTTTTAAGTTAGA
    5941   ----------+---------+---------+---------+---------+---------+   6000
           AAGAGGAGTTTGGACACGTATATACTGTACTTTACTATAGGTAAAAAAAAAATTCAATCT

AACAGAGAGGGGAATACTTATGCATGGGGAGCCTGTTAGCACAGTGCCTGCCACAAAAAC
    6001   ----------+---------+---------+---------+---------+---------+   6060
           TTGTCTCTCCCCTTATGAATACGTACCCCTCGGACAATCGTGTCACGGACGGTGTTTTTG
```

FIG. 1Q

```
     AAGTGCCCCCGACAAGATAGTTGCTATGTTATGACACTTTCTCAGATCAGGATTTTCTAG
6061 ------------+----------+----------+----------+----------+----------+ 6120
     TTCACGGGGGCTGTTCTATCAACGATACAATACTGTGAAAGAGTCTAGTCCTAAAAGATC

TTTAAAAATTAAATATCATAAAACGGAATTC   (SEQ ID NO:1)
6121 ----------+----------+----------+- 6151
     AAATTTTTAATTTATAGTATTTTGCCTTAAG
```

FIG. 3

NR2A-1

```
    *   K  E  F  P  S  G  L  I  S  V  S  Y  D  D  W  D  Y  S  L  E
270
969 AAAAGAGTTTCCATCGGGACTCATTTCTGTCTCCTACGATGACTGGGACTACAGCCTGGAG        289  (SEQ ID NO:3)
        ||||||||||||||||||||||||||||||||||||||||||||||||||||||||||||     1029 (SEQ ID NO:4)
      --||||||||||||||||||||||||||||||||||||||||||||||||||||||||||
969 AGAAGAGTTTCCATCGGGACTCATTTCTGTCTCCTACGATGACTGGGACTACAGCCTGGAG       1029  (SEQ ID NO:5)
270     *  E  F  P  S  G  L  I  S  V  S  Y  D  D  W  D  Y  S  L  E       289  (SEQ ID NO:6)
```

NR2A-2

Eco RI     FIG. 4A

```
GAATTCCGGTAAGGCTCTGGAAAAGGGGGCGCTGGGAGCGCATTGCGAGGGGGCTGGAGA
----------+----------+----------+----------+----------+----------+ 60
CTTAAGGCCATTCCGAGACCTTTTCCCCCGCGACCCTCGCGTAACGCTCCCCCGACCTCT

GGGAGAGAGGAGCGGAAGCTGAGGGTGTGAAACGGCTGGCCCCGAACACACCTCGCGGCG
----------+----------+----------+----------+----------+----------+ 120
CCCTCTCTCCTCGCCTTCGACTCCCACACTTTGCCGACCGGGGCTTGTGTGGAGCGCCGC

CTCCAGTGATTCCTGGTGTCCGACCTCAGCCCCAGTCAGTGCGGGTCCAGTTTCCAGGCT
----------+----------+----------+----------+----------+----------+ 180
GAGGTCACTAAGGACCACAGGCTGGAGTCGGGGTCAGTCACGCCCAGGTCAAAGGTCCGA

CTCGCGGAAGGCCTGGCTGAGCACATGCGGCAGCCACGGTCGCCCTCCCTATTCCTCTTA
----------+----------+----------+----------+----------+----------+ 240
GAGCGCCTTCCGGACCGACTCGTGTACGCCGTCGGTGCCAGCGGGAGGGATAAGGAGAAT

GCCCGAGGAGGGGGGTCCCAAGTTACATGGCCACGCAGATGGGGCCTCTCCCTCATTTCT
----------+----------+----------+----------+----------+----------+ 300
CGGGCTCCTCCCCCCAGGGTTCAATGTACCGGTGCGTCTACCCCGGAGAGGGAGTAAAGA

GAACCTTGTGGGGAGGGGAACCTTGAAGGGAGCGCCCCCCAGAGCCATGGCTTAGGGCCT
----------+----------+----------+----------+----------+----------+ 360
CTTGGAACACCCCTCCCCTTGGAACTTCCCTCGCGGGGGGTCTCGGTACCGAATCCCGGA

CCCCCACCCCTCTGGAGCTCCAGTCTGCAAGAGTCAGGAGCCGAAATATCGCTGACTGTG
----------+----------+----------+----------+----------+----------+ 420
GGGGGTGGGGAGACCTCGAGGTCAGACGTTCTCAGTCCTCGGCTTTATAGCGACTGACAC
```

FIG. 4B

```
GGTGACGACTCTTGCGCGCACACACACATACAAGCGGGCACGACGCGTTCGGTCCTATTA
---------+---------+---------+---------+---------+---------+ 480
CCACTGCTGAGAACGCGCGTGTGTGTATGTTCGCCCGTGCTGCGCAAGCCAGGATAAT

AAAGGCACGCAAGGGTGCGGCTGCACGCGGTGACACGGACCCCTCTAACGTTTCCAAACT
---------+---------+---------+---------+---------+---------+ 540
TTTCCGTGCGTTCCCACGCCGACGTGCGCCACTGTGCCTGGGGAGATTGCAAAGGTTTGA

GAGCTCCCTGCAGGTCCCCGACAGCACAGGCCCCTGTCCCAGGACCCCTCCAGGCACGCG
---------+---------+---------+---------+---------+---------+ 600
CTCGAGGGACGTCCAGGGGCTGTCGTGTCCGGGGACAGGGTCCTGGGGAGGTCCGTGCGC

CTCACACGCACACGCGCGCTCCCCGGCTCACGCGCGCTCCGACACACACGCTCACGCGAA
---------+---------+---------+---------+---------+---------+ 660
GAGTGTGCGTGTGCGCGCGAGGGGCCGAGTGCGCGCGAGGCTGTGTGTGCGAGTGCGCTT

CGCAGGCGCACGCTCTGGCGCGGGAGGCGCCCCTTCGCCTCCGTGTTGGGAAGCGGGGGC
---------+---------+---------+---------+---------+---------+ 720
GCGTCCGCGTGCGAGACCGCGCCCTCCGCGGGGAAGCGGAGGCACAACCCTTCGCCCCCG

GGCGGGAGGGGCAGGAGACGTTGGCCCCGCTCGCGTTTCTGCAGCTGCTGCAGTCGCCGC
---------+---------+---------+---------+---------+---------+ 780
CCGCCCTCCCCGTCCTCTGCAACCGGGGCGAGCGCAAAGACGTCGACGACGTCAGCGGCG

AGCGTCCGGACCGGAACCAGCGCCGTCCGCGGAGCCGCCGCCGCCGCCGCCGGGCCCTTT
---------+---------+---------+---------+---------+---------+ 840
TCGCAGGCCTGGCCTTGGTCGCGGCAGGCGCCTCGGCGGCGGCGGCGGCGGCCCGGGAAA

CCAAGCCGGGCGCTCGGAGCTGTGCCCGGCCCCGCTTCAGCACCGCGGACAGCTCCGGCC
---------+---------+---------+---------+---------+---------+ 900
GGTTCGGCCCGCGAGCCTCGACACGGGCCGGGGCGAAGTCGTGGCGCCTGTCGAGGCCGG
```

FIG. 4C

```
GCGTGGGGCTGAGCCGAGCCCCCGCGCACGCTTCAGCCCCCTTCCCTCGGCCGACGTCCC
----------+----------+----------+----------+----------+----------+ 960
CGCACCCCGACTCGGCTCGGGGGCGCGTGCGAAGTCGGGGGAAGGGAGCCGGCTGCAGGG

GGGACCGCCGCTCCGGGGGAGACGTGGCGTCCGCAGCCCGCGGGGCCGGGCGAGCGCAGG
----------+----------+----------+----------+----------+----------+1020
CCCTGGCGGCGAGGCCCCCTCTGCACCGCAGGCGTCGGGCGCCCCGGCCCGCTCGCGTCC

ACGGCCCGGAAGCCCCGCGGGGGATGCGCCGAGGGCCCGCGTTCGCGCCGCGCAGAGCCA
----------+----------+----------+----------+----------+----------+1080
TGCCGGGCCTTCGGGGCGCCCCCTACGCGGCTCCCGGGCGCAAGCGCGGCGCGTCTCGGT

|--------------signal-peptide---------------
              M  S  T  M  R  L  L  T  L  A  L  L  F  S   -4
GGCCCGCGGCCCGAGCCCATGAGCACCATGCGCCTGCTGACGCTCGCCCTGCTGTTCTCC
----------+----------+----------+----------+----------+----------+1140
CCGGGCGCCGGGCTCGGGTACTCGTGGTACGCGGACGACTGCGAGCGGGACGACAAGAGG ----------|
    C  S  V  A  R  A  A  C  D  P  K  I  V  N  I  G  A  V  L  S   16
TGCTCCGTCGCCCGTGCCGCGTGCGACCCCAAGATCGTCAACATTGGCGCGGTGCTGAGC
----------+----------+----------+----------+----------+----------+1200
ACGAGGCAGCGGGCACGGCGCACGCTGGGGTTCTAGCAGTTGTAACCGCGCCACGACTCG T  R  K  H  E  Q  M  F  R  E  A  V  N  Q  A  N  K  R  H  G   36
ACGCGGAAGCACGAGCAGATGTTCCGCGAGGCCGTGAACCAGGCCAACAAGCGGCACGGC
----------+----------+----------+----------+----------+----------+1260
TGCGCCTTCGTGCTCGTCTACAAGGCGCTCCGGCACTTGGTCCGGTTGTTCGCCGTGCCG
```

FIG. 4D

```
       S   W   K   I   Q   L   N   A   T   S   V   T   H   K   P   N   A   I   Q   M    56
     TCCTGGAAGATTCAGCTCAATGCCACCTCCGTCACGCACAAGCCCAACGCCATCCAGATG
     ----------+---------+---------+---------+---------+---------+1320
     AGGACCTTCTAAGTCGAGTTACGGTGGAGGCAGTGCGTGTTCGGGTTGCGGTAGGTCTAC

A   L   S   V   C   E   D   L   I   S   S   Q   V   Y   A   I   L   V   S   H    76
     GCTCTGTCGGTGTGCGAGGACCTCATCTCCAGCCAGGTCTACGCCATCCTAGTTAGCCAT
     ----------+---------+---------+---------+---------+---------+1380
     CGAGACAGCCACACGCTCCTGGAGTAGAGGTCGGTCCAGATGCGGTAGGATCAATCGGTA

P   P   T   P   N   D   H   F   T   P   T   P   V   S   Y   T   A   G   F   Y    96
     CCACCTACCCCCAACGACCACTTCACTCCCACCCCTGTCTCCTACACAGCCGGCTTCTAC
     ----------+---------+---------+---------+---------+---------+1440
     GGTGGATGGGGGTTGCTGGTGAAGTGAGGGTGGGGACAGAGGATGTGTCGGCCGAAGATG

R   I   P   V   L   G   L   T   T   R   M   S   I   Y   S   D   K   S   I   H   116
     CGCATACCCGTGCTGGGGCTGACCACCCGCATGTCCATCTACTCGGACAAGAGCATCCAC
     ----------+---------+---------+---------+---------+---------+1500
     GCGTATGGGCACGACCCCGACTGGTGGGCGTACAGGTAGATGAGCCTGTTCTCGTAGGTG

L   S   F   L   R   T   V   P   P   Y   S   H   Q   S   S   V   W   F   E   M   136
     CTGAGCTTCCTGCGCACCGTGCCGCCCTACTCCCACCAGTCCAGCGTGTGGTTTGAGATG
     ----------+---------+---------+---------+---------+---------+1560
     GACTCGAAGGACGCGTGGCACGGCGGGATGAGGGTGGTCAGGTCGCACACCAAACTCTAC

M   R   V   Y   S   W   N   H   I   I   L   L   V   S   D   D   H   E   G   R   156
     ATGCGTGTCTACAGCTGGAACCACATCATCCTGCTGGTCAGCGACGACCACGAGGGCCGG
     ----------+---------+---------+---------+---------+---------+1620
     TACGCACAGATGTCGACCTTGGTGTAGTAGGACGACCAGTCGCTGCTGGTGCTCCCGGCC
```

FIG. 4E

```
  A   A   Q   K   R   L   E   T   L   L   E   E   R   E   S   K   A   E   K   V   176
GCGGCTCAGAAACGCCTGGAGACGCTGCTGGAGGAGCGTGAGTCCAAGGCAGAGAAGGTG
----------+----------+----------+----------+----------+----------+1680
CGCCGAGTCTTTGCGGACCTCTGCGACGACCTCCTCGCACTCAGGTTCCGTCTCTTCCAC

L   Q   F   D   P   G   T   K   N   V   T   A   L   L   M   E   A   K   E   L   196
CTGCAGTTTGACCCAGGGACCAAGAACGTGACGGCCCTGCTGATGGAGGCGAAAGAGCTG
----------+----------+----------+----------+----------+----------+1740
GACGTCAAACTGGGTCCCTGGTTCTTGCACTGCCGGGACGACTACCTCCGCTTTCTCGAC

E   A   R   V   I   I   L   S   A   S   E   D   D   A   A   T   V   Y   R   A   216
GAGGCCCGGGTCATCATCCTTTCTGCCAGCGAGGACGATGCTGCCACTGTATACCGCGCA
----------+----------+----------+----------+----------+----------+1800
CTCCGGGCCCAGTAGTAGGAAAGACGGTCGCTCCTGCTACGACGGTGACATATGGCGCGT

Bgl II
  A   A   M   L   N   M   T   G   S   G   Y   V   W   L   V   G   E   R   E   I   236
GCCGCGATGCTGAACATGACGGGCTCCGGGTACGTGTGGCTGGTCGGCGAGCGCGAGATC
----------+----------+----------+----------+----------+----------+1860
CGGCGCTACGACTTGTACTGCCCGAGGCCCATGCACACCGACCAGCCGCTCGCGCTCTAG

S   G   N   A   L   R   Y   A   P   D   G   I   L   G   L   Q   L   I   N   G   256
TCGGGGAACGCCCTGCGCTACGCCCCAGACGGCATCCTCGGGCTGCAGCTCATCAACGGC
----------+----------+----------+----------+----------+----------+1920
AGCCCCTTGCGGGACGCGATGCGGGGTCTGCCGTAGGAGCCCGACGTCGAGTAGTTGCCG

K   N   E   S   A   H   I   S   D   A   V   G   V   V   A   Q   A   V   H   E   276
AAGAACGAGTCGGCCCACATCAGCGACGCCGTGGGCGTGGTGGCCCAGGCCGTGCACGAG
----------+----------+----------+----------+----------+----------+1980
TTCTTGCTCAGCCGGGTGTAGTCGCTGCGGCACCCGCACCACCGGGTCCGGCACGTGCTC
```

FIG. 4F

```
      L   L   E   K   E   N   I   T   D   P   P   R   G   C   V   G   N   T   N   I   296
     CTCCTCGAGAAGGAGAACATCACCGACCCGCCGCGGGGCTGCGTGGGCAACACCAACATC
     ----------+----------+----------+----------+----------+----------+2040
     GAGGAGCTCTTCCTCTTGTAGTGGCTGGGCGGCGCCCCGACGCACCCGTTGTGGTTGTAG

W   K   T   G   P   L   F   K   R   V   L   M   S   S   K   Y   A   D   G   V   316
     TGGAAGACCGGGCCGCTCTTCAAGAGAGTGCTGATGTCTTCCAAGTATGCGGATGGGGTG
     ----------+----------+----------+----------+----------+----------+2100
     ACCTTCTGGCCCGGCGAGAAGTTCTCTCACGACTACAGAAGGTTCATACGCCTACCCCAC

T   G   R   V   E   F   N   E   D   G   D   R   K   F   A   N   Y   S   I   M   336
     ACTGGTCGCGTGGAGTTCAATGAGGATGGGGACCGGAAGTTCGCCAACTACAGCATCATG
     ----------+----------+----------+----------+----------+----------+2160
     TGACCAGCGCACCTCAAGTTACTCCTACCCCTGGCCTTCAAGCGGTTGATGTCGTAGTAC

N   L   Q   N   R   K   L   V   Q   V   G   I   Y   N   G   T   H   V   I   P   356
     AACCTGCAGAACCGCAAGCTGGTGCAAGTGGGCATCTACAATGGCACCCACGTCATCCCT
     ----------+----------+----------+----------+----------+----------+2220
     TTGGACGTCTTGGCGTTCGACCACGTTCACCCGTAGATGTTACCGTGGGTGCAGTAGGGA

N   D   R   K   I   I   W   P   G   G   E   T   E   K   P   R   G   Y   Q   M   376
     AATGACAGGAAGATCATCTGGCCAGGCGGAGAGACAGAGAAGCCTCGAGGGTACCAGATG
     ----------+----------+----------+----------+----------+----------+2280
     TTACTGTCCTTCTAGTAGACCGGTCCGCCTCTCTGTCTCTTCGGAGCTCCCATGGTCTAC

S   T   R   L   K   I   V   T   I   H   Q   E   P   F   V   Y   V   K   P   T   396
     TCCACCAGACTGAAGATTGTGACGATCCACCAGGAGCCCTTCGTGTACGTCAAGCCCACG
     ----------+----------+----------+----------+----------+----------+2340
     AGGTGGTCTGACTTCTAACACTGCTAGGTGGTCCTCGGGAAGCACATGCAGTTCGGGTGC
```

FIG. 4G

```
      L   S   D   G   T   C   K   E   E   F   T   V   N   G   D   P   V   K   K   V  416
    CTGAGTGATGGGACATGCAAGGAGGAGTTCACAGTCAACGGCGACCCAGTCAAGAAGGTG
    ----------+----------+----------+----------+----------+----------+2400
    GACTCACTACCCTGTACGTTCCTCCTCAAGTGTCAGTTGCCGCTGGGTCAGTTCTTCCAC

I   C   T   G   P   N   D   T   S   P   G   S   P   R   H   T   V   P   Q   C  436
    ATCTGCACCGGGCCCAACGACACGTCGCCGGGCAGCCCCCGCCACACGGTGCCTCAGTGT
    ----------+----------+----------+----------+----------+----------+2460
    TAGACGTGGCCCGGGTTGCTGTGCAGCGGCCCGTCGGGGGCGGTGTGCCACGGAGTCACA

C   Y   G   F   C   I   D   L   L   I   K   L   A   R   T   M   N   F   T   Y  456
    TGCTACGGCTTTTGCATCGACCTGCTCATCAAGCTGGCACGGACCATGAACTTCACCTAC
    ----------+----------+----------+----------+----------+----------+2520
    ACGATGCCGAAAACGTAGCTGGACGAGTAGTTCGACCGTGCCTGGTACTTGAAGTGGATG

E   V   H   L   V   A   D   G   K   F   G   T   Q   E   R   V   N   N   S   N  476
    GAGGTGCACCTGGTGGCAGATGGCAAGTTCGGCACACAGGAGCGGGTGAACAACAGCAAC
    ----------+----------+----------+----------+----------+----------+2580
    CTCCACGTGGACCACCGTCTACCGTTCAAGCCGTGTGTCCTCGCCCACTTGTTGTCGTTG

K   K   E   W   N   G   M   M   G   E   L   L   S   G   Q   A   D   M   I   V  496
    AAGAAGGAGTGGAATGGGATGATGGGCGAGCTGCTCAGCGGGCAGGCAGACATGATCGTG
    ----------+----------+----------+----------+----------+----------+2640
    TTCTTCCTCACCTTACCCTACTACCCGCTCGACGAGTCGCCCGTCCGTCTGTACTAGCAC

A   P   L   T   I   N   N   E   R   A   Q   Y   I   E   F   S   K   P   F   K  516
    GCGCCGCTAACCATAAACAACGAGCGCGCGCAGTACATCGAGTTTTCCAAGCCCTTCAAG
    ----------+----------+----------+----------+----------+----------+2700
    CGCGGCGATTGGTATTTGTTGCTCGCGCGCGTCATGTAGCTCAAAAGGTTCGGGAAGTTC
```

FIG. 4H

```
     Y  Q  G  L  T  I  L  V  K  K  E  I  P  R  S  T  L  D  S  F   536
     TACCAGGGCCTGACTATTCTGGTCAAGAAGGAGATTCCCCGGAGCACGCTGGACTCGTTC
     ---------+---------+---------+---------+---------+---------+2760
     ATGGTCCCGGACTGATAAGACCAGTTCTTCCTCTAAGGGGCCTCGTGCGACCTGAGCAAG

|-------------------TM-1------------------
     M  Q  P  F  Q  S  T  L  W  L  L  V  G  L  S  V  H  V  V  A   556
     ATGCAGCCGTTCCAGAGCACACTGTGGCTGCTGGTGGGGCTGTCGGTGCACGTGGTGGCC
     ---------+---------+---------+---------+---------+---------+2820
     TACGTCGGCAAGGTCTCGTGTGACACCGACGACCACCCCGACAGCCACGTGCACCACCGG

-----------------|
     V  M  L  Y  L  D  R  F  S  P  F  G  R  F  K  V  N  S  E   576
     GTGATGCTGTACCTGCTGGACCGCTTCAGCCCCTTCGGCCGGTTCAAGGTGAACAGCGAG
     ---------+---------+---------+---------+---------+---------+2880
     CACTACGACATGGACGACCTGGCGAAGTCGGGGAAGCCGGCCAAGTTCCACTTGTCGCTC

|---------------TM-2------------------
     E  E  E  D  A  L  T  L  S  S  A  M  W  F  S  W  G  V  L   596
     GAGGAGGAGGAGGACGCACTGACCCTGTCCTCGGCCATGTGGTTCTCCTGGGGCGTCCTG
     ---------+---------+---------+---------+---------+---------+2940
     CTCCTCCTCCTCCTGCGTGACTGGGACAGGAGCCGGTACACCAAGAGGACCCCGCAGGAC

-----------------|                          |------------
     L  N  S  G  I  G  E  G  A  P  R  S  F  S  A  R  I  L  G  M   616
     CTCAACTCCGGCATCGGGGAAGGCGCCCCCAGAAGCTTCTCAGCGCGCATCCTGGGCATG
     ---------+---------+---------+---------+---------+---------+3000
     GAGTTGAGGCCGTAGCCCCTTCCGCGGGGGTCTTCGAAGAGTCGCGCGTAGGACCCGTAC
```

FIG. 41

```
---------TM-3-----------------------------------|
  V   W   A   G   F   A   M   I   I   V   A   S   Y   T   A   N   L   A   A   F    636
GTGTGGGCCGGCTTTGCCATGATCATCGTGGCCTCCTACACCGCCAACCTGGCGGCCTTC
----------+---------+---------+---------+---------+---------+---------+3060
CACACCCGGCCGAAACGGTACTAGTAGCACCGGAGGATGTGGCGGTTGGACCGCCGGAAG

L   V   L   D   R   P   E   E   R   I   T   G   I   N   D   P   R   L   R   N    656
CTGGTGCTGGACCGGCCGGAGGAGCGCATCACGGGCATCAACGACCCTCGGCTGAGGAAC
----------+---------+---------+---------+---------+---------+---------+3120
GACCACGACCTGGCCGGCCTCCTCGCGTAGTGCCCGTAGTTGCTGGGAGCCGACTCCTTG

P   S   D   K   F   I   Y   A   T   V   K   Q   S   S   V   D   I   Y   F   R    676
CCCTCGGACAAGTTTATCTACGCCACGGTGAAGCAGAGCTCCGTGGATATCTACTTCCGG
----------+---------+---------+---------+---------+---------+---------+3180
GGGAGCCTGTTCAAATAGATGCGGTGCCACTTCGTCTCGAGGCACCTATAGATGAAGGCC

R   Q   V   E   L   S   T   M   Y   R   H   M   E   K   H   N   Y   E   S   A    696
CGCCAGGTGGAGCTGAGCACCATGTACCGGCATATGGAGAAGCACAACTACGAGAGTGCG
----------+---------+---------+---------+---------+---------+---------+3240
GCGGTCCACCTCGACTCGTGGTACATGGCCGTATACCTCTTCGTGTTGATGCTCTCACGC

A   E   A   I   Q   A   V   R   D   N   K   L   H   A   F   I   W   D   S   A    716
GCGGAGGCCATCCAGGCCGTGAGAGACAACAAGCTGCATGCCTTCATCTGGGACTCGGCG
----------+---------+---------+---------+---------+---------+---------+3300
CGCCTCCGGTAGGTCCGGCACTCTCTGTTGTTCGACGTACGGAAGTAGACCCTGAGCCGC

V   L   E   F   E   A   S   Q   K   C   D   L   V   T   T   G   E   L   F   F    736
GTGCTGGAGTTCGAGGCCTCGCAGAAGTGCGACCTGGTGACGACTGGAGAGCTGTTTTTC
----------+---------+---------+---------+---------+---------+---------+3360
CACGACCTCAAGCTCCGGAGCGTCTTCACGCTGGACCACTGCTGACCTCTCGACAAAAAG
```

FIG. 4J

```
    R  S  G  F  G  I  G  M  R  K  D  S  P  W  K  Q  N  V  S  L    756
CGCTCGGGCTTCGGCATAGGCATGCGCAAAGACAGCCCCTGGAAGCAGAACGTCTCCCTG
----------+----------+----------+----------+----------+----------+3420
GCGAGCCCGAAGCCGTATCCGTACGCGTTTCTGTCGGGGACCTTCGTCTTGCAGAGGGAC

S  I  L  K  S  H  E  N  G  F  M  E  D  L  D  K  T  W  V  R    776
TCCATCCTCAAGTCCCACGAGAATGGCTTCATGGAAGACCTGGACAAGACGTGGGTTCGG
----------+----------+----------+----------+----------+----------+3480
AGGTAGGAGTTCAGGGTGCTCTTACCGAAGTACCTTCTGGACCTGTTCTGCACCCAAGCC

|-------
    Y  Q  E  C  D  S  R  S  N  A  P  A  T  L  T  F  E  N  M  A    796
TATCAGGAATGTGACTCGCGCAGCAACGCCCCTGCGACCCTTACTTTTGAGAACATGGCC
----------+----------+----------+----------+----------+----------+3540
ATAGTCCTTACACTGAGCGCGTCGTTGCGGGGACGCTGGGAATGAAAACTCTTGTACCGG

------------------TM-4------------------------------------|
    G  V  F  M  L  V  A  G  G  I  V  A  G  I  F  L  I  F  I  E    816
GGGGTCTTCATGCTGGTAGCTGGGGGCATCGTGGCCGGGATCTTCCTGATTTTTCATCGAG
----------+----------+----------+----------+----------+----------+3600
CCCCAGAAGTACGACCATCGACCCCCGTAGCACCGGCCCTAGAAGGACTAAAAGTAGCTC

I  A  Y  K  R  H  K  D  A  R  R  K  Q  M  Q  L  A  F  A  A    836
ATTGCCTACAAGCGGCACAAGGATGCTCGCCGGAAGCAGATGCAGCTGGCCTTTGCCGCC
----------+----------+----------+----------+----------+----------+3660
TAACGGATGTTCGCCGTGTTCCTACGAGCGGCCTTCGTCTACGTCGACCGGAAACGGCGG

V  N  V  W  R  K  N  L  Q  Q  Y  H  P  T  D  I  T  G  P  L    856
GTTAACGTGTGGCGGAAGAACCTGCAGCAGTACCATCCCACTGATATCACGGGCCCGCTC
----------+----------+----------+----------+----------+----------+3720
CAATTGCACACCGCCTTCTTGGACGTCGTCATGGTAGGGTGACTATAGTGCCCGGGCGAG
```

FIG. 4K

```
  N   L   S   D   P   S   V   S   T   V   V                              867
AACCTCTCAGATCCCTCGGTCAGCACCGTGGTGTGAGGCCCCCGGAGGCGCCCACCTGCC
----------+----------+----------+----------+----------+----------+3780
TTGGAGAGTCTAGGGAGCCAGTCGTGGCACCACACTCCGGGGGCCTCCGCGGGTGGACGG

CAGTTAGCCCCGGCCAAGGACACTGATGGGTCCTGCTGCTCGGGAAGGCCTGAGGGAAGCC
----------+----------+----------+----------+----------+----------+3840
GTCAATCGGGCCGGTTCCTGTGACTACCCAGGACGACGAGCCCTTCCGGACTCCCTTCGG

CACCCGCCCCAGAGACTGCCCACCCTGGGCCTCCCGTCCGTCCGCCCGCCCACCCCGCTG
----------+----------+----------+----------+----------+----------+3900
GTGGGCGGGGTCTCTGACGGGTGGGACCCGGAGGGCAGGCAGGCGGGCGGGTGGGGCGAC

CCTGGCGGGCAGCCCCTGCTGGACCAAGGTGCGGACCGGAGCGGCTGAGGACGGGGCAGA
----------+----------+----------+----------+----------+----------+3960
GGACCGCCCGTCGGGGACGACCTGGTTCCACGCCTGGCCTCGCCGACTCCTGCCCCGTCT

GCTGAGTCGGCTGGGCAGGGCGCAGGGCGCTCCGGCAGAGGCAGGGCCCTGGGGTCTCTG
----------+----------+----------+----------+----------+----------+4020
CGACTCAGCCGACCCGTCCCGCGTCCCGCGAGGCCGTCTCCGTCCCGGGACCCCAGAGAC

AGCAGTGGGGAGCGGGGGCTAACTGGCCCCAGGCGAAGGGGCTTGGAGCAGAGACGGCAG
----------+----------+----------+----------+----------+----------+4080
TCGTCACCCCTCGCCCCCGATTGACCGGGGTCCGCTTCCCCGAACCTCGTCTCTGCCGTC

CCCCATCCTTCCCGCAGCACCAGCCTGAGCCACAGTGGGGCCCATGGCCCCAGCTGGCTG
----------+----------+----------+----------+----------+----------+4140
GGGGTAGGAAGGGCGTCGTGGTCGGACTCGGTGTCACCCCGGGTACCGGGGTCGACCGAC

GGTCGCCCCTCCTCGGGCGCCTGCGCTCCTCTGCAGCCTGAGCTCCACCCTCCCCTCTTC
----------+----------+----------+----------+----------+----------+4200
CCAGCGGGGAGGAGCCCGCGGACGCGAGGAGACGTCGGACTCGAGGTGGGAGGGGAGAAG
```

FIG. 4L

```
TTGCGGCACCGCCCACCCACACCCCGTCTGCCCCTTGACCCCACACGCCGGGGCTGGCCC
---------+---------+---------+---------+---------+---------+4260
AACGCCGTGGCGGGTGGGTGTGGGGCAGACGGGGAACTGGGGTGTGCGGCCCCGACCGGG

TGCCCTCCCCCACGGCCGTCCCTGACTTCCCAGCTGGCAGCGCCTCCCGCCGCCTCGGGC
---------+---------+---------+---------+---------+---------+4320
ACGGGAGGGGGTGCCGGCAGGGACTGAAGGGTCGACCGTCGCGGAGGGCGGCGGAGCCCG

CGCCTCCTCCAGACTCGAGAGGGCTGAGCCCCTCCTCTCCTCGTCCGGCCTGCAGCCCAG
---------+---------+---------+---------+---------+---------+4380
GCGGAGGAGGTCTGAGCTCTCCCGACTCGGGGAGGAGAGGAGCAGGCCGGACGTCGGGTC

AACGGGCCTCCCCGGGGGTCCCCGGACGCTGGCTCGGGACTGTCTTCAACCCTGCCCTGC
---------+---------+---------+---------+---------+---------+4440
TTGCCCGGAGGGGCCCCCAGGGGCCTGCGACCGAGCCCTGACAGAAGTTGGGACGGGACG

ACCTTGGGCACGGGAGAGCGCCACCCGCCCGCCCCCGCCCTCGCTCCGGGTGCGTGACCG
---------+---------+---------+---------+---------+---------+4500
TGGAACCCGTGCCCTCTCGCGGTGGGCGGGCGGGGCGGGAGCGAGGCCCACGCACTGGC

GCCCGCCACCTTGTACAGAACCAGCACTCCCAGGGCCCGAGCGCGTGCCTTCCCCGTGCG
---------+---------+---------+---------+---------+---------+4560
CGGGCGGTGGAACATGTCTTGGTCGTGAGGGTCCCGGGCTCGCGCACGGAAGGGGCACGC

GCCCGTGCGCAGCCGCGCTCTGCCCCTCCGTCCCCAGGGTGCAGGCGCGCACCGCCCAAC
---------+---------+---------+---------+---------+---------+4620
CGGGCACGCGTCGGCGCGAGACGGGGAGGCAGGGGTCCCACGTCCGCGCGTGGCGGGTTG

Eco RI
CCCCACCTCCCGGTGTATGCAGTGGTGATGCCGGAATTC      (SEQ ID NO:9)
---------+---------+---------+---------+4659
GGGGTGGAGGGCCACATACGTCACCACTACGGCCTTAAG
```

FIG. 5A

```
..................................................  1
ACAGCGGCCCGGCCCACGCAGAGCCCCGGAGCACCACGGGGTCGGGGGAGGAGCACCCCC +236  2
|||||||||||||||||||||||||||||||||||||||||||||||||||||||||||
ACAGCGGCCCGGCCCACGCAGAGCCCCGGAGCACCACGGGGTCGGGGGAGGAGCACCCCC +347  3A
|||||||||||||||||||||||||||||||||||||||||||||||||||||||||||
ACAGCGGCCCGGCCCACGCAGAGCCCCGGAGCACCACGGGGTCGGGGGAGGAGCACCCCC +347  3C

..................................................  1
AGCCTCCCCCAGGCTGCGCCTGCCCGCCCGCCGGTTGGCCGGCTGGCCGGTCCACCCCGT +296  2
|||||||||||||||||||||||||||||||||||||||||||||||||||||||||||
AGCCTCCCCCAGGCTGCGCCTGCCCGCCCGCCGGTTGGCCGGCTGGCCGGTCCACCCCGT +407  3A
|||||||||||||||||||||||||||||||||||||||||||||||||||||||||||
AGCCTCCCCCAGGCTGCGCCTGCCCGCCCGCCGGTTGGCCGGCTGGCCGGTCCACCCCGT +407  3C

..................................................  1
CCCGGCCCCGCGCGTGCCCCCAGCGTGGGGCTAACGGGCGCCTTGTCTGTGTATTTCTAT +356  2
|||||||||||||||||||||||||||||||||||||||||||||||||||||||||||
CCCGGCCCCGCGCGTGCCCCCAGCGTGGGGCTAACGGGCGCCTTGTCTGTGTATTTCTAT +467  3A
|||||||||||||||||||||||||||||||||||||||||||||||||||||||||||
CCCGGCCCCGCGCGTGCCCCCAGCGTGGGGCTAACGGGCGCCTTGTCTGTGTATTTCTAT +467  3C

3688 .......CAGTACCATCCCACT 3702  humNMDAR1-1   (SEQ ID NO:10)
             ||||||||||||||||
+357 TTTGCAGCAGTACCATCCCACT 4065  humNMDAR1-2   (SEQ ID NO:11)
     ||||||||||||||||||||||
+468 TTTGCAGCAGTACCATCCCACT 4176  humNMDAR1-3A  (SEQ ID NO:12)
     ||||||||||||||||||||||
+468 TTTGCAGCAGTACCATCCCACT 4176  humNMDAR1-3C  (SEQ ID NO:13)
```

FIG. 5B

```
3675 GAAGAACCTGCAG............................................ 3687  1
     |||||||||||||
3675 GAAGAACCTGCAG............................................ 3687  2
     |||||||||||||
3675 GAAGAACCTGCAGGATAGAAAGAGTGGTAGAGCAGAGCCTGACCCTAAAAAGAAAGCCAC +47  3A
     ||||||||||||||||||||||||||||||||||||||||||||||||||||||||||||
3675 GAAGAACCTGCAGGATAGAAAGAGTGGTAGAGCAGAGCCTGACCCTAAAAAGAAAGCCAC +47  3C

...........................................................  1
     ...........................................................  2
     ATTTAGGGCTATCACCTCCACCCTGGCTTCCAGCTTCAAGAGGCGTAGGTCCTCCAAAGA +107 3A
     ||||||||||||||||||||||||||||||||||||||||||||||||||||||||||||
     ATTTAGGGCTATCACCTCCACCCTGGCTTCCAGCTTCAAGAGGCGTAGGTCCTCCAAAGA +107 3C

...........................................................  1
     ....AGCACCGGGGGTGGACGCGGCGCTTTGCAAAACCAAAAAGACACAGTGCTGCCGCG +56  2
         ||||||||||||||||||||||||||||||||||||||||||||||||||||||||
     CACGAGCACCGGGGGTGGACGCGGCGCTTTGCAAAACCAAAAAGACACAGTGCTGCCGCG +167 3A
     ||||||||||||||||||||||||||||||||||||||||||||||||||||||||||||
     CACGAGCACCGGGGGTGGACGCGGCGCTTTGCAAAACCAAAAAGACACAGTGCTGCCGCG +167 3C

...........................................................  1
     ACGCGCTATTGAGAGGGAGGAGGGCCAGCTGCAGCTGTGTTCCCGTCATAGGGAGAGCTG +116 2
     ||||||||||||||||||||||||||||||||||||||||||||||||||||||||||||
     ACGCGCTATTGAGAGGGAGGAGGGCCAGCTGCAGCTGTGTTCCCGTCATAGGGAGAGCTG +227 3A
     |||||||||||||||||||||||||||||||||||||||||||||||| ||||||||
     ACGCGCTATTGAGAGGGAGGAGGGCCAGCTGCAGCTGTGTTCCCGTCATACGGAGAGCTG +227 3C
                                                      *     END

...........................................................  1
     AGACTCCCCGCCCGCCCTCCTCTGCCCCCTCCCCCGCAGACAGACAGACAGACGGATGGG +176 2
     ||||||||||||||||||||||||||||||||||||||||||||||||||||||||||||
     AGACTCCCCGCCCGCCCTCCTCTGCCCCCTCCCCCGCAGACAGACAGACAGACGGATGGG +287 3A
     ||||||||||||||||||||||||||||||||||||||||||||||||||||||||||||
     AGACTCCCCGCCCGCCCTCCTCTGCCCCCTCCCCCGCAGACAGACAGACAGACGGATGGG +287 3C
```

FIG. 6

```
         NMDAR1-1
803  AGGIVAGIFLIFIEIAYKRHKDARRKQMQLAFAAVNVWRKNLQ............  845
     ||||||||||||||||||||||||||||||||||||||||||
803  AGGIVAGIFLIFIEIAYKRHKDARRKQMQLAFAAVNVWRKNLQDRKSGRAEPDPKKKATF  862
         NMDAR1-4                                         (SEQ ID NO:16)
                                                          (SEQ ID NO:17)

NMDAR1-1 (cont'd)
846  ..........................QYHPTDITGPLNLSDPSVSTVV  867
                               ||||||||||||||||||||||||
863  RAITSTLASSFKRRRSSKDTQYHPTDITGPLNLSDPSVSTVV  904
         NMDAR1-4 (cont'd)
```

FIG. 7

```
                          <--- 21 aa insert --->
NMDAR1-5/6/7/8
160  KRLETLLEERESKSKKRNYENLDQLSYDNKRGPKAEKVLQFDPGTKN  206   (SEQ ID NO:18)
     |||||||||||||                        |||||||||||||||
160  KRLETLLEERESK.........................AEKVLQFDPGTKN  185   (SEQ ID NO:19)
NMDAR1-1/2/3/4
```

Homomeric NMDA R1

Homomeric NMDA R2A

FIG. 8C Heteromeric NMDAR1/NMDAR2A
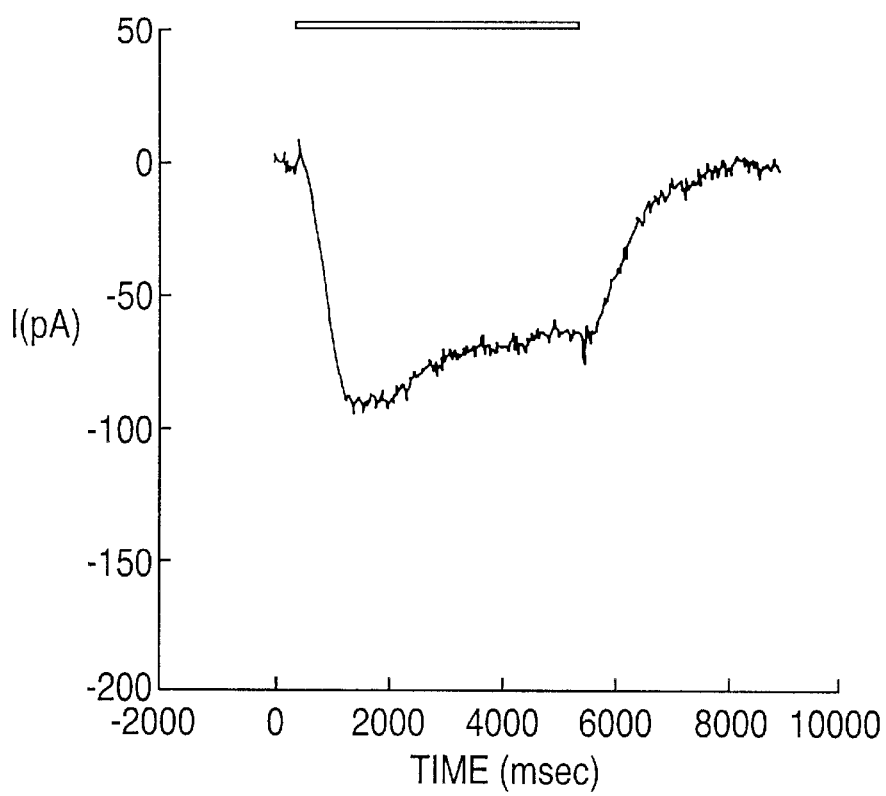
FIG. 8D Heteromeric: block by Mg2+
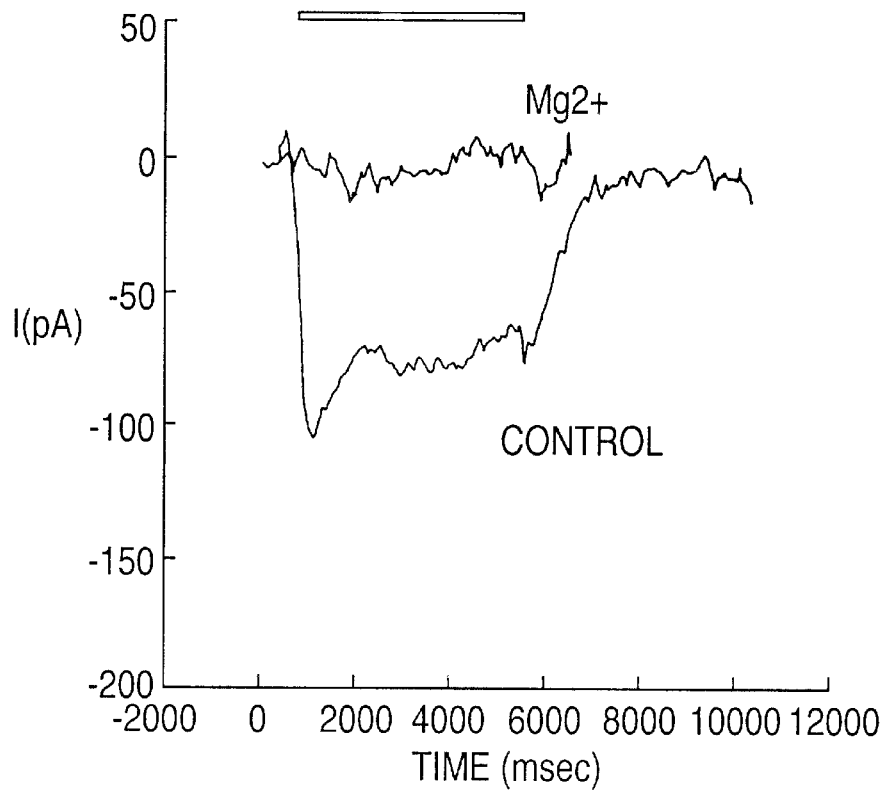

HUMAN NR2A BINDING ASSAY

CROSS REFERENCE TO RELATED APPLICATIONS

This application is a continuation-in-part of United States patent application Ser. No. 07/987,953, filed Dec. 11, 1992, now abandoned.

FIELD OF THE INVENTION

This invention relates to the application of recombinant DNA technology in the field of neurobiology. More particularly, the invention relates to the cloning and expression of DNA coding for proteins which modulate the function of glutamate receptors.

BACKGROUND TO THE INVENTION

In the mammalian central nervous system (CNS), the transmission of nerve impulses is controlled by the interaction between a neurotransmitter substance released by the "sending" neuron which then binds to a surface receptor on the "receiving" neuron, to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Members of the EAA receptor family can be grouped into three main types based on differential binding to certain glutamate analogs. One type of EAA receptor, which in addition to glutamate also binds the compound NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate (2-carboxy-4-(1-methylethenyl)-3-pyrrolidineacetate). Accordingly, receptors which bind glutamate but not NMDA and which bind with greater affinity to kainate than to AMPA, are referred to as kainate-type EAA receptors. Similarly, those EAA receptors which bind glutamate but not NMDA, and which bind AMPA with greater affinity than kainate are referred to as AMPA-type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. The development of therapeutics which modulate these processes is being slowed by the lack of any homogeneous source of receptor material with which to discover selectively binding drug molecules, which interact specifically at the interface of an appropriate EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor cDNA, a substrate which is homogeneous for the desired receptor is provided, for drug screening programs.

Non-human cDNAs which appear to encode the NMDA-type of EAA receptor have recently been identified and isolated. A cDNA encoding a subunit polypeptide of an NMDA receptor in rat, designated NR1, has been isolated as described by Moriyoshi et al. in Nature 354: 31, 1991. An extension of this work has revealed seven isoforms of NR1, presumably generated by combinations of alternative RNA splicing in the amino- and carboxy-terminal regions of NR1 (Anantharam et al. FEBS Lett. 305: 27, 1992; Durand et al. Proc. Natl. Acad. Sci. USA 89: 9359, 1992; Nakanishi et al. Proc. Natl. Acad. Sci. USA 89: 8552, 1992; Sugihara et al. Biochem. Biophys. Res. Commun. 185: 826, 1992; Hollmann et al. Neuron 10: 943, 1993; Kusiak and Norton. Mol. Brain. Res. 20: 64, 1993). DNA encoding NR1 and one of its isoforms have also been cloned from mouse brain by Yamazaki et al. as described in FEBS Lett. 300: 39, 1 992. Other rat NMDA receptor subunits, designated NR2A, NR2B, NR2C and NR2D, have also been identified (Monyer et al. Science 256: 1217, 1992; Ishii et al. J. Biol. Chem. 268: 2836, 1993), as well as mouse NMDA receptor subunits which have been designated $\epsilon 1$, $\epsilon 2$, $\epsilon 3$ and $\epsilon 4$ (Meguro et al. Nature 357: 70, 1992; Kutsuwada et al. Nature 358: 36, 1992; Ikeda et al. FEBS Lett. 313: 34, 1992).

There has emerged from these molecular cloning advances, a better understanding of the structural features of NMDA receptors and their subunits, as they exist in the non-human brain. According to the current model, each NMDA receptor is heteromeric, consisting of individual membrane-anchored subunits, each comprising transmembrane regions and extracellular domains that dictate ligand-binding properties and contribute to the ion-gating function served by the receptor complex.

In the search for therapeutics useful to treat CNS disorders in humans, it is highly desirable to obtain knowledge of human EAA receptors, and proteins which modulate the activity of these receptors. Such an understanding would provide a means to screen for compounds that selectively interact with this activity, i.e. to stimulate or inhibit receptor activity, thereby providing a means to identify compounds having potential therapeutic utility in humans. Non-human mammalian models are not suitable for this purpose despite significant protein homology due to the fact that minute sequence discrepancies have been found to cause dramatic pharmacological and functional variation between species homologues of the same protein (Oksenberg et al., Nature, 360:1 61, 1992; Hall et al. Trends Pharmacol. Sci. 14: 376, 1993). It is therefore particularly desirable to provide cloned cDNA encoding human EAA receptor proteins or modulatory proteins thereof, and cell lines expressing these proteins, in order to generate a screening method for compounds therapeutically useful in humans. These, accordingly, are objects of the present invention.

SUMMARY OF THE INVENTION

Human cDNAs encoding a family of NMDA receptor modulatory proteins have been identified and characterized. This family of modulatory proteins, herein referred to as the human NR2A modulatory protein family, comprises a parent protein, designated the human NR2A-1 protein, as well as functional sequence-related variants of the human NR2A-1 protein and functional fragments of the NR2A-1 protein.

In one of its aspects, thus, the present invention provides an isolated polynucleotide, consisting either of DNA or of RNA, which codes for a human NR2A protein, or functional fragments thereof.

In another aspect of the present invention, there is provided a cell that has been genetically engineered to produce a human EAA receptor modulatory protein belonging to the herein-defined NR2A family. In related aspects of the present invention, there are provided recombinant DNA constructs and methods useful to obtain substantially homogeneous sources of the human NR2A protein, comprising the steps of culturing the genetically engineered cells, and then recovering the cultured cells.

In another aspect of the present invention, there is provided a method for evaluating interaction between a candidate ligand and a human EAA receptor modulatory protein, which comprises the steps of incubating the candidate ligand with a genetically engineered cell as described above, or with a membrane preparation derived therefrom, and then assessing said interaction by determining the extent of protein/ligand binding, or by determining the ligand-induced electrical current across said cell.

In yet another aspect of the present invention, a cell that has been engineered genetically to produce a human heteromeric NR2A/receptor complex comprising an NR2A protein and an NMDA receptor subunit is provided.

In a further aspect of the present invention, there is provided a method for evaluating interaction between a candidate ligand and a human heteromeric ; NR2A/receptor complex comprising an NR2A protein and an NMDA receptor subunit, said method comprising the steps of incubating the candidate ligand with a cell line engineered to produce said receptor complex, or with a membrane preparation derived therefrom, and then assessing the interaction therebetween by determining the extent of protein/ligand binding, or by determining the ligand-induced electrical current across said cell.

Other aspects of the present invention include a human NR2A protein, in a form essentially free from other proteins of human origin, functional and immunogenic fragments of the protein, antibodies which bind to the protein, and oligonucleotides which hybridize to nucleic acid encoding the protein.

Other aspects of the present invention, which encompass various applications of the discoveries herein described, will become apparent from the following detailed description, and from the accompanying drawings in which:

BRIEF REFERENCE TO THE DRAWINGS

Figure 2B:
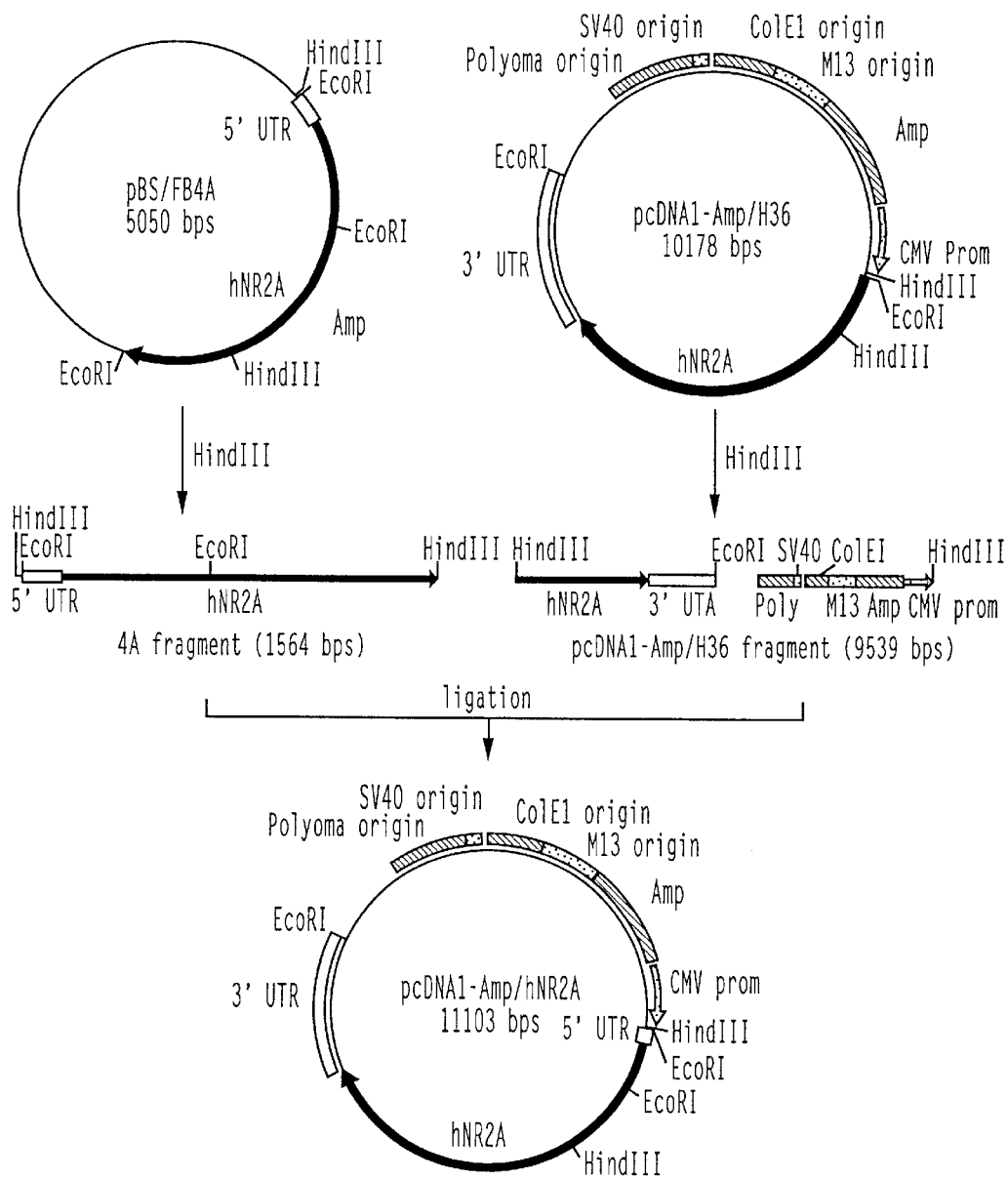

FIGS. 1A–1Q provide the nucleotide sequence (SEQ ID NO: 1) of DNA encoding an EAA receptor modulatory protein according to the present invention, and the deduced amino acid sequence (SEQ ID NO: 2) thereof;

FIGS. 2A and 2B illustrate, with plasmid maps, the strategy used to construct expression vectors harbouring DNA sequence illustrated in FIGS. 1A–1Q (SEQ ID NO: 1);

FIG. 3 provides, with reference to FIGS. 1A–1Q (SEQ ID NO: 1and 2), the partial DNA and amino acid sequences (SEQ ID NOs: 5 & 6) of a naturally occurring variant of the modulatory protein illustrated in FIGS. 1A–1Q (SEQ ID NO: 2);

FIGS. 4A–4L provide the nucleotide sequence (SEQ ID NO: 9and 10) of DNA encoding the NMDAR1-1 receptor;

FIGS. 5A and 5B provide a comparison of partial nucleotide sequences of NMDAR1-1 (SEQ ID NO: 11) with its variants, NMDAR1-2, NMDAR1-3A and NMDAR1-3C (SEQ ID NOs: 12, 13 & 14, respectively);

FIG. 6 provides a comparison of the amino acid sequences of NMDAR1-1 (SEQ ID NO: 17) and NMDAR1-4 (SEQ ID NO: 18);

FIG. 7 provides a comparison of the amino acid sequences of NMDAR1-1/2/3/4 (SEQ ID NO: 19) and NMDAR1-5/6/7/8 (SEQ ID NO: 20); and FIGS. 8A–8D graphically illustrate electrophysiological properties of a heteromeric complex comprising NR2A-1 and NMDAR1-3C.

DETAILED DESCRIPTION OF THE INVENTION AND ITS PREFERRED EMBODIMENTS

The present invention relates to modulatory proteins of excitatory amino acid (EAA) receptors of human origin, and to isolated polynucleotides encoding them. More particularly, the present invention is directed to a novel family of human modulatory proteins, herein designated the human NR2A EAA receptor modulatory protein family, which modulate the activity of human EAA receptors of the NMDA-type. The NR2A family of modulatory proteins comprises the human NR2A-1 protein, the amino acid sequence of which is identified in FIG. 1 (SEQ ID NO: 2), as well as functional sequence-related variants of the human NR2A-1 protein and functional fragments of the NR2A-1 protein.

As used herein, the term "modulatory protein" refers to a protein that, when combined with a human EAA receptor, and in particular with a human NMDA receptor, forms a heteromeric receptor complex having electrophysiological properties which are distinct from the electrophysiological properties of a homomeric receptor complex formed from the selected NMDA receptor alone. Thus, the NR2A proteins of the present invention have been found to modulate the ion channel activity of NMDA-type receptors also know as NMDA-type receptor subunits, i.e. receptors having a ligand binding profile comprising specific binding affinity for glutamate, NMDA and MK-801 [(+)-5-methyl-10,11-dihydro-5H-dibenzo[a,d]cyclohepten-5,10-imine maleate]. The electrophysiological properties, or ion channel activity, of EAA receptors is typically determined using established electrophysiological assays appropriate for detecting conductance across a cell membrane such as the assay described by Hollmann et al. in Nature 342: 643.

The term "isolated" as it is used herein with respect to NR2A-encoding polynucleotides refers to polynucleotides which are free from human DNA which encodes, or partially encodes, CNS proteins other than NR2A proteins and NMDA receptor proteins.

The term "heteromeric NR2A/receptor complex" is used to refer to a receptor complex comprising a modulatory NR2A protein, in accordance with the present invention, and an NMDA receptor.

Variants of the NR2A parent modulatory protein also form members of the family of human NR2A modulatory proteins as defined above and include functional variants of the human NR2A-1 protein which exhibit a modulatory activity similar to that of the NR2A-1 protein, and which demonstrate substantial sequence homology to the NR2A-1 protein, i.e. share greater than 96% amino acid identity with the NR2A-1 protein. Variants of the NR2A-1 protein include both naturally occurring variants, an example of which is the NR2A-2 protein, illustrated in part in FIG. 3 by nucleic acid and amino acid sequence (SEQ ID NOs: 5 & 6), as well as synthetically derived variants of the human NR2A-1 protein.

The term "fragment" is used herein to denote functional segments of an NR2A protein.

Variants and fragments of the NR2A proteins are said to be "functional" if, on coexpression with an NMDA receptor in a heteromeric NR2A/receptor complex as defined above, the complex, when assayed electrophysiologically, exhibits ligand-induced ion channel activity having measurable current, i.e. current which is greater than the current in the absence of the ligand or greater than the "baseline" current, and the channel activity possess properties which are characteristic of an NMDA ion channel, for example the channel activity is blocked by $Mg^{++}$ ions and by MK-801.

Each of the naturally occurring members of the human NR2A modulatory protein family possess structural features similar to those of EAA receptors, including an extracellular amino-terminal (N-terminal) region, as well as internal hydrophobic domains which serve to anchor the protein within the cell surface membrane. The particular human EAA receptor modulatory protein designated NR2A-1 is a protein characterized structurally as a single polypeptide chain that is produced initially in precursor form bearing an N-terminal signal peptide, and is transported to the cell surface in mature form, lacking the signal peptide. The NR2A-1 protein, including its signal peptide, consists of 1,464 amino acids arranged in the sequence illustrated by single letter code, in FIGS. 1A–1Q (SEQ ID NO: 2).

A naturally occurring structurally-related variant of the NR2A-1 protein has also been identified and is designated herein, the NR2A-2 modulatory protein. This variant protein differs from its NR2A-1 parent by a single amino acid as illustrated in FIG. 3. Specifically, the lysine residue at position 270 in NR2A-1 is a glutamic acid residue in the NR2A-2 variant. This change is reflected as a single nucleotide difference between the nucleic encoding the two proteins, namely a codon change from "AAA" in NR2A-1 to "GAA" in NR2A-2.

Like other members of the human NR2A family, the NR2A-1 protein is characterized by its modulatory activity particularly with respect to human NMDA-type receptors, and more particularly with respect to NMDA receptors of the NMDAR1 family, which are described in detail in co-pending U.S. patent application. Ser. No. 07/987,953, the content of which is incorporated herein by reference. The NMDAR1 family of EAA receptors comprises the NMDAR1-1 receptor, the nucleic acid sequence of which is illustrated in FIGS. 4A-4L (SEQ ID NO: 9), and variants of the NMDAR1-1 receptor which retain an NMDA-type ligand binding profile and which are structurally related to NMDAR1-1, i.e. share at least 99.6% amino acid identity with the 1-845 amino acid region of the NMDAR1-1 receptor, and preferably share 100% amino acid identity in this region. There are both naturally occurring and synthetically derived variants of the human NMDAR1-1 receptor. Naturally occurring varients include, but are ;not restricted to, receptor variants designated human NMDAR1-2, NMDAR1-3A and NMDAR1-3C, the partial nucleotide sequences of which are illustrated in FIGS. 5A and 5B (SEQ ID Nos: 11, 12, & 13, respectively) and compared to the nucleotide sequence of NMDAR1-1 (SEQ ID NO: 10). Another variant, designated NMDAR1-3B, differs in amino acid sequence from the NMDAR1-1 and NMDAR1-3C receptors by a single amino acid at position 470. This amino acid is lysine in NMDAR1-3B and is glutamic acid in NMDAR1-1 and NMDAR1-3C. This change results from a single base pair change in the codon at position 2560 of NMDAR1-1 and NMDAR1-3C from GAG to AAG in the 3B variant. An NMDAR1-4 variant differs from the NMDAR1-1 receptor by a peptide insert between amino acids 845 and 846 of NMDAR1-1 as illustrated in FIG. 6. Further variants include NMDAR1-5, NMDAR1, NMDAR1-7 and NMDAR1-8, which correspond respectively to NMDAR1-1, NMDAR1-2, NMDAR1-3 and NMDAR1-4 receptors additionally including a 21 amino acid insert as illustrated in FIG. 7.

One of skill in the art will appreciate that variants of any one of the NMDAR1-1 to NMDAR1-8 receptors which include minor variations from the amino acid sequences thereof, e.g. 1 to 6 amino acid substitutions, deletions or additions, and resulting in receptors retaining the ligand binding profile characteristic of NMDA-type receptors, are also encompassed within the NMDAR1 family of receptors.

Accordingly, the NR2A proteins of the present invention are useful in a heteromeric structure to screen for candidate compounds having the ability to alter the activity of the heteromeric NR2A/receptor complex. In addition, and despite the understanding that the NR2A family of proteins require a heteromeric structure to function in a modulatory sense, cells producing an NR2A protein homomerically, independent of association with an NMDA receptor, can be exploited for the purpose of screening candidate ligands for the ability to interact specifically therewith. Those compounds found to interact with an NR2A protein represent potential drug compounds which may have agonist or antagonist properties useful in the treatment of neurological disease conditions.

For use in assessing interaction between an NR2A protein, either in homomeric or heteromeric form, and a candidate compound, it is desirable to construct by application of genetic engineering techniques a cell that produces a human NR2A receptor in functional form as a heterologous product. The construction of such cell lines is achieved by introducing into a selected host cell a recombinant DNA construct in which DNA coding for a secretable form of the human NR2A protein, i.e. a form bearing either its native signal peptide or a functional, heterologous equivalent thereof, is associated with expression controlling elements that are functional in the selected host to drive expression of the NR2A-encoding DNA, and thus elaborate the desired NR2A protein. Such cells are herein characterized as having the protein-encoding DNA incorporated "expressibly" therein. The protein-encoding DNA is referred to as "heterologous" with respect to the particular cellular host if such DNA is not naturally found in the particular host.

It is most desirable to use a mammalian cell host to produce the present NR2A modulatory proteins due to their human origin; however, other suitably engineered eukaryotic and prokaryotic hosts may also be employed to produce NR2A proteins. Accordingly, bacterial hosts such as *E. coli* and *B. subtilis*, fungal hosts such as Aspergillus and yeast and insect cell hosts such as *Spodoptera frugiperda*, are examples of non-mammalian hosts that may also be used to produce NR2A proteins of the present invention.

The particular cell type selected to serve as host for production of the human NR2A protein can be any of several cell types currently available in the art. Preferably, where the NR2A protein will be expressed in heteromeric form, i.e. in conjunction with an NMDA receptor, the cell type selected will not be one which in its natural state elaborates a surface receptor that has ion channel activity or that elaborates a protein that is capable of modulating receptor activity, so as to confuse the assay results sought from the engineered cell line. Generally, such problems are avoided by selecting as host a non-neuronal cell type. However, neuronal cells may nevertheless serve as expression hosts, provided that any "background" activity is accounted for in the assay results.

According to one embodiment of the present invention, the cell line selected to serve as host for NR2A protein production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available. Any one of these systems can be exploited to drive expression of NR2A-encoding DNA. These systems, available typically in the form of plasmidic vectors, incorporate expression cassettes, the functional components of which include DNA constituting host-recognizable expression controlling sequences which enable expression of the receptor-encoding DNA when linked 5' thereof. The systems further incorporate DNA sequences which terminate expression when linked 3' of the protein-encoding region. Thus, for expression in a selected mammalian cell host, there is generated a recombinant DNA expression construct in which DNA encoding an NR2A protein is linked with expression controlling DNA sequences recognized by the host, including a region 5'of the NR2A-encoding DNA to drive expression, and a 3' region to terminate expression. The plasmidic vector harbouring the expression construct typically incorporates such other functional components as an origin of replication, usually virally-derived, to permit replication of the plasmid in the expression host, including bacterial hosts such as $E.\ coli$. To provide a marker enabling selection of stably transfected recombinant cells, the vector will also incorporate a gene conferring some survival advantage on the transfectants, such as a gene coding for neomycin resistance in which case the transfectants are plated in medium with neomycin.

Included among the various recombinant DNA expression systems that can be used to achieve mammalian cell expression of the NR2A-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the long terminal repeat (LTR) of retroviruses, insect cell promoters such as those regulated by temperature, and isolated from Drosophila, as well as mammalian gene promoters such as steroid-inducible promoters and those regulated by heavy metals i.e. the metalothionein 10 gene promoter. In order to achieve expression in bacterial hosts, such as $E.\ coli$, expression systems that exploit the expression controlling regions of various $E.\ coli$ and viral genes can be used to drive NR2A production including the lac gene, the trp gene, and regions of the lambda genome ($P_L$ and $P_R$). Expression in yeast can be achieved using the expression-controlling regions of genes such as alcohol dehydrogenase and melibiase, and in Aspergillus, the expression-controlling regions of genes such as alcohol dehydrogenase and glucoamylase may be used. The expression controlling-regions of baculovirus may be used in the case of insect host cells.

For incorporation into the recombinant DNA expression vector, DNA coding for the desired NR2A protein, e.g. the NR2A-1 protein or a variant of the NR2A-1 protein, can be obtained by applying selected techniques of gene isolation or gene synthesis. As described in more detail in the examples herein, the NR2A-1 protein, and naturally occurring variants thereof, are encoded within the human genome, expressed in human brain tissue, and can therefore be obtained by careful application of conventional gene isolation and cloning techniques. This typically will entail extraction of total messenger RNA from a fresh source of human brain tissue, such as cerebellum, hippocampus or fetal brain tissue, followed by conversion of messenger RNA to cDNA and formation of a library in, for example, a bacterial plasmid, or more typically a bacteriophage. Bacteriophage harbouring fragments of the human DNA are typically grown by plating on a lawn of susceptible $E.\ coli$ bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled nucleotide probe of appropriate sequence to identify the particular phage colony carrying NR2A-encoding DNA of interest. Typically, the gene or a portion thereof so identified is subcloned into a plasmidic vector for nucleic acid sequence analysis.

Having herein provided the nucleotide sequence of human NR2A modulatory proteins, it will be appreciated that automated techniques of gene synthesis and/or amplification can also be performed to generate DNA coding therefor. Because of the length of NR2A-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly using polymerase chain reaction (PCR) technology as generally described by Barnett et al. in Nucl. Acids Res. 18:3094, 1990.

The application of automated gene synthesis techniques provides an opportunity to generate sequence variants of naturally occurring members of the NR2A gene family. It will be appreciated, due to the degeneracy associated with nucleotide triplet codons, that variant polynucleotides coding for the NR2A receptors herein described can be generated by substituting synonymous codons for those represented in the naturally occurring,polynucleotide sequences herein identified, such as those identified in FIGS. 1A–1Q (SEQ ID NO: 1) and FIG. 3 (SEQ ID NO: 4). For example, as would be known by one of skill in the art, arginine may be encoded by any one of six codons selected from CGA, CGC, CGG, CGU, AGA and AGG, threonine may be encoded by any one of four codons selected from ACA, ACC, ACG and ACU, while lysine is encoded by two codons, AAA and AAG. In addition, polynucleotides coding for synthetic variants of the NR2A receptors can be generated which, for example, incorporate one or more, e.g. 1–10, single amino acid substitutions, deletions or additions. Since it will for the most part be desirable to retain the modulatory activity of the NR2A protein for screening purposes, it is desirable to limit amino acid substitutions to those regions which are less critical for modulatory activity as may be elucidated upon domain mapping of the protein. Such substitutions may include, for example, conservative amino acid substitutions such as isoleucine to leucine, or lysine to arginine.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt-ended, amplified DNA fragments, or preferentially via step-wise ligation of fragments containing naturally occurring restriction endonuclease sites. In this application, it is possible to use either CDNA or genomic DNA as the template for the PCR amplification. In the former case, the cDNA template can be obtained from commercially available or self-constructed cDNA libraries of various human brain tissues, including hippocampus and cerebellum.

Once obtained, the NR2A-encoding DNA is incorporated for expression into any suitable expression vector using conventional procedures, and host cells are transfected therewith also using conventional procedures which include, for example, DNA-mediated transformation, electroporation, microinjection, or particle gun transformation. Expression vectors may be selected to provide transfected mammalian cell lines that express the NR2A-encoding DNA either transiently or in a stable manner. For transient expression, host cells are typically transfected with an expression vector harbouring an origin of replication functional in a mammalian cell. For stable expression, such replication origins are unnecessary, but the vectors will typically harbour a gene coding for a product that confers on the transfectants a survival advantage, to enable their selection. Genes coding for such selectable markers include, but are not limited to, the *E. coli* gpt gene which confers resistance to mycophenolic acid, the neo gene from transposon Tn5 which confers resistance to the antibiotic G418 and to neomycin, the dhfr sequence from murine cells or *E. coli* which changes the phenotype of DHFR(−) cells into DHFR(+) cells, and the tk gene of herpes simplex virus, which makes TK(−) cells phenotypically TK(+) cells. Both transient expression and stable expression can provide transfected cell lines, and membrane preparations derived therefrom, for use in screening assays.

The recombinant techniques described above can be equally applied to EAA receptor production, in particular NMDA receptor production, as set out in the specific examples described herein and using, for example the DNA sequences provided in FIGS. 4A–4L (SEQ ID NO: 9)and 5A and 5B (SEQ ID NO: 11, 12, 13 and 14, respectively in the preparation cells which heteromerically produce an NR2A modulatory protein and an NMDA receptor. In this case, once the appropriate NR2A-encoding and NMDA receptor-encoding expression vectors have been prepared, the cells selected for expression are transfected with a mixture of the NR2A-encoding and NMDA receptor-encoding expression vectors in the conventional manner.

For use in screening assays, cells transiently expressing the NR2A-encoding DNA, and the NMDA receptor-encoding DNA, can be stored frozen for later use, but because the rapid rate of plasmid replication will lead ultimately to cell death, usually in a few days, the transfected cells should be used as soon as possible. Such assays may be performed either with intact cells, or with membrane preparations derived from such cells. The membrane preparations typically provide a more convenient substrate for the ligand screening experiments, and are therefore preferred as substrates. To prepare membrane preparations for screening purposes, i.e. ligand binding experiments, frozen intact cells are homogenized while in cold water suspension and a membrane pellet is collected after centrifugation. The pellet is re-suspended and re-centrifuged to remove endogenous ligands that would otherwise compete for binding in the assays. The membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a candidate ligand to a selected human NR2A protein of the invention, or a heteromeric NR2A/receptor complex comprising an NR2A protein and an NMDA receptor, is evaluated typically using a predetermined amount of cell-derived membrane (measured for example by protein determination), generally from about 25 ug to 100 ug. Competitive binding assays will be useful to evaluate the affinity of a candidate ligand for a heteromeric complex relative to glutamate. This competitive binding assay can be performed by incubating a membrane preparation with radiolabelled glutamate, for example [$^3$H]-glutamate, in the presence of unlabelled candidate ligand added at varying concentrations. Following incubation, either displaced or bound radiolabelled glutamate can be recovered and measured to determine the relative binding affinities of the candidate ligand and glutamate for the particular receptor used as substrate. In this way, the affinities of various compounds for the heteromeric complex can be measured. As will be appreciated by one of skill in the art, binding assays such as radioimmunoassays and ELISA can also be used to determine binding affinity of a candidate ligand. Such competitive binding assays cannot be used in the case of an NR2A protein which is expressed homomerically, in a state that does not naturally bind those ligands bound by EAA receptors. Thus, the binding affinity of candidate ligands for the NR2A protein can be determined using a conventional non-competitive type binding assay. Those ligands determined to have an appropriate affinity for the homomeric NR2A protein, i.e. a binding affinity in the micromolar range, and more preferably in the nanomolar range, can then be selected to determine if their binding is specific, and further, if their binding affects the pharmacological and functional characteristics of a heteromeric NR2A/receptor complex.

The NR2A proteins of the present invention are functional in a modulatory context, forming heteromeric NR2A/receptor complexes, comprising a human NR2A protein and an EAA receptor, which exhibit electrophysiological properties that are distinct from those exhibited by the NR2A protein and NMDA receptor components of the complex. The NR2A proteins are therefore useful, in the established manner, for screening candidate ligands for their ability to modulate the ion channel activity of such NR2A/receptor heteromeric complexes. The present invention thus further provides, as a ligand screening technique, a method of detecting interaction between a candidate ligand and a human NR2A/receptor heteromeric complex, comprising the steps of incubating the candidate ligand with a cell that produces a human NR2A/receptor heteromeric complex, or with a membrane preparation derived therefrom, and then measuring the ligand-induced electrical current across said cell or membrane.

As an alternative to using cells that express the NR2A protein, either homomerically or as a heteromeric receptor complex, ligand characterization may also be performed using cells (for example *Xenopus oocytes*), that yield functional membrane-bound protein following introduction of messenger RNA coding for the NR2A protein, in the case of homomeric expression, or coding for a heteromeric NR2A/ receptor complex, in the case of heteromeric expression. Thus, NR2A DNA is typically subcloned into a plasmidic vector such that the introduced DNA may be easily transcribed into RNA via an adjacent RNA transcription promoter supplied by the plasmidic vector, for example the T3 or T7 bacteriophage promoters. RNA is then transcribed from the inserted gene in vitro, and isolated and purified therefrom for injection into Xenopus oocytes. In the case of a heteromeric NR2A/receptor complex, the RNA of the NMDA receptor forming the complex is prepared in the same manner for injection into Xenopus oocytes simultaneously with the NR2A RNA. Following the injection of nanoliter volumes of an RNA solution, the oocytes are left to incubate for up to several days, and are then tested for the ability to respond to a particular ligand molecule supplied in a bathing solution. In the heteromeric case, due to the fact that an active membrane channel is formed through which ions may selectively pass, the response of a particular ligand molecule in the bathing solution may typically be measured as an electrical current utilizing microelectrodes inserted into the cell or placed on either side of a cell-derived membrane preparation using the "patch-clamp" technique.

In addition to using the NR2A-encoding DNA to construct cell lines useful for ligand screening, expression of the DNA can, according to another aspect of the invention, be performed to produce fragments of the protein in soluble form, for structure investigation, to raise antibodies and for other experimental uses. It is therefore desirable in the first instance to facilitate the characterization of particular regions of NR2A in quantity and in isolated form, i.e. free from the remainder of the NR2A protein. One region of particular interest with regard to the modulatory function of the NR2A protein is the extracellular N-terminal region. To prepare a fragment of the N-terminal region, the full-length NR2A-encoding DNA may be modified by site-directed mutagenesis, to introduce a translational stop codon into the extracellular N-terminal region, immediately 5' of the first transmembrane domain (TM1). Since there will no longer be produced any transmembrane domain(s) to "anchor" the protein into the membrane, expression of the modified cDNA will result in the secretion, in soluble form, of only the extracellular N-terminal domain. Standard ligand-binding assays may then be performed to ascertain the degree of binding of a candidate compound to the extracellular domain so produced. Alternatively, a translational stop codon may be introduced downstream of the first transmembrane domain to yield a fragment which retains the ability to anchor into the cell membrane. In this way, a heteromeric channel comprising the N-terminal NR2A fragment can be formed and used to determine the extent of modulatory activity possessed by the fragment. It may of course be necessary, using site-directed mutagenesis, to produce different versions of this extracellular region, or indeed any other extracellular region of NR2A, in order to map the modulatory domain with precision.

Alternatively, it may be desirable to produce other regions. of the NR2A protein, for example all or part of the carboxy-terminus thereof. In this case, site-directed mutagenesis and/or PCR-based amplification techniques may readily be used to provide a defined fragment of the CDNA encoding the domain of interest.

Once obtained, such DNA fragments can be expressed in the usual manner, either homomerically to determine if the fragment has ligand-binding activity, or heteromerically to determine the extent to which the fragment retains NR2A modulatory activity. Conventional peptide synthetic techniques may also be used to make the desired C-terminal fragments or other fragments, e.g. a desired N-terminal fragment as noted above.

It will be appreciated that the production of NR2A fragments may be accomplished in a variety of host cells. Mammalian cells such as CHO cells may be used for this purpose, the expression typically being driven by an expression promoter capable of high-level expression, for example, the CMV promoter. Alternately, non-mammalian cells, such as insect Sf9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of selected domains of the NR2A protein. *Aspergillus nidulans* for example, with the expression being driven by the alcA promoter, would constitute such an acceptable fungal expression system. In addition to such expression hosts, it will be further appreciated that any prokaryotic or other eukaryotic expression system capable of expressing heterologous genes or gene fragments, whether intracellularly or extracellularly, would be similarly acceptable.

For use particularly in detecting the presence and/or location of an NR2A protein, for example in brain tissue, the present invention also provides, in another of its aspects, antibodies to a human NR2A protein. Such antibodies will also have use as diagnostic agents, e.g. to determine if localized amounts or different forms of NR2A in selected tissue types are indicative of a disease condition, and as therapeutic agents, by regulating the modulatory activity of an NR2A protein on an NMDA receptor ion channel, to prevent disease conditions associated with overactive NMDA receptor ion channels. Preferably, for use therapeutically, the NR2A antibodies employed are monoclonal antibodies.

To raise NR2A antibodies, there may be used as immunogen either the intact, soluble NR2A protein or an immunogenic fragment thereof, produced in a microbial or mammalian cell host as described above or by standard peptide synthesis techniques. Regions of the NR2A protein particularly suitable for use as immunogenic fragments include those corresponding in sequence to an extracellular region of the receptor, or a portion of the extracellular region, such as peptides consisting of residues 23–556, or fragments thereof.

The raising of antibodies to the desired NR2A protein or immunogenic fragment can be achieved, for polyclonal antibody production, using immunization protocols of conventional design, and any of a variety of mammalian hosts, such as sheep, goats and rabbits. For monoclonal antibody production, immunocytes such as splenocytes can be recovered from the immunized animal and fused, using hybridoma technology, to myeloma cells. The fusion cell products, i.e. hybridoma cells, are then screened by culturing in a selection medium, and cells producing the desired antibody are recovered for continuous growth, and antibody recovery. Recovered antibody can then be coupled covalently to a reporter molecule, i.e. a detectable label, such as a radiolabel, enzyme label, luminescent label or the like, optionally using linker technology established for this purpose.

In detectably labelled form, e.g. radiolabelled form, olignucleotides, including both DNA or RNA, coding for the human NR2A modulatory protein and selected regions thereof, may also be used, in accordance with another aspect of the present invention, as hybridization probes for example to identify sequence-related genes resident in the human or other mammalian genomes (or cDNA libraries) or to locate NR2A-encoding DNA in a specimen, such as brain tissue. This can be done using either the intact coding region, or a fragment thereof, having radiolabelled nucleotides, for example, $^{32}$P-labelled nucleotides, incorporated therein. To identify the NR2A-encoding DNA in a specimen, it is desirable to use either the full length cDNA coding therefor, or a fragment which is unique thereto. With reference to FIGS. 1A–1Q and the nucleotide numbering appearing thereon, such nucleotide fragments include those comprising at least about 17 nucleic acids which correspond in sequence to an extracellular region of NR2A DNA, e.g. the N-terminus thereof. Examples of suitable nucleotide fragments are the regions spanning nucleotides 8–1830 and 2673–6144 of NR2A-1. Such sequences, and the intact gene itself, may also be used of course to clone NR2A-related human genes, particularly cDNA equivalents thereof, by standard hybridization techniques.

Embodiments of the present invention are described in detail in the following specific Examples which should not be construed as limiting.

EXAMPLE 1

Isolation of DNA Coding for Human NR2A-1

A human NR2A DNA probe corresponding to a portion of nucleotide sequence of NR2A-1, namely the nucleotide region 1832–2361 as shown in FIGS. 1A-1Q, was generated by PCR-based amplification of recombinant bacteriophage lambda DNA isolated from an Eco RI-based bacteriophage lambda library of human hippocampus cDNA (obtained from Stratagene Cloning Systems, La Jolla, Calif.). The following degenerate oligonucleotide primers were used in the PCR amplification:
1) 5' GGGGTTTAGATCTGGGT-A/C/G/T-ATGATGTT-C/T-GT-A/C/G/T-ATG 3' (SEQ ID NO: 7); and
2) 5' GGGGTTTAGATCTGC-A/C/G/T-GC-A/G-TC-A/G-TA-A/G/T-AT-A/G-AA-A/G/C/T-GC 3' (SEQ ID NO: 8)

The primers were used at a final concentration of 2 pmol/μl each, in a 50 μl reaction volume (10 mM Tris-HCl, pH 9.0; 50 mM KCl; 1.5 mM MgCl$_2$) containing 100 ng of recombinant human hippocampus cDNA/bacteriophage lambda DNA, 5 units of *Thermus aquaticus* DNA polymerase (Promega, Madison, Wis.) and 0.2 mM of each deoxyribonucleotide. Thirty-five cycles of amplification proceeded, with denaturation at 95° C. for 1 min., annealing at 50° C. for 1 min., and primer extension at 72° C. for 1 min., followed by a final cycle at 72° C. for 5 min. The 554 bp PCR product was purified from an agarose gel and subcloned into the plasmid vector pT7Blue-T (Novagen, Madison, Wis.) for DNA sequencing.

The 554 bp human NR2A probe was radiolabeled with [a-$^{32}$P]dCTP using the Amersham Megaprime DNA labelling system (Arlington Heights, Ill.) to a specific activity of 1.0×10$^9$ cpm/μg. The labelled probe was used to screen approximately 1×10$^6$ plaques of the Eco RI-based human hippocampus cDNA/bacteriophage lambda Zap II library identified above and approximately 800,000 plaques of an Eco RI-based human fetal brain cDNA/bacteriophage lambda Zap II library (obtained from Stratagene). Nine positive plaques were identified on replica filters under the following hybridization conditions: 6×SSPE, 50% formamide, 0.5% SDS, 100 μg/ml denatured salmon sperm DNA at 42° C. with 1.85×10$^6$ cpm probe per ml hybridization fluid. The filters were washed twice with 2×SSPE, 0.5% SDS at 25° C. for 5 min., followed by a 15 min. wash at 42° C. The filters were exposed to X-ray film (Kodak, Rochester, N.Y.) overnight. The plaques were purified and excised as phagemids according to the supplier's specifications, to generate an insert-carrying Bluescript-SK variant of the phagemid vector.

DNA sequence analysis of the largest overlapping clones (isolated as pBS/FB4A and pBS/H36) revealed a putative ATG initiation codon together with about 155 nucleotides of 5' untranslated (UTR) information and 4,392 nucleotides of amino acid coding information. This analysis also revealed a termination codon as well as 1,590 nucleotides of 3' untranslated information. The entire DNA sequence of the NR2A-1 cDNA is provided in FIG. 1.

EXAMPLE 2

Isolation of DNA Coding for the Human NMDAR1-1 Receptor

A human NMDAR1 probe corresponding to a portion of nucleotide sequence of NMDAR1-1, namely the nucleotide region 2605–3213 as shown in FIGS. 4A–4L, was generated by PCR-based amplification of recombinant bacteriophage lambda DNA isolated from an Eco RI-based bacteriophage lambda library of human hippocampus cDNA (obtained from Stratagene Cloning Systems, La Jolla, Calif.). The following degenerate oligonucleotide primers were used in the PCR amplification:
1) 5' GGGGTTTGGATCCAA-A/G-GA-A/G-TGGAA-C/T-GGNATGATG 3' (SEQ ID NO: 15); and
2) 5' GGGGTTTAAGCTT-C/T-TC-G/A-TA-G/A-TT-G/A-TG-C/T-TT-C/T-TCCAT 3' (SEQ ID NO: 16)

The primers were used at a final concentration of 5 pmol/μl each, in a 50 μl reaction volume (10 mM Tris-HCl, pH 9.0; 50 mM KCl; 1.5 mM MgCl$_2$) containing 100 ng of recombinant human hippocampus cDNA/bacteriophage lambda DNA, 5 units of *Thermus aquaticus* DNA polymerase (Promega, Madison, Wis.) and 0.2 mM of each deoxyribonucleotide. Thirty-five cycles of amplification proceeded, with denaturation at 94° C. for 1 min., annealing at 51° C. for 1 min., and primer extension at 72° C. for 1 min., followed by a final cycle at 72° C. for 5 min. The 674 bp PCR product was purified from an agarose gel and subcloned into the plasmid vector pTZBlue-T (Novagen, Madison, Wis.) for DNA sequencing.

The 674 bp human NMDAR1 probe was radiolabelled with [a-$^{32}$P]dCTP using the Amersham Megaprime DNA labelling system (Arlington Heights, Ill.) to a specific activity of 1.0–2.4×10$^9$ cpm/ug. The labelled probe was used to screen approximately 400,000 plaques of an Eco RI-based human hippocampus cDNA/bacteriophage lambda Zap II library. Thirty-five positive plaques were identified on replica filters under the following hybridization conditions: 6×SSC, 50% formamide, 0.5% SDS, 100 ug/ml denatured salmon sperm DNA at 42° C. with 1.85×10$^6$ cpm probe per ml hybridization fluid. The filters were washed with 2×SSC, 0.5% SDS at 25° C. for 5 min., followed by 15 min. washes at 37° C. and at 42° C. The filters were exposed to X-ray film (Kodak, Rochester, N.Y.) overnight. Twenty-eight plaques were purified and excised as phagemids according to the supplier's specifications, to generate an insert-carrying Bluescript-SK variant of the phagemid vector.

DNA sequence analysis of the clone NMDAR1-3C revealed 2,814 nucleotides of amino acid coding information (938 amino acids). The entire DNA sequence of the EcoRI-EcoRI NMDAR1-3C cDNA insert is provided herein by reference to the sequence of NMDAR1-1 set out in FIGS. 4A–4L (SEQ ID NO: 9) and by reference to the sequence differences between NMDAR1-1 and NMDAR1-3C outlined in FIGS. 5A and 5B (SEQ ID NO: 11 and 14 respectivelly). The NMDAR1-3C cDNA was subcloned into the pcDNA1-Amp mammalian expression vector (to form pcDNA1-Amp/hNR1-3C) using standard techniques such as those described below in Example 3 for the subcloning of the NR2A clone into the pcDNA1-Amp vector.

It will be appreciated that the protocol described above can be used to isolate any of the NMDAR1 receptors in accordance with the present invention.

EXAMPLE 3

Construction of Genetically Engineered Cells Producinq a Heteromeric Complex of Human NR2A-1 and NMDAR1-3C For transient expression in mammalian cells, cDNA coding for human NR2A-1 was incorporated into the mammalian expression vector pcDNA1-Amp (Invitrogen Corporation, San Diego, Calif.). This is a multifunctional 5 kbp plasmid vector designed for cDNA expression in eukaryotic systems, and cDNA analysis in prokaryotes. Incorporated on the vector are the CMV immediate early gene promoter and enhancer sequences, SV40 transcription termination and RNA processing signals, SV40 and polyoma virus origins of replication, M13 and ColE1 origins, Sp6 and T7 RNA promoters, and a gene conferring ampicillin resistance. A polylinker is located appropriately downstream of the CMV and T7 promoters.

The strategy depicted in FIG. 2 was employed to facilitate incorporation of the NR2A-1 cDNA into the expression vector. The H36 cDNA insert was released from pBS/H36 as a 5.2 kbp EcoRI fragment, which was then incorporated at the EcoRI site in the pcDNA1-Amp polylinker. Restriction-endonuclease digestion and DNA sequence analysis across the junctions was performed to confirm proper insert orientation. The FB4A 5' 1.6 kbp HindIII fragment was released from pBS/FB4A and ligated with the 9.5 kbp HindIII fragment of pcDNA1-Amp/H36. Restriction-endonuclease digestion and DNA sequence analysis across the junctions was performed to confirm proper insert orientation. The resulting plasmid, designated pcDNA1-Amp/hNR2A, was then introduced for transient expression into a selected mammalian cell host, in this case human embryonic kidney cells of the HEK293 lineage (available from the American Type Culture Collection, Rockville, Md.; ATCC CRL 1573).

The 11.1 kbp plasmid designated pcDNA1-Amp/hNR2A carrying the NR2A-1 DNA as a 6.1 kbp insert in a 5 kbp pcDNA1-Amp plasmid background, was deposited, under the terms of the Budapest Treaty, with the American Type Culture Collection in Rockville, Md., USA on Mar. 16, 1994 and has been assigned accession number ATCC 75708.

For transient expression, HEK293 cells were transfected with approximately 2 µg DNA (as pcDNA 1-Amp/hNR2A or pcDNA 1-Amp/hNR 1-3C) per $10^5$ HEK293 cells, by lipofectin-mediated DNA transfection according to the manufacturer's (Life Technologies Inc., Gaithersburg, Md.) specifications. In coexpression experiments, i.e. for heteromeric expression of NR2A-1 and NMDAR1-3C, the HEK293 cells were similarly transfected with 3 µg of a DNA mixture containing pcDNA1-Amp/hNR2A and pcDNA1-Amp/hNR1-3C. Briefly, HEK293 cells were plated at a density of $10^5$ cells/dish and then grown for 24 hours in 10% FBS-supplemented MEM medium (Life Technologies Inc., Gaithersburg, Md.). The medium was then removed and cells were washed in OPTI-MEM I medium (Life Technologies Inc.) lacking FBS, prior to transfection. A transfection solution (100 µl) containing 5–7.5 µl of lipofectin and DNA was then applied to the cells. After incubation for 6 hours at 37° C., cells were washed as previously described and then allowed to grow for 36–48 hours in 10% FBS-supplemented MEM medium containing 50 µM DL-AP5 (2-amino-5-phosphonopentanoic acid) prior to electrophysiological recording.

In a like manner, stably transfected cell lines can also be prepared using various cell types as host: HEK293, CHO K1 or CHO Pro5. To construct these cell lines, cDNA coding for NR2A-1 is incorporated into the mammalian expression vector pRc/CMV (Invitrogen Corp., San Diego, Calif.) which enables stable expression. Insertion of the cDNA places it under the expression control of the CMV promoter and upstream of the polyadenylation site and terminator of the bovine growth hormone gene, and into a vector background comprising the neomycin resistance gene (driven by the SV40 early promoter) as selectable marker. To introduce plasmids constructed as described above, the host cells are first seeded at a density of $5\times10^5$ cells/dish in 10% FBS-supplemented MEM medium. After growth for 24 hours, fresh medium is added to the plates and three hours later, the cells are transfected using the lipofectin-mediated DNA transfection procedure according to the manufacturers specifications. Cells resistant to neomycin are selected in 10% FBS-supplemented MEM medium containing G418 (1 mg/ml). Individual colonies of G418-resistant cells are isolated about 2–3 weeks later, clonally selected and then propagated for assay purposes.

EXAMPLE 4

Electrophysiological Characterization

Standard whole-cell voltage-clamp (Axopatch 1B, Axon Instruments, Foster City, Calif.) techniques were used to record 100 µM NMDA-evoked currents in HEK293 cells transiently transfected as described in Example 3 and expressing hNR2A-1 heteromerically with the NMDAR1-3C receptor. The cells were rinsed prior to recording with a solution of 130 mM NaCl, 5.4 mM KCl, 1.8 mM $CaCl_2$, 10 µM glycine, 5 mM HEPES, pH 7.2 (300 mOsm.). Single electrode, voltage-clamp recordings were carried out using thin-walled borosilicate glass electrodes (WPI-TW150-F4, WPI Inc., Sarasota, Fla.) filled with an intracellular solution of 140 mM CsCl, 1 mM $MgCl_2$, 10 mM EGTA, 10 mM HEPES, pH 7.2 (adjusted with 1 M CsOH). NMDA application using a computer controlled array of perfusion barrels allowed for fast application and continuous perfusion with control or 1 mM $Mg^{2+}$-containing solutions (lag<50 milliseconds).

Figure 8A:
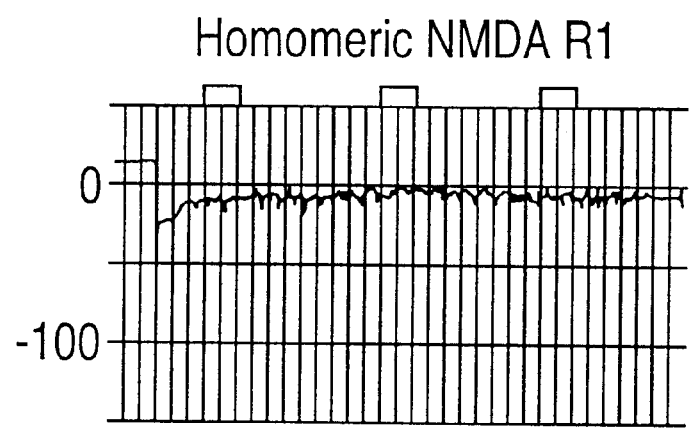
Figure 8B:
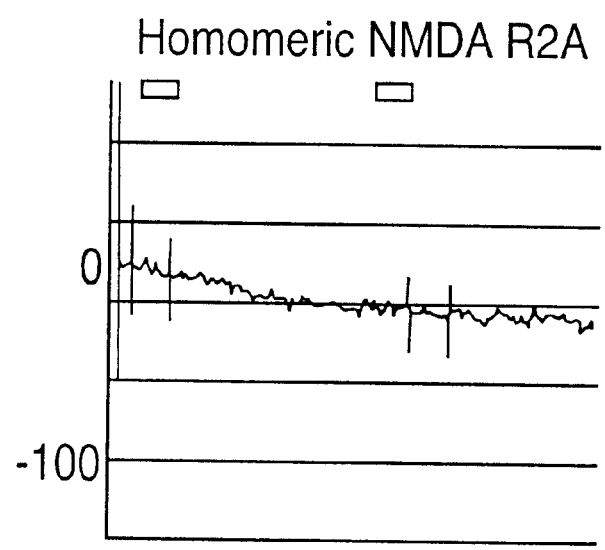

The results of the electrophysiological characterization are depicted in FIGS. 8A–8D. Points at which NMDA was applied are indicated with black bars above the recordings. No NMDA-induced depolarizations were observed in HEK293 cells transiently transfected with NMDAR1-3C alone (FIG. 8A) or with NR2A alone (FIG. 8B). NMDA-induced depolarizations were, however, observed in HEK293 cells transiently transfected with both NR2A and NMDAR1-3C (FIG. 8C). These latter currents were blocked by 1 mM $MgCl_2$, a result which is characteristic of NMDA-gated ion channels, as illustrated in FIG. 8D.

This electrophysiological characterization indicates that the NR2A/NMDA receptor heteromeric complex functions in an authentic manner, and can therefore be used to reliably predict the functional "signature" of its non-recombinant counterpart from intact human brain. These features make the recombinant receptor especially useful for selecting and characterizing ligand compounds which bind to or otherwise modulate the receptor, and/or for selecting and characterizing compounds which may act by displacing other ligands from the receptor. The isolation of the NR2A protein in a pure form, and its expression with an NMDA receptor as a single, homogenous complex, therefore frees the electrophysiological assay from the lack of precision introduced when complex receptor preparations from human and non-human brains are used to attempt such characterizations.

It will be appreciated that the protocol described above can be used to determine the electrophysiological characteristics of other NR2A/NMDA heteromeric receptor complexes, such as for example, the NR2A-1/NMDAR1-1 complex.

EXAMPLE 5

Ligand-binding Assays on Heteromeric NR2A-1/ NMDAR1-3C Complex

Frozen transfected cells, prepared as described in Example 3 above, are resuspended in ice-cold distilled water, sonicated for 5 seconds, and centrifuged for 10 minutes at 50,000×g. The supernatant is discarded and the membrane pellet is stored frozen at −70° C.

Cell membrane pellets are resuspended in ice cold 50 mM Tris-HCl, pH 7.55, and centrifuged again at 50,000×g for 10 minutes in order to remove endogenous glutamate that would otherwise compete for binding. The pellets are resuspended in ice cold 50 mM Tris-HCl, pH 7.55, and used for the binding experiments described below. Protein concentrations are determined using the Pierce reagent with BSA as an internal standard.

Binding assays are performed using a 25–100 µg protein equivalent of the ell membrane preparation, and a selected radiolabeled ligand. In particular, for MK-801-binding assays, incubation mixtures consist of 20 nM (+)-[3-$^3$H] MK-801 (30 Ci/mmole), 20, µM glycine, and 1 mM L-glutamate in cold incubation buffer (50 mM Tris-HCl, pH 7.55) at a final volume of 250 µl. Non-specific binding is determined in the presence of 1 mM (+)MK-801. For glutamate binding assays, incubation mixtures consist of 30 nM [3,4-$^3$H]-L-glutamate (47.3 Ci/mmole) in cold incubation buffer at a final volume of 250 µl. Non-specific binding is determined in the presence of 1 mM L-glutamate and displacement is determined in the presence of 1 mM NMDA, 1 mM kainate, or 1 mM AMPA. The reaction mixtures are incubated on ice for 60 minutes in plastic mini-vials. Bound and free ligand are separated by centrifugation for 30 minutes at 50,000×g. The pellets are washed three times in 4 ml of the cold incubation buffer, and then 4 ml of Beckman Ready-Protein Plus scintillation cocktail was added for liquid scintillation counting.

It will be appreciated that the protocol described above can be used to determine the pharmacological characteristics of other NR2A/NMDA heteromeric receptor complexes, such as for example, the NR2A-1/NMDAR1-1 complex.

EXAMPLE 6

Ligand-binding Assay for the Homomeric Expression of NR2A-1

Frozen transfected cells, prepared as described in Example 3 above and expressing NR2A-1 in the absence of an NMDA receptor, are resuspended in ice-cold distilled water, sonicated for 5 seconds, and centrifuged for 10 minutes at 50,000×g. The supernatant is discarded and the membrane pellet is stored frozen at −70° C.

Cell membrane pellets are resuspended in ice cold 50 mM Tris-HCl, pH 7.55, and centrifuged again at 50,000×g for 10 minutes in order to remove endogenous ligands that might otherwise compete for binding. The pellets are resuspended in ice cold 50 mM Tris-HCl, pH 7.55, and used for the binding experiments described below. Protein concentrations are determined using the Pierce reagent with BSA as an internal standard.

Binding assays are performed using a 25–100 µg protein equivalent of the cell membrane preparation, and a selected radiolabeled ligand in cold incubation buffer (50 mM Tris-HCl, pH 7.55) at a final volume of 250 µl. Non-specific binding is determined in the presence of the unlabeled ligand. The reaction mixtures are incubated on ice for 60 minutes in plastic mini-vials. Bound and free ligand are separated by centrifugation for 30 minutes at 50,000×g. The pellets are washed three times in 4 ml of the cold incubation buffer, and then 4 ml of Beckman Ready-Protein Plus scintillation cocktail are added for liquid scintillation counting.

Having determined that the selected ligand binds specifically to NR2A-1, i.e. that unlabelled ligand competes for binding with the labelled form of that ligand, and that the binding is saturable, the ligand is then tested for its ability to affect the heteromeric expression of NR2A-1, i.e. when coexpressed with an NMDA receptor as described above. Appropriate experiments for this purpose include the ligand binding experiment described in Example 5, and the electrophysiological characterization described in Example 4.

EXAMPLE 7

Isolation and Cloning of the NR2A-2 Variant

The procedures described in Examples 1 and 3 for isolating and cloning the NR2A-1 protein are applied equally for the isolation and cloning of NR2A-2 and other naturally occurring variants of NR2A-1, particularly in view of the high sequence homology between the NR2A-1 receptor and the NR2A-2 variant.

Moreover, the electrophysiological and ligand-binding assays described in Examples 4, 5 and 6, respectively, are used in the manner described to determine the electrophysiological and ligand binding characteristics of NR2A-2 and other NR2A-1 variants.

We claim:

1. A method of assaying a candidate ligand for binding interaction with a human NR2A protein, which comprises the steps of:
   (1) incubating the candidate ligand under appropriate conditions with a cell that has been mutated to produce a human NR2A protein,
      said cell having incorporated expressible therein a heterologous polynucleotide that encodes a modulatory protein selected from the group consisting of NR2A-1 having the amino acid sequence of SEQ ID NO:2 and NR2A-2 having the amino acid sequence of SEQ ID NO:2 wherein the lysine at position 270 is replaced by glutamic acid,
      or with a membrane preparation containing said NR2A protein, and then
   (2) determining the extent of binding between the human NR2A protein and the candidate ligand.

2. A method of assaying a candidate ligand for binding interaction with a human heteromeric receptor complex comprising an NR2A protein and an NMDAR1 receptor subunit, which comprises the steps of incubating the candidate ligand under appropriate conditions with a cell that has been engineered genetically to produce a heteromeric human receptor complex comprising an NR2A protein selected from the group consisting of:
   1. NR2A-1 having the amino acid sequence of SEQ ID NO:2; and
   2. NR2A-2 having the amino acid sequence of SEQ ID NO:2 wherein the lysine residue at position 270 is a glutamic acid residue,
   and an NMDAR1 receptor subunit selected from the group consisting of:
      (a) NMDAR1-1 having the amino acid sequence of SEQ ID NO:10;
      (b) NMDAR1-2 having the amino acid sequence of SEQ ID NO:21;
      (c) NMDAR1-3A having the amino acid sequence of SEQ ID NO:22;
      (d) NMDAR1-3C having the amino acid sequence of SEQ ID NO:23;
      (e) NMDAR1-3B having the amino acid sequence of SEQ ID NO:10 wherein residue 470 is a lysine residue;
      (f) NMDAR1-4 having the amino acid sequence of SEQ ID NO:24;
      (g) NMDAR1-5 having the amino acid sequence of SEQ ID NO:25;
      (h) NMDAR1-6 having the amino acid sequence of SEQ ID NO:26;
      (i) NMDAR1-7 having the amino acid sequence of SEQ ID NO:27; and
      (j) NMDAR1-8 having the amino acid sequence of SEQ ID NO:28.

3. A method of assaying a candidate ligand for binding interaction with a human heteromeric receptor complex comprising an NR2A protein and an NMDAR1 receptor subunit, which comprises the steps of:
   (1) incubating the candidate ligand under appropriate conditions with a cell that has been mutated to produce a heteromeric human receptor complex comprising:
      (i) an NR2A protein selected from the group consisting of NR2A-1 having the amino acid sequence of SEQ ID NO:2; and NR2A-2 having the amino acid sequence of SEQ ID NO:2 wherein the lysine at position 270 is replaced by glutamic acid, and
      (ii) an NMDAR1 receptor subunit selected from the group consisting of
         NMDAR1-1 having the amino acid sequence of SEQ ID NO:10,
         NMDAR1-2 having the amino acid sequence of SEQ ID NO:21,
         NMDAR1-3A having the amino acid sequence of SEQ ID NO:22,
         NMDAR1-3C having the amino acid sequence of SEQ ID NO:23,
         NMDAR1-3B having the amino acid sequence of SEQ ID NO:10 wherein the residue at position 470 is lysine,
         NMDAR1-4 having the amino acid sequence of SEQ ID NO:24,
         NMDAR1-5 having the amino acid sequence of SEQ ID NO:25,
         NMDAR1-6 having the amino acid sequence of SEQ ID NO:26,
         NMDAR1-7 having the amino acid sequence of SEQ ID NO:27, and
         NMDAR1-8 having the amino acid sequence of SEQ ID NO:28;
         or with a membrane preparation containing said NR2A protein and said NMDAR1 receptor subunit, and then
   (2) determining the extent of binding between the complex and the candidate ligand, or determining ligand-induced electrical current across said cell or membrane.

4. A method of assaying a candidate ligand according to claim 3, wherein said NMDAR1 receptor subunit is NMDAR1-1 having the amino acid sequence of SEQ ID NO:10.

5. A method of assaying a candidate ligand according to claim 3, wherein said NMDAR1 receptor subunit is NMDAR1-2 having the amino acid sequence of SEQ ID NO:21.

6. A method of assaying a candidate ligand according to claim 3, wherein said NMDAR1 receptor subunit is NMDAR1-3A having the amino acid sequence of SEQ ID NO:22.

7. A method of assaying a candidate ligand according to claim 3, wherein said NMDAR1 receptor subunit is NMDAR1-3C having the amino acid sequence of SEQ ID NO:23.

8. A method of assaying a candidate ligand according to claim 3, wherein said NMDAR1 receptor subunit is NMDAR1-3B having the amino acid sequence of SEQ ID NO:10 wherein the residue at position 470 is lysine.

9. A method of assaying a candidate ligand according to claim 3, wherein said NMDAR1 receptor subunit is NMDAR1-4 having the amino acid sequence of SEQ ID NO:24.

10. A method of assaying a candidate ligand according to claim 3, wherein said NMDAR1 receptor subunit is NMDAR1-5 having the amino acid sequence of SEQ ID NO:25.

11. A method of assaying a candidate ligand according to claim 3, wherein said NMDAR1 receptor subunit is NMDAR1-6 having the amino acid sequence of SEQ ID NO:26.

12. A method of assaying a candidate ligand according to claim 3, wherein said NMDAR1 receptor subunit is NMDAR1-7 having the amino acid sequence of SEQ ID NO:27.

13. A method of assaying a candidate ligand according to claim 3, wherein said NMDAR1 receptor subunit is NMDAR1-8 having the amino acid sequence of SEQ ID NO:28.

14. A method of assaying a candidate ligand according to claim 4, wherein said NR2A protein is NR2A-1 having the amino acid sequence of SEQ ID NO:2.

15. A method of assaying a candidate ligand according to claim 3, wherein said NR2A protein is NR2A-2 having the amino acid sequence of SEQ ID NO:2 wherein the lysine residue at position 270 is a glutamic acid residue.

* * * * *

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
      (A) LENGTH: 6151 base pairs
      (B) TYPE: nucleic acid
      (C) STRANDEDNESS: double
      (D) TOPOLOGY: linear (ii) MOLECULE TYPE: cDNA (ix) FEATURE:
    (A) NAME/KEY: CDS
    (B) LOCATION: 163..4554

(xi) SEQUENCE DESCRIPTION: SEQ ID NO: 1:

```
GAATTCCGAC AGCGCGGGAC AGCCAGGGGA GCGCGCTGGG GCCGCAGCAT GCGGGAACCC        60

GCTAAACCCG GTGGCTGCTG AGGCGGCCGA GATGCTCGTG CGCGCAGCGC GCCCCACTGC       120

ATCCTCGACC TTCTCGGGCT ACAGGGACCG TCAGTGGCGA CT ATG GGC AGA GTG         174
                                             Met Gly Arg Val
                                               1

GGC TAT TGG ACC CTG CTG GTG CTG CCG GCC CTT CTG GTC TGG CGC GGT        222
Gly Tyr Trp Thr Leu Leu Val Leu Pro Ala Leu Leu Val Trp Arg Gly
  5              10                  15                  20

CCG GCG CCG AGC GCG GCG GCG GAG AAG GGT CCC CCC GCG CTA AAT ATT        270
Pro Ala Pro Ser Ala Ala Ala Glu Lys Gly Pro Pro Ala Leu Asn Ile
                      25                  30                  35

GCG GTG ATG CTG GGT CAC AGC CAC GAC GTG ACA GAG CGC GAA CTT CGA        318
Ala Val Met Leu Gly His Ser His Asp Val Thr Glu Arg Glu Leu Arg
             40                  45                  50

ACA CTG TGG GGC CCC GAG CAG GCG GCG GGG CTG CCC CTG GAC GTG AAC        366
Thr Leu Trp Gly Pro Glu Gln Ala Ala Gly Leu Pro Leu Asp Val Asn
         55                  60                  65

GTG GTA GCT CTG CTG ATG AAC CGC ACC GAC CCC AAG AGC CTC ATC ACG        414
Val Val Ala Leu Leu Met Asn Arg Thr Asp Pro Lys Ser Leu Ile Thr
     70                  75                  80

CAC GTG TGC GAC CTC ATG TCC GGG GCA CGC ATC CAC GGC CTC GTG TTT        462
His Val Cys Asp Leu Met Ser Gly Ala Arg Ile His Gly Leu Val Phe
 85                  90                  95                 100

GGG GAC GAC ACG GAC CAG GAG GCC GTA GCC CAG ATG CTG GAT TTT ATC        510
Gly Asp Asp Thr Asp Gln Glu Ala Val Ala Gln Met Leu Asp Phe Ile
                 105                 110                 115

TCC TCC CAC ACC TTC GTC CCC ATC TTG GGC ATT CAT GGG GGC GCA TCT        558
Ser Ser His Thr Phe Val Pro Ile Leu Gly Ile His Gly Gly Ala Ser
             120                 125                 130

ATG ATC ATG GCT GAC AAG GAT CCG ACG TCT ACC TTC TTC CAG TTT GGA        606
Met Ile Met Ala Asp Lys Asp Pro Thr Ser Thr Phe Phe Gln Phe Gly
         135                 140                 145

GCG TCC ATC CAG CAG CAA GCC ACG GTC ATG CTG AAG ATC ATG CAG GAT        654
Ala Ser Ile Gln Gln Gln Ala Thr Val Met Leu Lys Ile Met Gln Asp
     150                 155                 160

TAT GAC TGG CAT GTC TTC TCC CTG GTG ACC ACT ATC TTC CCT GGC TAC        702
Tyr Asp Trp His Val Phe Ser Leu Val Thr Thr Ile Phe Pro Gly Tyr
165                 170                 175                 180

AGG GAA TTC ATC AGC TTC GTC AAG ACC ACA GTG GAC AAC AGC TTT GTG        750
Arg Glu Phe Ile Ser Phe Val Lys Thr Thr Val Asp Asn Ser Phe Val
                 185                 190                 195

GGC TGG GAC ATG CAG AAT GTG ATC ACA CTG GAC ACT TCC TTT GAG GAT        798
Gly Trp Asp Met Gln Asn Val Ile Thr Leu Asp Thr Ser Phe Glu Asp
             200                 205                 210

GCA AAG ACA CAA GTC CAG CTG AAG AAG ATC CAC TCT TCT GTC ATC TTG        846
Ala Lys Thr Gln Val Gln Leu Lys Lys Ile His Ser Ser Val Ile Leu
         215                 220                 225

CTC TAC TGT TCC AAA GAC GAG GCT GTT CTC ATT CTG AGT GAG GCC CGC        894
Leu Tyr Cys Ser Lys Asp Glu Ala Val Leu Ile Leu Ser Glu Ala Arg
     230                 235                 240

TCC CTT GGC CTC ACC GGG TAT GAT TTC TTC TGG ATT GTC CCC AGC TTG        942
Ser Leu Gly Leu Thr Gly Tyr Asp Phe Phe Trp Ile Val Pro Ser Leu
```

-continued

```
245              250              255              260

GTC TCT GGG AAC ACG GAG CTC ATC CCA AAA GAG TTT CCA TCG GGA CTC    990
Val Ser Gly Asn Thr Glu Leu Ile Pro Lys Glu Phe Pro Ser Gly Leu
            265              270              275

ATT TCT GTC TCC TAC GAT GAC TGG GAC TAC AGC CTG GAG GCG AGA GTG   1038
Ile Ser Val Ser Tyr Asp Asp Trp Asp Tyr Ser Leu Glu Ala Arg Val
                280              285              290

AGG GAC GGC ATT GGC ATC CTA ACC ACC GCT GCA TCT TCT ATG CTG GAG   1086
Arg Asp Gly Ile Gly Ile Leu Thr Thr Ala Ala Ser Ser Met Leu Glu
            295              300              305

AAG TTC TCC TAC ATC CCC GAG GCC AAG GCC AGC TGC TAC GGG CAG ATG   1134
Lys Phe Ser Tyr Ile Pro Glu Ala Lys Ala Ser Cys Tyr Gly Gln Met
            310              315              320

GAG AGG CCA GAG GTC CCG ATG CAC ACC TTG CAC CCA TTT ATG GTC AAT   1182
Glu Arg Pro Glu Val Pro Met His Thr Leu His Pro Phe Met Val Asn
325              330              335              340

GTT ACA TGG GAT GGC AAA GAC TTA TCC TTC ACT GAG GAA GGC TAC CAG   1230
Val Thr Trp Asp Gly Lys Asp Leu Ser Phe Thr Glu Glu Gly Tyr Gln
            345              350              355

GTG CAC CCC AGG CTG GTG GTG ATT GTG CTG AAC AAA GAC CGG GAA TGG   1278
Val His Pro Arg Leu Val Val Ile Val Leu Asn Lys Asp Arg Glu Trp
            360              365              370

GAA AAG GTG GGC AAG TGG GAG AAC CAT ACG CTG AGC CTG AGG CAC GCC   1326
Glu Lys Val Gly Lys Trp Glu Asn His Thr Leu Ser Leu Arg His Ala
            375              380              385

GTG TGG CCC AGG TAC AAG TCC TTC TCC GAC TGT GAG CCG GAT GAC AAC   1374
Val Trp Pro Arg Tyr Lys Ser Phe Ser Asp Cys Glu Pro Asp Asp Asn
            390              395              400

CAT CTC AGC ATC GTC ACC CTG GAG GAG GCC CCA TTC GTC ATC GTG GAA   1422
His Leu Ser Ile Val Thr Leu Glu Glu Ala Pro Phe Val Ile Val Glu
405              410              415              420

GAC ATA GAC CCC CTA ACC GAG ACG TGT GTG AGG AAC ACC GTG CCA TGT   1470
Asp Ile Asp Pro Leu Thr Glu Thr Cys Val Arg Asn Thr Val Pro Cys
            425              430              435

CGG AAG TTC GTC AAA ATC AAC AAT TCA ACC AAT GAG GGG ATG AAT GTG   1518
Arg Lys Phe Val Lys Ile Asn Asn Ser Thr Asn Glu Gly Met Asn Val
            440              445              450

AAG AAA TGC TGC AAG GGG TTC TGC ATT GAT ATT CTG AAG AAG CTT TCC   1566
Lys Lys Cys Cys Lys Gly Phe Cys Ile Asp Ile Leu Lys Lys Leu Ser
            455              460              465

AGA ACT GTG AAG TTT ACT TAC GAC CTC TAT CTG GTG ACC AAT GGG AAG   1614
Arg Thr Val Lys Phe Thr Tyr Asp Leu Tyr Leu Val Thr Asn Gly Lys
            470              475              480

CAT GGC AAG AAA GTT AAC AAT GTG TGG AAT GGA ATG ATC GGT GAA GTG   1662
His Gly Lys Lys Val Asn Asn Val Trp Asn Gly Met Ile Gly Glu Val
485              490              495              500

GTC TAT CAA CGG GCA GTC ATG GCA GTT GGC TCG CTC ACC ATC AAT GAG   1710
Val Tyr Gln Arg Ala Val Met Ala Val Gly Ser Leu Thr Ile Asn Glu
            505              510              515

GAA CGT TCT GAA GTG GTG GAC TTC TCT GTG CCC TTT GTG GAA ACG GGA   1758
Glu Arg Ser Glu Val Val Asp Phe Ser Val Pro Phe Val Glu Thr Gly
            520              525              530

ATC AGT GTC ATG GTT TCA AGA AGT AAT GGC ACC GTC TCA CCT TCT GCT   1806
Ile Ser Val Met Val Ser Arg Ser Asn Gly Thr Val Ser Pro Ser Ala
            535              540              545

TTT CTA GAA CCA TTC AGC GCC TCT GTC TGG GTG ATG ATG TTT GTG ATG   1854
Phe Leu Glu Pro Phe Ser Ala Ser Val Trp Val Met Met Phe Val Met
            550              555              560

CTG CTC ATT GTT TCT GCC ATA GCT GTT TTT GTC TTT GAA TAC TTC AGC   1902
```

-continued

```
Leu Leu Ile Val Ser Ala Ile Ala Val Phe Val Phe Glu Tyr Phe Ser
565                 570                 575                 580

CCT GTT GGA TAC AAC AGA AAC TTA GCC AAA GGG AAA GCA CCC CAT GGG     1950
Pro Val Gly Tyr Asn Arg Asn Leu Ala Lys Gly Lys Ala Pro His Gly
                585                 590                 595

CCT TCT TTT ACA ATT GGA AAA GCT ATA TGG CTT CTT TGG GGC CTG GTG     1998
Pro Ser Phe Thr Ile Gly Lys Ala Ile Trp Leu Leu Trp Gly Leu Val
            600                 605                 610

TTC AAT AAC TCC GTG CCT GTC CAG AAT CCT AAA GGG ACC ACC AGC AAG     2046
Phe Asn Asn Ser Val Pro Val Gln Asn Pro Lys Gly Thr Thr Ser Lys
        615                 620                 625

ATC ATG GTA TCT GTA TGG GCC TTC TTC GCT GTC ATA TTC CTG GCT AGC     2094
Ile Met Val Ser Val Trp Ala Phe Phe Ala Val Ile Phe Leu Ala Ser
    630                 635                 640

TAC ACA GCC AAT CTG GCT GCC TTC ATG ATC CAA GAG GAA TTT GTG GAC     2142
Tyr Thr Ala Asn Leu Ala Ala Phe Met Ile Gln Glu Glu Phe Val Asp
645                 650                 655                 660

CAA GTG ACC GGC CTC AGT GAC AAA AAG TTT CAG AGA CCT CAT GAC TAT     2190
Gln Val Thr Gly Leu Ser Asp Lys Lys Phe Gln Arg Pro His Asp Tyr
                665                 670                 675

TCC CCA CCT TTT CGA TTT GGG ACA GTG CCT AAT GGA AGC ACG GAG AGA     2238
Ser Pro Pro Phe Arg Phe Gly Thr Val Pro Asn Gly Ser Thr Glu Arg
            680                 685                 690

AAC ATT CGG AAT AAC TAT CCC TAC ATG CAT CAG TAC ATG ACC AAA TTT     2286
Asn Ile Arg Asn Asn Tyr Pro Tyr Met His Gln Tyr Met Thr Lys Phe
        695                 700                 705

AAT CAG AAA GGA GTA GAG GAC GCC TTG GTC AGC CTG AAA ACG GGA AAG     2334
Asn Gln Lys Gly Val Glu Asp Ala Leu Val Ser Leu Lys Thr Gly Lys
    710                 715                 720

CTG GAC GCT TTC ATC TAC GAT GCC GCA GTC TTG AAT TAC AAG GCT GGG     2382
Leu Asp Ala Phe Ile Tyr Asp Ala Ala Val Leu Asn Tyr Lys Ala Gly
725                 730                 735                 740

AGG GAT GAA GGC TGC AAG CTG GTG ACC ATC GGG AGT GGG TAC ATC TTT     2430
Arg Asp Glu Gly Cys Lys Leu Val Thr Ile Gly Ser Gly Tyr Ile Phe
                745                 750                 755

GCC ACC ACC GGT TAT GGA ATT GCC CTT CAG AAA GGC TCT CCT TGG AAG     2478
Ala Thr Thr Gly Tyr Gly Ile Ala Leu Gln Lys Gly Ser Pro Trp Lys
            760                 765                 770

AGG CAG ATC GAC CTG GCC TTG CTT CAG TTT GTG GGT GAT GGT GAG ATG     2526
Arg Gln Ile Asp Leu Ala Leu Leu Gln Phe Val Gly Asp Gly Glu Met
        775                 780                 785

GAG GAG CTG GAG ACC CTG TGG CTC ACT GGG ATC TGC CAC AAC GAG AAG     2574
Glu Glu Leu Glu Thr Leu Trp Leu Thr Gly Ile Cys His Asn Glu Lys
    790                 795                 800

AAC GAG GTG ATG AGC AGC CAG CTG GAC ATT GAC AAC ATG GCG GGC GTA     2622
Asn Glu Val Met Ser Ser Gln Leu Asp Ile Asp Asn Met Ala Gly Val
805                 810                 815                 820

TTC TAC ATG CTG GCT GCC GCC ATG GCC CTT AGC CTC ATC ACC TTC ATC     2670
Phe Tyr Met Leu Ala Ala Ala Met Ala Leu Ser Leu Ile Thr Phe Ile
                825                 830                 835

TGG GAG CAC CTC TTC TAC TGG AAG CTG CGC TTC TGT TTC ACG GGC GTG     2718
Trp Glu His Leu Phe Tyr Trp Lys Leu Arg Phe Cys Phe Thr Gly Val
            840                 845                 850

TGC TCC GAC CGG CCT GGG TTG CTC TTC TCC ATC AGC AGG GGC ATC TAC     2766
Cys Ser Asp Arg Pro Gly Leu Leu Phe Ser Ile Ser Arg Gly Ile Tyr
        855                 860                 865

AGC TGC ATT CAT GGA GTG CAC ATT GAA GAA AAG AAG AAG TCT CCA GAC     2814
Ser Cys Ile His Gly Val His Ile Glu Glu Lys Lys Lys Ser Pro Asp
    870                 875                 880
```

```
TTC AAT CTG ACG GGA TCC CAG AGC AAC ATG TTA AAA CTC CTC CGG TCA    2862
Phe Asn Leu Thr Gly Ser Gln Ser Asn Met Leu Lys Leu Leu Arg Ser
885                 890                 895                 900

GCC AAA AAC ATT TCC AGC ATG TCC AAC ATG AAC TCC TCA AGA ATG GAC    2910
Ala Lys Asn Ile Ser Ser Met Ser Asn Met Asn Ser Ser Arg Met Asp
            905                 910                 915

TCA CCC AAA AGA GCT GCT GAC TTC ATC CAA AGA GGT TCC CTC ATC ATG    2958
Ser Pro Lys Arg Ala Ala Asp Phe Ile Gln Arg Gly Ser Leu Ile Met
        920                 925                 930

GAC ATG GTT TCA GAT AAG GGG AAT TTG ATG TAC TCA GAC AAC AGG TCC    3006
Asp Met Val Ser Asp Lys Gly Asn Leu Met Tyr Ser Asp Asn Arg Ser
    935                 940                 945

TTT CAG GGG AAA GAG AGC ATT TTT GGA GAC AAC ATG AAC GAA CTC CAA    3054
Phe Gln Gly Lys Glu Ser Ile Phe Gly Asp Asn Met Asn Glu Leu Gln
950                 955                 960

ACA TTT GTG GCC AAC CGG CAG AAG GAT AAC CTC AAT AAC TAT GTA TTC    3102
Thr Phe Val Ala Asn Arg Gln Lys Asp Asn Leu Asn Asn Tyr Val Phe
965                 970                 975                 980

CAG GGA CAA CAT CCT CTT ACT CTC AAT GAG TCC AAC CCT AAC ACG GTG    3150
Gln Gly Gln His Pro Leu Thr Leu Asn Glu Ser Asn Pro Asn Thr Val
            985                 990                 995

GAG GTG GCC GTG AGC ACA GAA TCC AAA GCG AAC TCT AGA CCC CGG CAG    3198
Glu Val Ala Val Ser Thr Glu Ser Lys Ala Asn Ser Arg Pro Arg Gln
        1000                1005                1010

CTG TGG AAG AAA TCC GTA GAT TCC ATA CGC CAG GAT TCA CTA TCC CAG    3246
Leu Trp Lys Lys Ser Val Asp Ser Ile Arg Gln Asp Ser Leu Ser Gln
    1015                1020                1025

AAT CCA GTC TCC CAG AGG GAT GAG GCA ACA GCA GAG AAT AGG ACC CAC    3294
Asn Pro Val Ser Gln Arg Asp Glu Ala Thr Ala Glu Asn Arg Thr His
1030                1035                1040

TCC CTA AAG AGC CCT AGG TAT CTT CCA GAA GAG ATG GCC CAC TCT GAC    3342
Ser Leu Lys Ser Pro Arg Tyr Leu Pro Glu Glu Met Ala His Ser Asp
1045                1050                1055                1060

ATT TCA GAA ACG TCA AAT CGG GCC ACG TGC CAC AGG GAA CCT GAC AAC    3390
Ile Ser Glu Thr Ser Asn Arg Ala Thr Cys His Arg Glu Pro Asp Asn
            1065                1070                1075

AGT AAG AAC CAC AAA ACC AAG GAC AAC TTT AAA AGG TCA GTG GCC TCC    3438
Ser Lys Asn His Lys Thr Lys Asp Asn Phe Lys Arg Ser Val Ala Ser
        1080                1085                1090

AAA TAC CCC AAG GAC TGT AGT GAG GTC GAG CGC ACC TAC CTG AAA ACC    3486
Lys Tyr Pro Lys Asp Cys Ser Glu Val Glu Arg Thr Tyr Leu Lys Thr
    1095                1100                1105

AAA TCA AGC TCC CCT AGA GAC AAG ATC TAC ACT ATA GAT GGT GAG AAG    3534
Lys Ser Ser Ser Pro Arg Asp Lys Ile Tyr Thr Ile Asp Gly Glu Lys
1110                1115                1120

GAG CCT GGT TTC CAC TTA GAT CCA CCC CAG TTT GTT GAA AAT GTG ACC    3582
Glu Pro Gly Phe His Leu Asp Pro Pro Gln Phe Val Glu Asn Val Thr
1125                1130                1135                1140

CTG CCC GAG AAC GTG GAC TTC CCG GAC CCC TAC CAG GAT CCC AGT GAA    3630
Leu Pro Glu Asn Val Asp Phe Pro Asp Pro Tyr Gln Asp Pro Ser Glu
            1145                1150                1155

AAC TTC CGC AAG GGG GAC TCC ACG CTG CCA ATG AAC CGG AAC CCC TTG    3678
Asn Phe Arg Lys Gly Asp Ser Thr Leu Pro Met Asn Arg Asn Pro Leu
        1160                1165                1170

CAT AAT GAA GAG GGG CTT TCC AAC AAC GAC CAG TAT AAA CTC TAC TCC    3726
His Asn Glu Glu Gly Leu Ser Asn Asn Asp Gln Tyr Lys Leu Tyr Ser
    1175                1180                1185

AAG CAC TTC ACC TTG AAA GAC AAG GGT TCC CCG CAC AGT GAG ACC AGC    3774
Lys His Phe Thr Leu Lys Asp Lys Gly Ser Pro His Ser Glu Thr Ser
1190                1195                1200
```

```
GAG CGA TAC CGG CAG AAC TCC ACG CAC TGC AGA AGC TGC CTT TCC AAC        3822
Glu Arg Tyr Arg Gln Asn Ser Thr His Cys Arg Ser Cys Leu Ser Asn
1205                1210                1215                1220

ATG CCC ACC TAT TCA GGC CAC TTC ACC ATG AGG TCC CCC TTC AAG TGC        3870
Met Pro Thr Tyr Ser Gly His Phe Thr Met Arg Ser Pro Phe Lys Cys
                1225                1230                1235

GAT GCC TGC CTG CGG ATG GGG AAT CTC TAT GAC ATC GAT GAA GAC CAG        3918
Asp Ala Cys Leu Arg Met Gly Asn Leu Tyr Asp Ile Asp Glu Asp Gln
            1240                1245                1250

ATG CTT CAG GAG ACA GGT AAC CCA GCC ACC GGG GAG CAG GTC TAC CAG        3966
Met Leu Gln Glu Thr Gly Asn Pro Ala Thr Gly Glu Gln Val Tyr Gln
        1255                1260                1265

CAG GAC TGG GCA CAG AAC AAT GCC CTT CAA TTA CAA AAG AAC AAG CTA        4014
Gln Asp Trp Ala Gln Asn Asn Ala Leu Gln Leu Gln Lys Asn Lys Leu
    1270                1275                1280

AGG ATT AGC CGT CAG CAT TCC TAC GAT AAC ATT GTC GAC AAA CCT AGG        4062
Arg Ile Ser Arg Gln His Ser Tyr Asp Asn Ile Val Asp Lys Pro Arg
1285                1290                1295                1300

GAG CTA GAC CTT AGC AGG CCC TCC CGG AGC ATA AGC CTC AAG GAC AGG        4110
Glu Leu Asp Leu Ser Arg Pro Ser Arg Ser Ile Ser Leu Lys Asp Arg
                1305                1310                1315

GAA CGG CTT CTG GAG GGA AAT TTT TAC GGC AGC CTG TTT AGT GTC CCC        4158
Glu Arg Leu Leu Glu Gly Asn Phe Tyr Gly Ser Leu Phe Ser Val Pro
            1320                1325                1330

TCA AGC AAA CTC TCG GGG AAA AAA AGC TCC CTT TTC CCC CAA GGT CTG        4206
Ser Ser Lys Leu Ser Gly Lys Lys Ser Ser Leu Phe Pro Gln Gly Leu
        1335                1340                1345

GAG GAC AGC AAG AGG AGC AAG TCT CTC TTG CCA GAC CAC ACC TCC GAT        4254
Glu Asp Ser Lys Arg Ser Lys Ser Leu Leu Pro Asp His Thr Ser Asp
    1350                1355                1360

AAC CCT TTC CTC CAC TCC CAC AGG GAT GAC CAA CGC TTG GTT ATT GGG        4302
Asn Pro Phe Leu His Ser His Arg Asp Asp Gln Arg Leu Val Ile Gly
1365                1370                1375                1380

AGA TGC CCC TCG GAC CCT TAC AAA CAC TCG TTG CCA TCC CAG GCG GTG        4350
Arg Cys Pro Ser Asp Pro Tyr Lys His Ser Leu Pro Ser Gln Ala Val
                1385                1390                1395

AAT GAC AGC TAT CTT CGG TCG TCC TTG AGG TCA ACG GCA TCG TAC TGT        4398
Asn Asp Ser Tyr Leu Arg Ser Ser Leu Arg Ser Thr Ala Ser Tyr Cys
            1400                1405                1410

TCC AGG GAC AGT CGG GGC CAC AAT GAT GTG TAT ATT TCG GAG CAT GTT        4446
Ser Arg Asp Ser Arg Gly His Asn Asp Val Tyr Ile Ser Glu His Val
        1415                1420                1425

ATG CCT TAT GCT GCA AAT AAG AAT AAT ATG TAC TCT ACC CCC AGG GTT        4494
Met Pro Tyr Ala Ala Asn Lys Asn Asn Met Tyr Ser Thr Pro Arg Val
    1430                1435                1440

TTA AAT TCC TGC AGC AAT AGA CGC GTG TAC AAG AAA ATG CCT AGT ATC        4542
Leu Asn Ser Cys Ser Asn Arg Arg Val Tyr Lys Lys Met Pro Ser Ile
1445                1450                1455                1460

GAA TCT GAT GTT TAAAAATCTT CCATTAATGT TTTATCTATA GGGAAATATA            4594
Glu Ser Asp Val

CGTAATGGCC AATGTTCTGG AGGGTAAATG TTGGATGTCC AATAGTGCCC TGCTAAGAGG      4654

AAGAAGATGT AGGGAGGTAT TTTGTTGTTG TTGTTGTTGG CTCTTTTGCA CACGGCTTCA      4714

TGCCATAATC TTCCACTCAA GGAATCTTGT GAGGTGTGTG CTGAGCATGG CAGACACCAG      4774

ATAGGTGAGT CCTTAACCAA AAATAACTAA CTACATAAGG GCAAGTCTCC GGGACATGCC      4834

TACTGGGTAT GTTGGCAATA ATGATGCATT GGATGCCAAT GGTGATGTTA TGATTTCCTA      4894

TATTCCAAAT TCCATTAAGG TCAGCCCACC ATGTAATTTT CTCATCAGAA ATGCCTAATG      4954
```

-continued

```
GTTTCTCTAA TACAGAATAA GCAATATGGT GTGCATGTAA ACCTGACACA GACAAAATAA    5014

AAACAGTTAA GAATGCATCT GCACTGTAGT CGGATTTGAA CATGTGCAAG AGATTAGGAA    5074

GTTTGGCTCG TAACAGTTTC AGCTTTCTTG TTATGCCTTC CATCACAGCC CAGGCTCACC    5134

CCAAGAACTC CAGGCTCCCC TAAAGAATAG CAAATCAGTG TGTTCGTGAT GACTGTGCTA    5194

CCTTCATTAT AGTTCATTTC CAAGACACAT CTGGAGCCAA AGGCCCGAGG GACCCTCAGG    5254

TGGGGAGAGC TACAGGAATC TCTTTGGATG TTGATGTGTG TTTCTCTCTA CCCTCGGCTT    5314

CGATGGTCTT GTTCAGAGCT GCATAAACTA ACACATTTAT GTCTCCGAGA TCTAAGTGTG    5374

GATCTTCTGT CTGTGACACA GTGGCCATTG TAGTTTATCC CGAAGACGCC TATGTACGTA    5434

AGTTTGCATT TCCTCCCTTC TGGTGATGAC TCAGGGTTGT ATAGTATCTG TTACCCCTTC    5494

CCTCCCAGAG TAACCATAAC TCGTTCCGTT TCCAAACAGC CATGGTGGTG TCCAATTAGC    5554

TGTGTATCGC TCTTCCCAGA GTTGTTAATG TGGTGACATG CACCAACAGC CGTATGTGTA    5614

CTGTGATCTG TAAGAAGTAC AATGCCATCT GTCTGCCGAA GGCTAGCATG GTTTTAGGTT    5674

TATCTTCCTT CACATCCAGA AATTCTGTTG GACACTCACT TCCACCCCAA ACTCCTCAAA    5734

TCAAAAGCCT TCAAAACACG AGGCACTCTT GGATCTACCC TGAGTATCCT CCAAACTGTG    5794

GATACAGTTT AGTGAGACAA GCAATTTCTC CCTTCTGAGT TATTCTCTCT GTTGGTGGCA    5854

AACCACTTCA TAGCACCAAC AGAGATGTAG GAAAAATTCC TCAAAGTATT TGTCATTTCT    5914

GAGTCGCCTG CATTATCCCA TTCTTATTCT CCTCAAACCT GTGCATATAT GACATGAAAT    5974

GATATCCATT TTTTTTTTAA GTTAGAAACA GAGAGGGGAA TACTTATGCA TGGGGAGCCT    6034

GTTAGCACAG TGCCTGCCAC AAAAACAAGT GCCCCCGACA AGATAGTTGC TATGTTATGA    6094

CACTTTCTCA GATCAGGATT TTCTAGTTTA AAAATTAAAT ATCATAAAAC GGAATTC      6151
```

(2) INFORMATION FOR SEQ ID NO: 2:

(i) SEQUENCE CHARACTERISTICS:
        (A) LENGTH: 1464 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gly Arg Val Gly Tyr Trp Thr Leu Leu Val Leu Pro Ala Leu Leu
 1               5                  10                  15

Val Trp Arg Gly Pro Ala Pro Ser Ala Ala Ala Glu Lys Gly Pro Pro
            20                  25                  30

Ala Leu Asn Ile Ala Val Met Leu Gly His Ser His Asp Val Thr Glu
        35                  40                  45

Arg Glu Leu Arg Thr Leu Trp Gly Pro Glu Gln Ala Ala Gly Leu Pro
    50                  55                  60

Leu Asp Val Asn Val Val Ala Leu Leu Met Asn Arg Thr Asp Pro Lys
65                  70                  75                  80

Ser Leu Ile Thr His Val Cys Asp Leu Met Ser Gly Ala Arg Ile His
                85                  90                  95

Gly Leu Val Phe Gly Asp Asp Thr Asp Gln Glu Ala Val Ala Gln Met
           100                 105                 110

Leu Asp Phe Ile Ser Ser His Thr Phe Val Pro Ile Leu Gly Ile His
       115                 120                 125

Gly Gly Ala Ser Met Ile Met Ala Asp Lys Asp Pro Thr Ser Thr Phe
   130                 135                 140
```

```
Phe Gln Phe Gly Ala Ser Ile Gln Gln Ala Thr Val Met Leu Lys
145                 150                 155                 160

Ile Met Gln Asp Tyr Asp Trp His Val Phe Ser Leu Val Thr Thr Ile
                165                 170                 175

Phe Pro Gly Tyr Arg Glu Phe Ile Ser Phe Val Lys Thr Thr Val Asp
                180                 185                 190

Asn Ser Phe Val Gly Trp Asp Met Gln Asn Val Ile Thr Leu Asp Thr
            195                 200                 205

Ser Phe Glu Asp Ala Lys Thr Gln Val Gln Leu Lys Lys Ile His Ser
    210                 215                 220

Ser Val Ile Leu Leu Tyr Cys Ser Lys Asp Glu Ala Val Leu Ile Leu
225                 230                 235                 240

Ser Glu Ala Arg Ser Leu Gly Leu Thr Gly Tyr Asp Phe Phe Trp Ile
                245                 250                 255

Val Pro Ser Leu Val Ser Gly Asn Thr Glu Leu Ile Pro Lys Glu Phe
                260                 265                 270

Pro Ser Gly Leu Ile Ser Val Ser Tyr Asp Asp Trp Asp Tyr Ser Leu
                275                 280                 285

Glu Ala Arg Val Arg Asp Gly Ile Gly Ile Leu Thr Thr Ala Ala Ser
290                 295                 300

Ser Met Leu Glu Lys Phe Ser Tyr Ile Pro Glu Ala Lys Ala Ser Cys
305                 310                 315                 320

Tyr Gly Gln Met Glu Arg Pro Glu Val Pro Met His Thr Leu His Pro
                325                 330                 335

Phe Met Val Asn Val Thr Trp Asp Gly Lys Asp Leu Ser Phe Thr Glu
                340                 345                 350

Glu Gly Tyr Gln Val His Pro Arg Leu Val Val Ile Val Leu Asn Lys
                355                 360                 365

Asp Arg Glu Trp Glu Lys Val Gly Lys Trp Glu Asn His Thr Leu Ser
                370                 375                 380

Leu Arg His Ala Val Trp Pro Arg Tyr Lys Ser Phe Ser Asp Cys Glu
385                 390                 395                 400

Pro Asp Asp Asn His Leu Ser Ile Val Thr Leu Glu Glu Ala Pro Phe
                405                 410                 415

Val Ile Val Glu Asp Ile Asp Pro Leu Thr Glu Thr Cys Val Arg Asn
                420                 425                 430

Thr Val Pro Cys Arg Lys Phe Val Lys Ile Asn Asn Ser Thr Asn Glu
                435                 440                 445

Gly Met Asn Val Lys Lys Cys Cys Lys Gly Phe Cys Ile Asp Ile Leu
450                 455                 460

Lys Lys Leu Ser Arg Thr Val Lys Phe Thr Tyr Asp Leu Tyr Leu Val
465                 470                 475                 480

Thr Asn Gly Lys His Gly Lys Lys Val Asn Asn Val Trp Asn Gly Met
                485                 490                 495

Ile Gly Glu Val Val Tyr Gln Arg Ala Val Met Ala Val Gly Ser Leu
                500                 505                 510

Thr Ile Asn Glu Glu Arg Ser Glu Val Val Asp Phe Ser Val Pro Phe
                515                 520                 525

Val Glu Thr Gly Ile Ser Val Met Val Ser Arg Ser Asn Gly Thr Val
            530                 535                 540

Ser Pro Ser Ala Phe Leu Glu Pro Phe Ser Ala Ser Val Trp Val Met
545                 550                 555                 560
```

```
Met Phe Val Met Leu Leu Ile Val Ser Ala Ile Ala Val Phe Val Phe
                565                 570                 575

Glu Tyr Phe Ser Pro Val Gly Tyr Asn Arg Asn Leu Ala Lys Gly Lys
            580                 585                 590

Ala Pro His Gly Pro Ser Phe Thr Ile Gly Lys Ala Ile Trp Leu Leu
        595                 600                 605

Trp Gly Leu Val Phe Asn Asn Ser Val Pro Val Gln Asn Pro Lys Gly
    610                 615                 620

Thr Thr Ser Lys Ile Met Val Ser Val Trp Ala Phe Phe Ala Val Ile
625                 630                 635                 640

Phe Leu Ala Ser Tyr Thr Ala Asn Leu Ala Ala Phe Met Ile Gln Glu
                645                 650                 655

Glu Phe Val Asp Gln Val Thr Gly Leu Ser Asp Lys Lys Phe Gln Arg
            660                 665                 670

Pro His Asp Tyr Ser Pro Pro Phe Arg Phe Gly Thr Val Pro Asn Gly
        675                 680                 685

Ser Thr Glu Arg Asn Ile Arg Asn Asn Tyr Pro Tyr Met His Gln Tyr
    690                 695                 700

Met Thr Lys Phe Asn Gln Lys Gly Val Glu Asp Ala Leu Val Ser Leu
705                 710                 715                 720

Lys Thr Gly Lys Leu Asp Ala Phe Ile Tyr Asp Ala Ala Val Leu Asn
                725                 730                 735

Tyr Lys Ala Gly Arg Asp Glu Gly Cys Lys Leu Val Thr Ile Gly Ser
            740                 745                 750

Gly Tyr Ile Phe Ala Thr Thr Gly Tyr Gly Ile Ala Leu Gln Lys Gly
        755                 760                 765

Ser Pro Trp Lys Arg Gln Ile Asp Leu Ala Leu Leu Gln Phe Val Gly
    770                 775                 780

Asp Gly Glu Met Glu Glu Leu Glu Thr Leu Trp Leu Thr Gly Ile Cys
785                 790                 795                 800

His Asn Glu Lys Asn Glu Val Met Ser Ser Gln Leu Asp Ile Asp Asn
                805                 810                 815

Met Ala Gly Val Phe Tyr Met Leu Ala Ala Ala Met Ala Leu Ser Leu
            820                 825                 830

Ile Thr Phe Ile Trp Glu His Leu Phe Tyr Trp Lys Leu Arg Phe Cys
        835                 840                 845

Phe Thr Gly Val Cys Ser Asp Arg Pro Gly Leu Leu Phe Ser Ile Ser
    850                 855                 860

Arg Gly Ile Tyr Ser Cys Ile His Gly Val His Ile Glu Glu Lys Lys
865                 870                 875                 880

Lys Ser Pro Asp Phe Asn Leu Thr Gly Ser Gln Ser Asn Met Leu Lys
                885                 890                 895

Leu Leu Arg Ser Ala Lys Asn Ile Ser Ser Met Ser Asn Met Asn Ser
            900                 905                 910

Ser Arg Met Asp Ser Pro Lys Arg Ala Ala Asp Phe Ile Gln Arg Gly
        915                 920                 925

Ser Leu Ile Met Asp Met Val Ser Asp Lys Gly Asn Leu Met Tyr Ser
    930                 935                 940

Asp Asn Arg Ser Phe Gln Gly Lys Glu Ser Ile Phe Gly Asp Asn Met
945                 950                 955                 960

Asn Glu Leu Gln Thr Phe Val Ala Asn Arg Gln Lys Asp Asn Leu Asn
                965                 970                 975

Asn Tyr Val Phe Gln Gly Gln His Pro Leu Thr Leu Asn Glu Ser Asn
```

```
                980             985             990
Pro Asn Thr Val Glu Val Ala Val Ser Thr Glu Ser Lys Ala Asn Ser
        995            1000            1005

Arg Pro Arg Gln Leu Trp Lys Lys Ser Val Asp Ser Ile Arg Gln Asp
       1010            1015            1020

Ser Leu Ser Gln Asn Pro Val Ser Gln Arg Asp Glu Ala Thr Ala Glu
1025            1030            1035            1040

Asn Arg Thr His Ser Leu Lys Ser Pro Arg Tyr Leu Pro Glu Glu Met
           1045            1050            1055

Ala His Ser Asp Ile Ser Glu Thr Ser Asn Arg Ala Thr Cys His Arg
       1060            1065            1070

Glu Pro Asp Asn Ser Lys Asn His Lys Thr Lys Asp Asn Phe Lys Arg
           1075            1080            1085

Ser Val Ala Ser Lys Tyr Pro Lys Asp Cys Ser Glu Val Glu Arg Thr
       1090            1095            1100

Tyr Leu Lys Thr Lys Ser Ser Ser Pro Arg Asp Lys Ile Tyr Thr Ile
1105            1110            1115            1120

Asp Gly Glu Lys Glu Pro Gly Phe His Leu Asp Pro Pro Gln Phe Val
           1125            1130            1135

Glu Asn Val Thr Leu Pro Glu Asn Val Asp Phe Pro Asp Pro Tyr Gln
           1140            1145            1150

Asp Pro Ser Glu Asn Phe Arg Lys Gly Asp Ser Thr Leu Pro Met Asn
       1155            1160            1165

Arg Asn Pro Leu His Asn Glu Glu Gly Leu Ser Asn Asn Asp Gln Tyr
       1170            1175            1180

Lys Leu Tyr Ser Lys His Phe Thr Leu Lys Asp Lys Gly Ser Pro His
1185            1190            1195            1200

Ser Glu Thr Ser Glu Arg Tyr Arg Gln Asn Ser Thr His Cys Arg Ser
           1205            1210            1215

Cys Leu Ser Asn Met Pro Thr Tyr Ser Gly His Phe Thr Met Arg Ser
           1220            1225            1230

Pro Phe Lys Cys Asp Ala Cys Leu Arg Met Gly Asn Leu Tyr Asp Ile
       1235            1240            1245

Asp Glu Asp Gln Met Leu Gln Glu Thr Gly Asn Pro Ala Thr Gly Glu
       1250            1255            1260

Gln Val Tyr Gln Gln Asp Trp Ala Gln Asn Asn Ala Leu Gln Leu Gln
1265            1270            1275            1280

Lys Asn Lys Leu Arg Ile Ser Arg Gln His Ser Tyr Asp Asn Ile Val
           1285            1290            1295

Asp Lys Pro Arg Glu Leu Asp Leu Ser Arg Pro Ser Arg Ser Ile Ser
       1300            1305            1310

Leu Lys Asp Arg Glu Arg Leu Leu Glu Gly Asn Phe Tyr Gly Ser Leu
       1315            1320            1325

Phe Ser Val Pro Ser Ser Lys Leu Ser Gly Lys Ser Ser Leu Phe
       1330            1335            1340

Pro Gln Gly Leu Glu Asp Ser Lys Arg Ser Lys Ser Leu Leu Pro Asp
1345            1350            1355            1360

His Thr Ser Asp Asn Pro Phe Leu His Ser His Arg Asp Asp Gln Arg
           1365            1370            1375

Leu Val Ile Gly Arg Cys Pro Ser Asp Pro Tyr Lys His Ser Leu Pro
           1380            1385            1390

Ser Gln Ala Val Asn Asp Ser Tyr Leu Arg Ser Ser Leu Arg Ser Thr
       1395            1400            1405
```

```
Ala Ser Tyr Cys Ser Arg Asp Ser Arg Gly His Asn Asp Val Tyr Ile
    1410                1415                1420
Ser Glu His Val Met Pro Tyr Ala Ala Asn Lys Asn Asn Met Tyr Ser
1425                1430                1435                1440
Thr Pro Arg Val Leu Asn Ser Cys Ser Asn Arg Arg Val Tyr Lys Lys
            1445                1450                1455
Met Pro Ser Ile Glu Ser Asp Val
        1460
```

(2) INFORMATION FOR SEQ ID NO: 3:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 3:

```
Lys Glu Phe Pro Ser Gly Leu Ile Ser Val Ser Tyr Asp Asp Trp Asp
  1               5                  10                  15
Tyr Ser Leu Glu
            20
```

(2) INFORMATION FOR SEQ ID NO: 4:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO: 4:

```
AAAAGAGTTT CCATCGGGAC TCATTTCTGT CTCCTACGAT GACTGGGACT ACAGCCTGGA    60
G                                                                   61
```

(2) INFORMATION FOR SEQ ID NO: 5:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO: 5:

```
AGAAGAGTTT CCATCGGGAC TCATTTCTGT CTCCTACGAT GACTGGGACT ACAGCCTGGA    60
G                                                                   61
```

(2) INFORMATION FOR SEQ ID NO: 6:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 6:

```
Glu Glu Phe Pro Ser Gly Leu Ile Ser Val Ser Tyr Asp Asp Trp Asp
  1               5                  10                  15
Tyr Ser Leu Glu
            20
```

(2) INFORMATION FOR SEQ ID NO: 7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 7:

```
GGGGTTTAGA TCTGGGTNAT GATGTTYGTN ATG                           33
```

(2) INFORMATION FOR SEQ ID NO: 8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 8:

```
GGGGTTTAGA TCTGCNGCRT CRTADATRAA NGC                           33
```

(2) INFORMATION FOR SEQ ID NO: 9:

(i) SEQUENCE CHARACTERISTICS:
        (A) LENGTH: 4659 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: misc_feature
        (B) LOCATION: 2781..2838
        (D) OTHER INFORMATION: /function= "transmembrane domain"

(ix) FEATURE:
        (A) NAME/KEY: misc_feature
        (B) LOCATION: 2895..2958
        (D) OTHER INFORMATION: /function= "transmembrane domain"

(ix) FEATURE:
        (A) NAME/KEY: misc_feature
        (B) LOCATION: 2988..3045
        (D) OTHER INFORMATION: /function= "transmembrane domain"

(ix) FEATURE:
        (A) NAME/KEY: misc_feature
        (B) LOCATION: 3534..3597
        (D) OTHER INFORMATION: /function= "transmembrane domain"

(ix) FEATURE:
        (A) NAME/KEY: CDS
        (B) LOCATION: 1099..3753

(ix) FEATURE:
        (A) NAME/KEY: mat_peptide
        (B) LOCATION: 1153..3753
        (D) OTHER INFORMATION: /product= "NMDAR1-1"

(ix) FEATURE:
        (A) NAME/KEY: sig_peptide
        (B) LOCATION: 1099..1152

(xi) SEQUENCE DESCRIPTION: SEQ ID NO: 9:

```
GAATTCCGGT AAGGCTCTGG AAAAGGGGGC GCTGGGAGCG CATTGCGAGG GGGCTGGAGA    60

GGGAGAGAGG AGCGGAAGCT GAGGGTGTGA AACGGCTGGC CCCGAACACA CCTCGCGGCG   120

CTCCAGTGAT TCCTGGTGTC CGACCTCAGC CCCAGTCAGT GCGGGTCCAG TTTCCAGGCT   180

CTCGCGGAAG GCCTGGCTGA GCACATGCGG CAGCCACGGT CGCCCTCCCT ATTCCTCTTA   240
```

```
GCCCGAGGAG GGGGGTCCCA AGTTACATGG CCACGCAGAT GGGGCCTCTC CCTCATTTCT    300

GAACCTTGTG GGGAGGGGAA CCTTGAAGGG AGCGCCCCCC AGAGCCATGG CTTAGGGCCT    360

CCCCCACCCC TCTGGAGCTC CAGTCTGCAA GAGTCAGGAG CCGAAATATC GCTGACTGTG    420

GGTGACGACT CTTGCGCGCA CACACACATA CAAGCGGGCA CGACGCGTTC GGTCCTATTA    480

AAAGGCACGC AAGGGTGCGG CTGCACGCGG TGACACGGAC CCCTCTAACG TTTCCAAACT    540

GAGCTCCCTG CAGGTCCCCG ACAGCACAGG CCCCTGTCCC AGGACCCCTC CAGGCACGCG    600

CTCACACGCA CACGCGCGCT CCCCGGCTCA CGCGCGCTCC GACACACACG CTCACGCGAA    660

CGCAGGCGCA CGCTCTGGCG CGGGAGGCGC CCCTTCGCCT CCGTGTTGGG AAGCGGGGGC    720

GGCGGGAGGG GCAGGAGACG TTGGCCCCGC TCGCGTTTCT GCAGCTGCTG CAGTCGCCGC    780

AGCGTCCGGA CCGGAACCAG CGCCGTCCGC GGAGCCGCCG CCGCCGCCGC CGGGCCCTTT    840

CCAAGCCGGG CGCTCGGAGC TGTGCCCGGC CCCGCTTCAG CACCGCGGAC AGCTCCGGCC    900

GCGTGGGGCT GAGCCGAGCC CCCGCGCACG CTTCAGCCCC CTTCCCTCGG CCGACGTCCC    960

GGGACCGCCG CTCCGGGGGA GACGTGGCGT CCGCAGCCCG CGGGGCCGGG CGAGCGCAGG    1020

ACGGCCCGGA AGCCCCGCGG GGGATGCGCC GAGGGCCCGC GTTCGCGCCG CGCAGAGCCA    1080

GGCCCGCGGC CCGAGCCC ATG AGC ACC ATG CGC CTG CTG ACG CTC GCC CTG    1131
                    Met Ser Thr Met Arg Leu Leu Thr Leu Ala Leu
                        -18         -15                 -10

CTG TTC TCC TGC TCC GTC GCC CGT GCC GCG TGC GAC CCC AAG ATC GTC    1179
Leu Phe Ser Cys Ser Val Ala Arg Ala Ala Cys Asp Pro Lys Ile Val
     -5                   1                   5

AAC ATT GGC GCG GTG CTG AGC ACG CGG AAG CAC GAG CAG ATG TTC CGC    1227
Asn Ile Gly Ala Val Leu Ser Thr Arg Lys His Glu Gln Met Phe Arg
 10              15                  20                  25

GAG GCC GTG AAC CAG GCC AAC AAG CGG CAC GGC TCC TGG AAG ATT CAG    1275
Glu Ala Val Asn Gln Ala Asn Lys Arg His Gly Ser Trp Lys Ile Gln
             30                  35                  40

CTC AAT GCC ACC TCC GTC ACG CAC AAG CCC AAC GCC ATC CAG ATG GCT    1323
Leu Asn Ala Thr Ser Val Thr His Lys Pro Asn Ala Ile Gln Met Ala
                 45                  50                  55

CTG TCG GTG TGC GAG GAC CTC ATC TCC AGC CAG GTC TAC GCC ATC CTA    1371
Leu Ser Val Cys Glu Asp Leu Ile Ser Ser Gln Val Tyr Ala Ile Leu
             60                  65                  70

GTT AGC CAT CCA CCT ACC CCC AAC GAC CAC TTC ACT CCC ACC CCT GTC    1419
Val Ser His Pro Pro Thr Pro Asn Asp His Phe Thr Pro Thr Pro Val
         75                  80                  85

TCC TAC ACA GCC GGC TTC TAC CGC ATA CCC GTG CTG GGG CTG ACC ACC    1467
Ser Tyr Thr Ala Gly Phe Tyr Arg Ile Pro Val Leu Gly Leu Thr Thr
 90                  95                 100                 105

CGC ATG TCC ATC TAC TCG GAC AAG AGC ATC CAC CTG AGC TTC CTG CGC    1515
Arg Met Ser Ile Tyr Ser Asp Lys Ser Ile His Leu Ser Phe Leu Arg
                110                 115                 120

ACC GTG CCG CCC TAC TCC CAC CAG TCC AGC GTG TGG TTT GAG ATG ATG    1563
Thr Val Pro Pro Tyr Ser His Gln Ser Ser Val Trp Phe Glu Met Met
            125                 130                 135

CGT GTC TAC AGC TGG AAC CAC ATC ATC CTG CTG GTC AGC GAC GAC CAC    1611
Arg Val Tyr Ser Trp Asn His Ile Ile Leu Leu Val Ser Asp Asp His
        140                 145                 150

GAG GGC CGG GCG GCT CAG AAA CGC CTG GAG ACG CTG CTG GAG GAG CGT    1659
Glu Gly Arg Ala Ala Gln Lys Arg Leu Glu Thr Leu Leu Glu Glu Arg
    155                 160                 165

GAG TCC AAG GCA GAG AAG GTG CTG CAG TTT GAC CCA GGG ACC AAG AAC    1707
Glu Ser Lys Ala Glu Lys Val Leu Gln Phe Asp Pro Gly Thr Lys Asn
```

```
                170                 175                 180                 185
GTG ACG GCC CTG CTG ATG GAG GCG AAA GAG CTG GAG GCC CGG GTC ATC             1755
Val Thr Ala Leu Leu Met Glu Ala Lys Glu Leu Glu Ala Arg Val Ile
                        190                 195                 200

ATC CTT TCT GCC AGC GAG GAC GAT GCT GCC ACT GTA TAC CGC GCA GCC             1803
Ile Leu Ser Ala Ser Glu Asp Asp Ala Ala Thr Val Tyr Arg Ala Ala
                205                 210                 215

GCG ATG CTG AAC ATG ACG GGC TCC GGG TAC GTG TGG CTG GTC GGC GAG             1851
Ala Met Leu Asn Met Thr Gly Ser Gly Tyr Val Trp Leu Val Gly Glu
            220                 225                 230

CGC GAG ATC TCG GGG AAC GCC CTG CGC TAC GCC CCA GAC GGC ATC CTC             1899
Arg Glu Ile Ser Gly Asn Ala Leu Arg Tyr Ala Pro Asp Gly Ile Leu
        235                 240                 245

GGG CTG CAG CTC ATC AAC GGC AAG AAC GAG TCG GCC CAC ATC AGC GAC             1947
Gly Leu Gln Leu Ile Asn Gly Lys Asn Glu Ser Ala His Ile Ser Asp
250                 255                 260                 265

GCC GTG GGC GTG GTG GCC CAG GCC GTG CAC GAG CTC CTC GAG AAG GAG             1995
Ala Val Gly Val Val Ala Gln Ala Val His Glu Leu Leu Glu Lys Glu
                270                 275                 280

AAC ATC ACC GAC CCG CCG CGG GGC TGC GTG GGC AAC ACC AAC ATC TGG             2043
Asn Ile Thr Asp Pro Pro Arg Gly Cys Val Gly Asn Thr Asn Ile Trp
            285                 290                 295

AAG ACC GGG CCG CTC TTC AAG AGA GTG CTG ATG TCT TCC AAG TAT GCG             2091
Lys Thr Gly Pro Leu Phe Lys Arg Val Leu Met Ser Ser Lys Tyr Ala
        300                 305                 310

GAT GGG GTG ACT GGT CGC GTG GAG TTC AAT GAG GAT GGG GAC CGG AAG             2139
Asp Gly Val Thr Gly Arg Val Glu Phe Asn Glu Asp Gly Asp Arg Lys
    315                 320                 325

TTC GCC AAC TAC AGC ATC ATG AAC CTG CAG AAC CGC AAG CTG GTG CAA             2187
Phe Ala Asn Tyr Ser Ile Met Asn Leu Gln Asn Arg Lys Leu Val Gln
330                 335                 340                 345

GTG GGC ATC TAC AAT GGC ACC CAC GTC ATC CCT AAT GAC AGG AAG ATC             2235
Val Gly Ile Tyr Asn Gly Thr His Val Ile Pro Asn Asp Arg Lys Ile
                350                 355                 360

ATC TGG CCA GGC GGA GAG ACA GAG AAG CCT CGA GGG TAC CAG ATG TCC             2283
Ile Trp Pro Gly Gly Glu Thr Glu Lys Pro Arg Gly Tyr Gln Met Ser
            365                 370                 375

ACC AGA CTG AAG ATT GTG ACG ATC CAC CAG GAG CCC TTC GTG TAC GTC             2331
Thr Arg Leu Lys Ile Val Thr Ile His Gln Glu Pro Phe Val Tyr Val
        380                 385                 390

AAG CCC ACG CTG AGT GAT GGG ACA TGC AAG GAG GAG TTC ACA GTC AAC             2379
Lys Pro Thr Leu Ser Asp Gly Thr Cys Lys Glu Glu Phe Thr Val Asn
    395                 400                 405

GGC GAC CCA GTC AAG AAG GTG ATC TGC ACC GGG CCC AAC GAC ACG TCG             2427
Gly Asp Pro Val Lys Lys Val Ile Cys Thr Gly Pro Asn Asp Thr Ser
410                 415                 420                 425

CCG GGC AGC CCC CGC CAC ACG GTG CCT CAG TGT TGC TAC GGC TTT TGC             2475
Pro Gly Ser Pro Arg His Thr Val Pro Gln Cys Cys Tyr Gly Phe Cys
                430                 435                 440

ATC GAC CTG CTC ATC AAG CTG GCA CGG ACC ATG AAC TTC ACC TAC GAG             2523
Ile Asp Leu Leu Ile Lys Leu Ala Arg Thr Met Asn Phe Thr Tyr Glu
            445                 450                 455

GTG CAC CTG GTG GCA GAT GGC AAG TTC GGC ACA CAG GAG CGG GTG AAC             2571
Val His Leu Val Ala Asp Gly Lys Phe Gly Thr Gln Glu Arg Val Asn
        460                 465                 470

AAC AGC AAC AAG AAG GAG TGG AAT GGG ATG ATG GGC GAG CTG CTC AGC             2619
Asn Ser Asn Lys Lys Glu Trp Asn Gly Met Met Gly Glu Leu Leu Ser
    475                 480                 485

GGG CAG GCA GAC ATG ATC GTG GCG CCG CTA ACC ATA AAC AAC GAG CGC             2667
```

-continued

```
Gly Gln Ala Asp Met Ile Val Ala Pro Leu Thr Ile Asn Asn Glu Arg
490                 495                 500                 505

GCG CAG TAC ATC GAG TTT TCC AAG CCC TTC AAG TAC CAG GGC CTG ACT        2715
Ala Gln Tyr Ile Glu Phe Ser Lys Pro Phe Lys Tyr Gln Gly Leu Thr
                    510                 515                 520

ATT CTG GTC AAG AAG GAG ATT CCC CGG AGC ACG CTG GAC TCG TTC ATG        2763
Ile Leu Val Lys Lys Glu Ile Pro Arg Ser Thr Leu Asp Ser Phe Met
                525                 530                 535

CAG CCG TTC CAG AGC ACA CTG TGG CTG CTG GTG GGG CTG TCG GTG CAC        2811
Gln Pro Phe Gln Ser Thr Leu Trp Leu Leu Val Gly Leu Ser Val His
            540                 545                 550

GTG GTG GCC GTG ATG CTG TAC CTG CTG GAC CGC TTC AGC CCC TTC GGC        2859
Val Val Ala Val Met Leu Tyr Leu Leu Asp Arg Phe Ser Pro Phe Gly
        555                 560                 565

CGG TTC AAG GTG AAC AGC GAG GAG GAG GAG GAG GAC GCA CTG ACC CTG        2907
Arg Phe Lys Val Asn Ser Glu Glu Glu Glu Glu Asp Ala Leu Thr Leu
570                 575                 580                 585

TCC TCG GCC ATG TGG TTC TCC TGG GGC GTC CTG CTC AAC TCC GGC ATC        2955
Ser Ser Ala Met Trp Phe Ser Trp Gly Val Leu Leu Asn Ser Gly Ile
                    590                 595                 600

GGG GAA GGC GCC CCC AGA AGC TTC TCA GCG CGC ATC CTG GGC ATG GTG        3003
Gly Glu Gly Ala Pro Arg Ser Phe Ser Ala Arg Ile Leu Gly Met Val
                605                 610                 615

TGG GCC GGC TTT GCC ATG ATC ATC GTG GCC TCC TAC ACC GCC AAC CTG        3051
Trp Ala Gly Phe Ala Met Ile Ile Val Ala Ser Tyr Thr Ala Asn Leu
            620                 625                 630

GCG GCC TTC CTG GTG CTG GAC CGG CCG GAG GAG CGC ATC ACG GGC ATC        3099
Ala Ala Phe Leu Val Leu Asp Arg Pro Glu Glu Arg Ile Thr Gly Ile
        635                 640                 645

AAC GAC CCT CGG CTG AGG AAC CCC TCG GAC AAG TTT ATC TAC GCC ACG        3147
Asn Asp Pro Arg Leu Arg Asn Pro Ser Asp Lys Phe Ile Tyr Ala Thr
650                 655                 660                 665

GTG AAG CAG AGC TCC GTG GAT ATC TAC TTC CGG CGC CAG GTG GAG CTG        3195
Val Lys Gln Ser Ser Val Asp Ile Tyr Phe Arg Arg Gln Val Glu Leu
                    670                 675                 680

AGC ACC ATG TAC CGG CAT ATG GAG AAG CAC AAC TAC GAG AGT GCG GCG        3243
Ser Thr Met Tyr Arg His Met Glu Lys His Asn Tyr Glu Ser Ala Ala
                685                 690                 695

GAG GCC ATC CAG GCC GTG AGA GAC AAC AAG CTG CAT GCC TTC ATC TGG        3291
Glu Ala Ile Gln Ala Val Arg Asp Asn Lys Leu His Ala Phe Ile Trp
            700                 705                 710

GAC TCG GCG GTG CTG GAG TTC GAG GCC TCG CAG AAG TGC GAC CTG GTG        3339
Asp Ser Ala Val Leu Glu Phe Glu Ala Ser Gln Lys Cys Asp Leu Val
        715                 720                 725

ACG ACT GGA GAG CTG TTT TTC CGC TCG GGC TTC GGC ATA GGC ATG CGC        3387
Thr Thr Gly Glu Leu Phe Phe Arg Ser Gly Phe Gly Ile Gly Met Arg
730                 735                 740                 745

AAA GAC AGC CCC TGG AAG CAG AAC GTC TCC CTG TCC ATC CTC AAG TCC        3435
Lys Asp Ser Pro Trp Lys Gln Asn Val Ser Leu Ser Ile Leu Lys Ser
                    750                 755                 760

CAC GAG AAT GGC TTC ATG GAA GAC CTG GAC AAG ACG TGG GTT CGG TAT        3483
His Glu Asn Gly Phe Met Glu Asp Leu Asp Lys Thr Trp Val Arg Tyr
                765                 770                 775

CAG GAA TGT GAC TCG CGC AGC AAC GCC CCT GCG ACC CTT ACT TTT GAG        3531
Gln Glu Cys Asp Ser Arg Ser Asn Ala Pro Ala Thr Leu Thr Phe Glu
            780                 785                 790

AAC ATG GCC GGG GTC TTC ATG CTG GTA GCT GGG GGC ATC GTG GCC GGG        3579
Asn Met Ala Gly Val Phe Met Leu Val Ala Gly Gly Ile Val Ala Gly
        795                 800                 805
```

-continued

```
ATC TTC CTG ATT TTC ATC GAG ATT GCC TAC AAG CGG CAC AAG GAT GCT      3627
Ile Phe Leu Ile Phe Ile Glu Ile Ala Tyr Lys Arg His Lys Asp Ala
810             815                 820                 825

CGG CGG AAG CAG ATG CAG CTG GCC TTT GCC GCC GTT AAC GTG TGG CGG      3675
Arg Arg Lys Gln Met Gln Leu Ala Phe Ala Ala Val Asn Val Trp Arg
                830                 835                 840

AAG AAC CTG CAG CAG TAC CAT CCC ACT GAT ATC ACG GGC CCG CTC AAC      3723
Lys Asn Leu Gln Gln Tyr His Pro Thr Asp Ile Thr Gly Pro Leu Asn
            845                 850                 855

CTC TCA GAT CCC TCG GTC AGC ACC GTG GTG TGAGGCCCCC GGAGGCGCCC        3773
Leu Ser Asp Pro Ser Val Ser Thr Val Val
            860                 865

ACCTGCCCAG TTAGCCCGGC CAAGGACACT GATGGGTCCT GCTGCTCGGG AAGGCCTGAG    3833
GGAAGCCCAC CCGCCCCAGA GACTGCCCAC CCTGGGCCTC CCGTCCGTCC GCCCGCCCAC    3893
CCCGCTGCCT GGCGGGCAGC CCCTGCTGGA CCAAGGTGCG GACCGGAGCG GCTGAGGACG    3953
GGGCAGAGCT GAGTCGGCTG GGCAGGGCGC AGGGCGCTCC GGCAGAGGCA GGGCCCTGGG    4013
GTCTCTGAGC AGTGGGGAGC GGGGGCTAAC TGGCCCCAGG CGAAGGGGCT TGGAGCAGAG    4073
ACGGCAGCCC CATCCTTCCC GCAGCACCAG CCTGAGCCAC AGTGGGGCCC ATGGCCCCAG    4133
CTGGCTGGGT CGCCCCTCCT CGGGCGCCTG CGCTCCTCTG CAGCCTGAGC TCCACCCTCC    4193
CCTCTTCTTG CGGCACCGCC CACCCACACC CCGTCTGCCC CTTGACCCCA CACGCCGGGG    4253
CTGGCCCTGC CCTCCCCCAC GGCCGTCCCT GACTTCCCAG CTGGCAGCGCCTCCCGCCGGC    4313
CTCGGGCCGC CTCCTCCAGA CTCGAGAGGG CTGAGCCCCT CCTCTCCTCG TCCGGCCTGC    4373
AGCCCAGAAC GGGCCTCCCC GGGGGTCCCC GGACGCTGGC TCGGGACTGT CTTCAACCCT    4433
GCCCTGCACC TTGGGCACGG GAGAGCGCCA CCCGCCCGCC CCCGCCCTCG CTCCGGGTGC    4493
GTGACCGGCC CGCCACCTTG TACAGAACCA GCACTCCCAG GGCCCGAGCG CGTGCCTTCC    4553
CCGTGCGGCC CGTGCGCAGC CGCGCTCTGC CCCTCCGTCC CCAGGGTGCA GGCGCGCACC    4613
GCCCAACCCC CACCTCCCGG TGTATGCAGT GGTGATGCCG GAATTC                   4659
```

(2) INFORMATION FOR SEQ ID NO: 10:

(i) SEQUENCE CHARACTERISTICS:
        (A) LENGTH: 885 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Ser Thr Met Arg Leu Leu Thr Leu Ala Leu Leu Phe Ser Cys Ser
-18             -15                 -10                 -5

Val Ala Arg Ala Ala Cys Asp Pro Lys Ile Val Asn Ile Gly Ala Val
                1               5                   10

Leu Ser Thr Arg Lys His Glu Gln Met Phe Arg Glu Ala Val Asn Gln
        15                  20                  25              30

Ala Asn Lys Arg His Gly Ser Trp Lys Ile Gln Leu Asn Ala Thr Ser
                    35                  40                  45

Val Thr His Lys Pro Asn Ala Ile Gln Met Ala Leu Ser Val Cys Glu
                50                  55                  60

Asp Leu Ile Ser Ser Gln Val Tyr Ala Ile Leu Val Ser His Pro Pro
            65                  70                  75

Thr Pro Asn Asp His Phe Thr Pro Thr Pro Val Ser Tyr Thr Ala Gly
        80                  85                  90
```

```
Phe Tyr Arg Ile Pro Val Leu Gly Leu Thr Thr Arg Met Ser Ile Tyr
 95                 100                 105                 110

Ser Asp Lys Ser Ile His Leu Ser Phe Leu Arg Thr Val Pro Pro Tyr
                115                 120                 125

Ser His Gln Ser Ser Val Trp Phe Glu Met Met Arg Val Tyr Ser Trp
            130                 135                 140

Asn His Ile Ile Leu Leu Val Ser Asp His Glu Gly Arg Ala Ala
        145                 150                 155

Gln Lys Arg Leu Glu Thr Leu Leu Glu Glu Arg Glu Ser Lys Ala Glu
    160                 165                 170

Lys Val Leu Gln Phe Asp Pro Gly Thr Lys Asn Val Thr Ala Leu Leu
175                 180                 185                 190

Met Glu Ala Lys Glu Leu Glu Ala Arg Val Ile Ile Leu Ser Ala Ser
                195                 200                 205

Glu Asp Asp Ala Ala Thr Val Tyr Arg Ala Ala Ala Met Leu Asn Met
            210                 215                 220

Thr Gly Ser Gly Tyr Val Trp Leu Val Gly Glu Arg Glu Ile Ser Gly
        225                 230                 235

Asn Ala Leu Arg Tyr Ala Pro Asp Gly Ile Leu Gly Leu Gln Leu Ile
    240                 245                 250

Asn Gly Lys Asn Glu Ser Ala His Ile Ser Asp Ala Val Gly Val Val
255                 260                 265                 270

Ala Gln Ala Val His Glu Leu Leu Glu Lys Glu Asn Ile Thr Asp Pro
                275                 280                 285

Pro Arg Gly Cys Val Gly Asn Thr Asn Ile Trp Lys Thr Gly Pro Leu
            290                 295                 300

Phe Lys Arg Val Leu Met Ser Ser Lys Tyr Ala Asp Gly Val Thr Gly
        305                 310                 315

Arg Val Glu Phe Asn Glu Asp Gly Asp Arg Lys Phe Ala Asn Tyr Ser
    320                 325                 330

Ile Met Asn Leu Gln Asn Arg Lys Leu Val Gln Val Gly Ile Tyr Asn
335                 340                 345                 350

Gly Thr His Val Ile Pro Asn Asp Arg Lys Ile Ile Trp Pro Gly Gly
                355                 360                 365

Glu Thr Glu Lys Pro Arg Gly Tyr Gln Met Ser Thr Arg Leu Lys Ile
            370                 375                 380

Val Thr Ile His Gln Glu Pro Phe Val Tyr Val Lys Pro Thr Leu Ser
        385                 390                 395

Asp Gly Thr Cys Lys Glu Glu Phe Thr Val Asn Gly Asp Pro Val Lys
    400                 405                 410

Lys Val Ile Cys Thr Gly Pro Asn Asp Thr Ser Pro Gly Ser Pro Arg
415                 420                 425                 430

His Thr Val Pro Gln Cys Cys Tyr Gly Phe Cys Ile Asp Leu Leu Ile
                435                 440                 445

Lys Leu Ala Arg Thr Met Asn Phe Thr Tyr Glu Val His Leu Val Ala
            450                 455                 460

Asp Gly Lys Phe Gly Thr Gln Glu Arg Val Asn Asn Ser Asn Lys Lys
        465                 470                 475

Glu Trp Asn Gly Met Met Gly Glu Leu Leu Ser Gly Gln Ala Asp Met
    480                 485                 490

Ile Val Ala Pro Leu Thr Ile Asn Asn Glu Arg Ala Gln Tyr Ile Glu
495                 500                 505                 510

Phe Ser Lys Pro Phe Lys Tyr Gln Gly Leu Thr Ile Leu Val Lys Lys
```

-continued

```
                515              520              525
Glu Ile Pro Arg Ser Thr Leu Asp Ser Phe Met Gln Pro Phe Gln Ser
                530              535              540
Thr Leu Trp Leu Leu Val Gly Leu Ser Val His Val Val Ala Val Met
            545              550              555
Leu Tyr Leu Leu Asp Arg Phe Ser Pro Phe Gly Arg Phe Lys Val Asn
            560              565              570
Ser Glu Glu Glu Glu Asp Ala Leu Thr Leu Ser Ser Ala Met Trp
575              580              585              590
Phe Ser Trp Gly Val Leu Leu Asn Ser Gly Ile Gly Glu Gly Ala Pro
                595              600              605
Arg Ser Phe Ser Ala Arg Ile Leu Gly Met Val Trp Ala Gly Phe Ala
            610              615              620
Met Ile Ile Val Ala Ser Tyr Thr Ala Asn Leu Ala Ala Phe Leu Val
            625              630              635
Leu Asp Arg Pro Glu Glu Arg Ile Thr Gly Ile Asn Asp Pro Arg Leu
            640              645              650
Arg Asn Pro Ser Asp Lys Phe Ile Tyr Ala Thr Val Lys Gln Ser Ser
655              660              665              670
Val Asp Ile Tyr Phe Arg Arg Gln Val Glu Leu Ser Thr Met Tyr Arg
                675              680              685
His Met Glu Lys His Asn Tyr Glu Ser Ala Ala Glu Ala Ile Gln Ala
            690              695              700
Val Arg Asp Asn Lys Leu His Ala Phe Ile Trp Asp Ser Ala Val Leu
            705              710              715
Glu Phe Glu Ala Ser Gln Lys Cys Asp Leu Val Thr Thr Gly Glu Leu
            720              725              730
Phe Phe Arg Ser Gly Phe Gly Ile Gly Met Arg Lys Asp Ser Pro Trp
735              740              745              750
Lys Gln Asn Val Ser Leu Ser Ile Leu Lys Ser His Glu Asn Gly Phe
                755              760              765
Met Glu Asp Leu Asp Lys Thr Trp Val Arg Tyr Gln Glu Cys Asp Ser
            770              775              780
Arg Ser Asn Ala Pro Ala Thr Leu Thr Phe Glu Asn Met Ala Gly Val
            785              790              795
Phe Met Leu Val Ala Gly Gly Ile Val Ala Gly Ile Phe Leu Ile Phe
            800              805              810
Ile Glu Ile Ala Tyr Lys Arg His Lys Asp Ala Arg Arg Lys Gln Met
815              820              825              830
Gln Leu Ala Phe Ala Ala Val Asn Val Trp Arg Lys Asn Leu Gln Gln
                835              840              845
Tyr His Pro Thr Asp Ile Thr Gly Pro Leu Asn Leu Ser Asp Pro Ser
            850              855              860
Val Ser Thr Val Val
        865

(2) INFORMATION FOR SEQ ID NO: 11:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: cDNA
```

(xi) SEQUENCE DESCRIPTION: SEQ ID NO: 11:

GAAGAACCTG CAGCAGTACC ATCCCACT                                              28

(2) INFORMATION FOR SEQ ID NO: 12:

(i) SEQUENCE CHARACTERISTICS:
        (A) LENGTH: 391 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 12:

GAAGAACCTG CAGAGCACCG GGGGTGGACG CGGCGCTTTG CAAAACCAAA AAGACACAGT           60

GCTGCCGCGA CGCGCTATTG AGAGGGAGGA GGGCCAGCTG CAGCTGTGTT CCCGTCATAG          120

GGAGAGCTGA GACTCCCCGC CGCCCTCCT CTGCCCCCTC CCCCGCAGAC AGACAGACAG           180

ACGGATGGGA CAGCGGCCCG GCCCACGCAG AGCCCCGGAG CACCACGGGG TCGGGGAGG           240

AGCACCCCCA GCCTCCCCCA GGCTGCGCCT GCCCGCCCGC CGGTTGGCCG GCTGGCCGGT          300

CCACCCCGTC CCGGCCCCGC GCGTGCCCCC AGCGTGGGGC TAACGGGCGC CTTGTCTGTG          360

TATTTCTATT TTGCAGCAGT ACCATCCCAC T                                         391

(2) INFORMATION FOR SEQ ID NO: 13:

(i) SEQUENCE CHARACTERISTICS:
        (A) LENGTH: 502 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 13:

GAAGAACCTG CAGGATAGAA AGAGTGGTAG AGCAGAGCCT GACCCTAAAA AGAAAGCCAC           60

ATTTAGGGCT ATCACCTCCA CCCTGGCTTC CAGCTTCAAG AGGCGTAGGT CCTCCAAAGA          120

CACGAGCACC GGGGGTGGAC GCGGCGCTTT GCAAAACCAA AAAGACACAG TGCTGCCGCG          180

ACGCGCTATT GAGAGGGAGG AGGGCCAGCT GCAGCTGTGT TCCCGTCATA GGGAGAGCTG          240

AGACTCCCCG CCCGCCCTCC TCTGCCCCCT CCCCCGCAGA CAGACAGACA GACGGATGGG          300

ACAGCGGCCC GGCCCACGCA GAGCCCCGGA GCACCACGGG GTCGGGGGAG GAGCACCCCC          360

AGCCTCCCCC AGGCTGCGCC TGCCCGCCCG CCGGTTGGCC GGCTGGCCGG TCCACCCCGT          420

CCCGGCCCCG CGCGTGCCCC CAGCGTGGGG CTAACGGGCG CCTTGTCTGT GTATTTCTAT          480

TTTGCAGCAG TACCATCCCA CT                                                  502

(2) INFORMATION FOR SEQ ID NO: 14:

(i) SEQUENCE CHARACTERISTICS:
        (A) LENGTH: 502 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 14:

GAAGAACCTG CAGGATAGAA AGAGTGGTAG AGCAGAGCCT GACCCTAAAA AGAAAGCCAC           60

ATTTAGGGCT ATCACCTCCA CCCTGGCTTC CAGCTTCAAG AGGCGTAGGT CCTCCAAAGA          120

```
CACGAGCACC GGGGGTGGAC GCGGCGCTTT GCAAAACCAA AAAGACACAG TGCTGCCGCG    180

ACGCGCTATT GAGAGGGAGG AGGGCCAGCT GCAGCTGTGT TCCCGTCATA GGGAGAGCTG    240

AGACTCCCCG CCCGCCCTCC TCTGCCCCCT CCCCCGCAGA CAGACAGACA GACGGATGGG    300

ACAGCGGCCC GGCCCACGCA GAGCCCCGGA GCACCACGGG GTCGGGGGAG GAGCACCCCC    360

AGCCTCCCCC AGGCTGCGCC TGCCCGCCCG CCGGTTGGCC GGCTGGCCGG TCCACCCCGT    420

CCCGGCCCCG CGCGTGCCCC CAGCGTGGGG CTAACGGGCG CCTTGTCTGT GTATTTCTAT    480

TTTGCAGCAG TACCATCCCA CT                                            502
```

(2) INFORMATION FOR SEQ ID NO: 15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 15:

```
GGGGTTTGGA TCCAAAGAAT GGAACGGAAT GATG                                34
```

(2) INFORMATION FOR SEQ ID NO: 16:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 16:

```
GGGGTTTAAG CTTCTCGTAG TTGTGCTTCT CCAT                                34
```

(2) INFORMATION FOR SEQ ID NO: 17:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (xi) SEQUENCE DESCRIPTION: SEQ ID NO: 17:

```
Ala Gly Gly Ile Val Ala Gly Ile Phe Leu Ile Phe Ile Glu Ile Ala
 1               5                  10                  15

Tyr Lys Arg His Lys Asp Ala Arg Arg Lys Gln Met Gln Leu Ala Phe
            20                  25                  30

Ala Ala Val Asn Val Trp Arg Lys Asn Leu Gln Gln Tyr His Pro Thr
        35                  40                  45

Asp Ile Thr Gly Pro Leu Asn Leu Ser Asp Pro Ser Val Ser Thr Val
    50                  55                  60

Val
 65
```

(2) INFORMATION FOR SEQ ID NO: 18:

(i) SEQUENCE CHARACTERISTICS:
        (A) LENGTH: 102 amino acids
        (B) TYPE: amino acid
        (D) TOPOLOGY: linear (ii) MOLECULE TYPE: peptide (xi) SEQUENCE DESCRIPTION: SEQ ID NO: 18:

```
Ala Gly Gly Ile Val Ala Gly Ile Phe Leu Ile Phe Ile Glu Ile Ala
 1               5                  10                  15

Tyr Lys Arg His Lys Asp Ala Arg Arg Lys Gln Met Gln Leu Ala Phe
             20                  25                  30

Ala Ala Val Asn Val Trp Arg Lys Asn Leu Gln Asp Arg Lys Ser Gly
         35                  40                  45

Arg Ala Glu Pro Asp Pro Lys Lys Lys Ala Thr Phe Arg Ala Ile Thr
     50                  55                  60

Ser Thr Leu Ala Ser Ser Phe Lys Arg Arg Ser Ser Lys Asp Thr
 65                  70                  75              80

Gln Tyr His Pro Thr Asp Ile Thr Gly Pro Leu Asn Leu Ser Asp Pro
             85                  90                  95

Ser Val Ser Thr Val Val
            100

(2) INFORMATION FOR SEQ ID NO: 19:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO: 19:

Lys Arg Leu Glu Thr Leu Leu Glu Glu Arg Glu Ser Lys Ser Lys Lys
 1               5                  10                  15

Arg Asn Tyr Glu Asn Leu Asp Gln Leu Ser Tyr Asp Asn Lys Arg Gly
             20                  25                  30

Pro Lys Ala Glu Lys Val Leu Gln Phe Asp Pro Gly Thr Lys Asn
         35                  40                  45

(2) INFORMATION FOR SEQ ID NO: 20:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO: 20:

Lys Arg Leu Glu Thr Leu Leu Glu Glu Arg Glu Ser Lys Ala Glu Lys
 1               5                  10                  15

Val Leu Gln Phe Asp Pro Gly Thr Lys Asn
             20                  25

(2) INFORMATION FOR SEQ ID NO: 21:

(i) SEQUENCE CHARACTERISTICS:
        (A) LENGTH: 927 amino acids
        (B) TYPE: amino acid
        (D) TOPOLOGY: linear (ii) MOLECULE TYPE: protein (xi) SEQUENCE DESCRIPTION: SEQ ID NO: 21:

Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
```

-continued

```
            35                  40                  45
Ala Asn Lys Arg His Gly Ser Trp Lys Ile Gln Leu Asn Ala Thr Ser
 50                  55                  60

Val Thr His Lys Pro Asn Ala Ile Gln Met Ala Leu Ser Val Cys Gly
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
                100                 105                 110

Phe Tyr Arg Ile Pro Val Leu Gly Leu Thr Thr Arg Met Ser Ile Tyr
                115                 120                 125

Ser Asp Lys Ser Ile His Leu Ser Phe Leu Arg Thr Val Pro Pro Typ
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
                180                 185                 190

Lys Val Leu Gln Phe Asp Pro Gly Thr Lys Asn Val Thr Ala Leu Leu
                195                 200                 205

Met Glu Ala Lys Glu Leu Glu Ala Arg Val Ile Ile Leu Ser Ala Ser
210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
                260                 265                 270

Asn Gly Lys Asn Glu Ser Ala His Ile Ser Asp Ala Val Gly Val Val
                275                 280                 285

Ala Gln Ala Val His Glu Leu Leu Glu Lys Glu Asn Ile Thr Asp Pro
                290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
                340                 345                 350

Ile Met Asn Leu Gln Asn Arg Lys Leu Val Gln Val Gly Ile Tyr Asn
                355                 360                 365

Gly Thr His Val Ile Pro Asn Asp Arg Lys Ile Ile Trp Pro Gly Gly
                370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
                420                 425                 430

Lys Val Ile Cys Thr Gly Pro Asn Asp Thr Ser Pro Gly Ser Pro Arg
                435                 440                 445

His Thr Val Pro Gln Cys Cys Tyr Gly Phe Cys Ile Asp Leu Leu Ile
                450                 455                 460
```

-continued

```
Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
            485                 490                 495

Glu Trp Asn Gly Met Met Gly Glu Leu Leu Ser Gly Gln Ala Asp Met
                500                 505                 510

Ile Val Ala Pro Leu Thr Ile Asn Asn Glu Arg Ala Gln Tyr Ile Glu
                515                 520                 525

Phe Ser Lys Pro Phe Lys Tyr Gln Gly Leu Thr Ile Leu Val Lys Lys
            530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Asp Ala Leu Thr Leu Ser Ser Ala Met Trp
            595                 600                 605

Phe Ser Trp Gly Val Leu Leu Asn Ser Gly Ile Gly Glu Gly Ala Pro
            610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
            675                 680                 685

Val Asp Ile Tyr Phe Arg Arg Gln Val Glu Leu Ser Thr Met Tyr Arg
            690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
                740                 745                 750

Phe Phe Arg Ser Gly Phe Gly Ile Gly Met Arg Lys Asp Ser Pro Trp
            755                 760                 765

Lys Gln Asn Val Ser Leu Ser Ile Leu Lys Ser His Glu Asn Gly Phe
            770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
                835                 840                 845

Gln Leu Ala Phe Ala Ala Val Asn Val Trp Arg Lys Asn Leu Gln Gln
            850                 855                 860

Tyr His Pro Thr Asp Ile Thr Gly Pro Leu Asn Leu Ser Asp Pro Ser
865                 870                 875                 880
```

```
Val Ser Thr Val Val Lys Asn Leu Gln Ser Thr Gly Gly Gly Arg Gly
                885                 890                 895

Ala Leu Gln Asn Gln Lys Asp Thr Val Leu Pro Arg Arg Ala Ile Glu
            900                 905                 910

Arg Glu Glu Gly Gln Leu Gln Leu Cys Ser Arg His Arg Glu Ser
        915                 920                 925
```

(2) INFORMATION FOR SEQ ID NO: 22:

(i) SEQUENCE CHARACTERISTICS:
        (A) LENGTH: 964 amino acids
        (B) TYPE: amino acid
        (D) TOPOLOGY: linear (ii) MOLECULE TYPE: protein (xi) SEQUENCE DESCRIPTION: SEQ ID NO: 22:

```
Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
```

```
                305                 310                 315                 320
        Phe Lys Arg Val Leu Met Ser Ser Lys Tyr Ala Asp Gly Val Thr Gly
                        325                 330                 335

Arg Val Glu Phe Asn Glu Asp Gly Asp Arg Lys Phe Ala Asn Tyr Ser
                        340                 345                 350

Ile Met Asn Leu Gln Asn Arg Lys Leu Val Gln Val Gly Ile Tyr Asn
                        355                 360                 365

Gly Thr His Val Ile Pro Asn Asp Arg Lys Ile Ile Trp Pro Gly Gly
                        370                 375                 380

Glu Thr Glu Lys Pro Arg Gly Tyr Gln Met Ser Thr Arg Leu Lys Ile
        385                 390                 395                 400

Val Thr Ile His Gln Glu Pro Phe Val Tyr Val Lys Pro Thr Leu Ser
                        405                 410                 415

Asp Gly Thr Cys Lys Glu Glu Phe Thr Val Asn Gly Asp Pro Val Lys
                        420                 425                 430

Lys Val Ile Cys Thr Gly Pro Asn Asp Thr Ser Pro Gly Ser Pro Arg
                        435                 440                 445

His Thr Val Pro Gln Cys Cys Tyr Gly Phe Cys Ile Asp Leu Leu Ile
                        450                 455                 460

Lys Leu Ala Arg Thr Met Asn Phe Thr Tyr Glu Val His Leu Val Ala
        465                 470                 475                 480

Asp Gly Lys Phe Gly Thr Gln Glu Arg Val Asn Asn Ser Asn Lys Lys
                        485                 490                 495

Glu Trp Asn Gly Met Met Gly Glu Leu Leu Ser Gly Gln Ala Asp Met
                        500                 505                 510

Ile Val Ala Pro Leu Thr Ile Asn Asn Glu Arg Ala Gln Tyr Ile Glu
                        515                 520                 525

Phe Ser Lys Pro Phe Lys Tyr Gln Gly Leu Thr Ile Leu Val Lys Lys
                        530                 535                 540

Glu Ile Pro Arg Ser Thr Leu Asp Ser Phe Met Gln Pro Phe Gln Ser
        545                 550                 555                 560

Thr Leu Trp Leu Leu Val Gly Leu Ser Val His Val Val Ala Val Met
                        565                 570                 575

Leu Tyr Leu Leu Asp Arg Phe Ser Pro Phe Gly Arg Phe Lys Val Asn
                        580                 585                 590

Ser Glu Glu Glu Glu Asp Ala Leu Thr Leu Ser Ser Ala Met Trp
                        595                 600                 605

Phe Ser Trp Gly Val Leu Leu Asn Ser Gly Ile Gly Glu Gly Ala Pro
        610                 615                 620

Arg Ser Phe Ser Ala Arg Ile Leu Gly Met Val Trp Ala Gly Phe Ala
        625                 630                 635                 640

Met Ile Ile Val Ala Ser Tyr Thr Ala Asn Leu Ala Ala Phe Leu Val
                        645                 650                 655

Leu Asp Arg Pro Glu Glu Arg Ile Thr Gly Ile Asn Asp Pro Arg Leu
                        660                 665                 670

Arg Asn Pro Ser Asp Lys Phe Ile Tyr Ala Thr Val Lys Gln Ser Ser
                        675                 680                 685

Val Asp Ile Tyr Phe Arg Arg Gln Val Glu Leu Ser Thr Met Tyr Arg
                        690                 695                 700

His Met Glu Lys His Asn Tyr Glu Ser Ala Ala Glu Ala Ile Gln Ala
        705                 710                 715                 720

Val Arg Asp Asn Lys Leu His Ala Phe Ile Trp Asp Ser Ala Val Leu
                        725                 730                 735
```

```
Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
        770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
            835                 840                 845

Gln Leu Ala Phe Ala Ala Val Asn Val Trp Arg Lys Asn Leu Gln Gln
            850                 855                 860

Tyr His Pro Thr Asp Ile Thr Gly Pro Leu Asn Leu Ser Asp Pro Ser
865                 870                 875                 880

Val Ser Thr Val Val Lys Asn Leu Gln Asp Arg Lys Ser Gly Arg Ala
                885                 890                 895

Glu Pro Asp Pro Lys Lys Lys Ala Thr Phe Arg Ala Ile Thr Ser Thr
                900                 905                 910

Leu Ala Ser Ser Phe Lys Arg Arg Ser Ser Lys Asp Thr Ser Thr
            915                 920                 925

Gly Gly Gly Arg Gly Ala Leu Gln Asn Gln Lys Asp Thr Val Leu Pro
            930                 935                 940

Arg Arg Ala Ile Glu Arg Glu Glu Gly Gln Leu Gln Leu Cys Ser Arg
945                 950                 955                 960

His Arg Glu Ser (2) INFORMATION FOR SEQ ID NO: 23:

(i) SEQUENCE CHARACTERISTICS:
        (A) LENGTH: 964 amino acids
        (B) TYPE: amino acid
        (D) TOPOLOGY: linear (ii) MOLECULE TYPE: protein (xi) SEQUENCE DESCRIPTION: SEQ ID NO: 23:

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
            50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
                100                 105                 110

Phe Tyr Arg Ile Pro Val Leu Gly Leu Thr Thr Arg Met Ser Ile Tyr
```

```
              115                 120                 125
Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Glu Glu Arg Glu Ser Lys Ala Glu
            180                 185                 190

Lys Val Leu Gln Phe Asp Pro Gly Thr Lys Asn Val Thr Ala Leu Leu
            195                 200                 205

Met Glu Ala Lys Glu Leu Glu Ala Arg Val Ile Ile Leu Ser Ala Ser
210                 215                 220

Glu Asp Asp Ala Ala Thr Val Tyr Arg Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
            275                 280                 285

Ala Gln Ala Val His Glu Leu Leu Glu Lys Glu Asn Ile Thr Asp Pro
290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
            325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
            355                 360                 365

Gly Thr His Val Ile Pro Asn Asp Arg Lys Ile Ile Trp Pro Gly Gly
            370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
            435                 440                 445

His Thr Val Pro Gln Cys Cys Tyr Gly Phe Cys Ile Asp Leu Leu Ile
450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
            485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
            515                 520                 525

Phe Ser Lys Pro Phe Lys Tyr Gln Gly Leu Thr Ile Leu Val Lys Lys
530                 535                 540
```

```
Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Ala Val Met
                565                 570                 575

Leu Tyr Leu Leu Asp Arg Phe Ser Pro Phe Gly Arg Phe Lys Val Asn
                580                 585                 590

Ser Glu Glu Glu Glu Asp Ala Leu Thr Leu Ser Ser Ala Met Trp
                595                 600                 605

Phe Ser Trp Gly Val Leu Leu Asn Ser Gly Ile Gly Glu Gly Ala Pro
                610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
                660                 665                 670

Arg Asn Pro Ser Asp Lys Phe Ile Tyr Ala Thr Val Lys Gln Ser Ser
                675                 680                 685

Val Asp Ile Tyr Phe Arg Arg Gln Val Glu Leu Ser Thr Met Tyr Arg
690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
                740                 745                 750

Phe Phe Arg Ser Gly Phe Gly Ile Gly Met Arg Lys Asp Ser Pro Trp
                755                 760                 765

Lys Gln Asn Val Ser Leu Ser Ile Leu Lys Ser His Glu Asn Gly Phe
                770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
                835                 840                 845

Gln Leu Ala Phe Ala Ala Val Asn Val Trp Arg Lys Asn Leu Gln Gln
850                 855                 860

Tyr His Pro Thr Asp Ile Thr Gly Pro Leu Asn Leu Ser Asp Pro Ser
865                 870                 875                 880

Val Ser Thr Val Val Lys Asn Leu Gln Asp Arg Lys Ser Gly Arg Ala
                885                 890                 895

Glu Pro Asp Pro Lys Lys Lys Ala Thr Phe Arg Ala Ile Thr Ser Thr
                900                 905                 910

Leu Ala Ser Ser Phe Lys Arg Arg Ser Ser Lys Asp Thr Ser Thr
                915                 920                 925

Gly Gly Gly Arg Gly Ala Leu Gln Asn Gln Lys Asp Thr Val Leu Pro
                930                 935                 940

Arg Arg Ala Ile Glu Arg Glu Glu Gly Gln Leu Gln Leu Cys Ser Arg
945                 950                 955                 960
```

-continued

```
His Arg Glu Ser (2) INFORMATION FOR SEQ ID NO: 24:

(i) SEQUENCE CHARACTERISTICS:
         (A) LENGTH: 922 amino acids
         (B) TYPE: amino acid
         (C) STRANDEDNESS: <Unknown>
         (D) TOPOLOGY: linear (ii) MOLECULE TYPE: protein (xi) SEQUENCE DESCRIPTION: SEQ ID NO: 24:

Met Ser Thr Met Arg Leu Leu Thr Leu Ala Leu Leu Phe Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
            115                 120                 125

Ser Asp Lys Ser Ile His Leu Ser Phe Leu Arg Thr Val Pro Pro Tyr
        130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
            195                 200                 205

Met Glu Ala Lys Glu Leu Glu Ala Arg Val Ile Ile Leu Ser Ala Ser
        210                 215                 220

Glu Asp Asp Ala Ala Thr Val Tyr Arg Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
            275                 280                 285

Ala Gln Ala Val His Glu Leu Leu Glu Lys Glu Asn Ile Thr Asp Pro
        290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
```

```
                340             345             350
Ile Met Asn Leu Gln Asn Arg Lys Leu Val Gln Val Gly Ile Tyr Asn
            355             360             365
Gly Thr His Val Ile Pro Asn Asp Arg Lys Ile Ile Trp Pro Gly Gly
    370             375             380
Glu Thr Glu Lys Pro Arg Gly Tyr Gln Met Ser Thr Arg Leu Lys Ile
385             390             395             400
Val Thr Ile His Gln Glu Pro Phe Val Tyr Val Lys Pro Thr Leu Ser
            405             410             415
Asp Gly Thr Cys Lys Glu Glu Phe Thr Val Asn Gly Asp Pro Val Lys
            420             425             430
Lys Val Ile Cys Thr Gly Pro Asn Asp Thr Ser Pro Gly Ser Pro Arg
            435             440             445
His Thr Val Pro Gln Cys Cys Tyr Gly Phe Cys Ile Asp Leu Leu Ile
            450             455             460
Lys Leu Ala Arg Thr Met Asn Phe Thr Tyr Glu Val His Leu Val Ala
465             470             475             480
Asp Gly Lys Phe Gly Thr Gln Glu Arg Val Asn Asn Ser Asn Lys Lys
            485             490             495
Glu Trp Asn Gly Met Met Gly Glu Leu Leu Ser Gly Gln Ala Asp Met
            500             505             510
Ile Val Ala Pro Leu Thr Ile Asn Asn Glu Arg Ala Gln Tyr Ile Glu
            515             520             525
Phe Ser Lys Pro Phe Lys Tyr Gln Gly Leu Thr Ile Leu Val Lys Lys
            530             535             540
Glu Ile Pro Arg Ser Thr Leu Asp Ser Phe Met Gln Pro Phe Gln Ser
545             550             555             560
Thr Leu Trp Leu Leu Val Gly Leu Ser Val His Val Val Ala Val Met
            565             570             575
Leu Tyr Leu Leu Asp Arg Phe Ser Pro Phe Gly Arg Phe Lys Val Asn
            580             585             590
Ser Glu Glu Glu Glu Asp Ala Leu Thr Leu Ser Ser Ala Met Trp
            595             600             605
Phe Ser Trp Gly Val Leu Leu Asn Ser Gly Ile Gly Glu Gly Ala Pro
            610             615             620
Arg Ser Phe Ser Ala Arg Ile Leu Gly Met Val Trp Ala Gly Phe Ala
625             630             635             640
Met Ile Ile Val Ala Ser Tyr Thr Ala Asn Leu Ala Ala Phe Leu Val
            645             650             655
Leu Asp Arg Pro Glu Glu Arg Ile Thr Gly Ile Asn Asp Pro Arg Leu
            660             665             670
Arg Asn Pro Ser Asp Lys Phe Ile Tyr Ala Thr Val Lys Gln Ser Ser
            675             680             685
Val Asp Ile Tyr Phe Arg Arg Gln Val Glu Leu Ser Thr Met Tyr Arg
            690             695             700
His Met Glu Lys His Asn Tyr Glu Ser Ala Ala Glu Ala Ile Gln Ala
705             710             715             720
Val Arg Asp Asn Lys Leu His Ala Phe Ile Trp Asp Ser Ala Val Leu
            725             730             735
Glu Phe Glu Ala Ser Gln Lys Cys Asp Leu Val Thr Thr Gly Glu Leu
            740             745             750
Phe Phe Arg Ser Gly Phe Gly Ile Gly Met Arg Lys Asp Ser Pro Trp
            755             760             765
```

```
Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
            835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Gln Tyr His Pro Thr Asp Ile Thr Gly Pro Leu Asn
                900                 905                 910

Leu Ser Asp Pro Ser Val Ser Thr Val Val
            915                 920

(2) INFORMATION FOR SEQ ID NO: 25:

(i) SEQUENCE CHARACTERISTICS:
        (A) LENGTH: 906 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 25:

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
    115                 120                 125

Ser Asp Lys Ser Ile His Leu Ser Phe Leu Arg Thr Val Pro Pro Tyr
            130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190
```

-continued

```
Lys Arg Asn Tyr Glu Asn Leu Asp Gln Leu Ser Tyr Asp Asn Lys Arg
            195                 200                 205
Gly Pro Lys Ala Glu Lys Val Leu Gln Phe Asp Pro Gly Thr Lys Asn
        210                 215                 220
Val Thr Ala Leu Leu Met Glu Ala Lys Glu Leu Glu Ala Arg Val Ile
225                 230                 235                 240
Ile Leu Ser Ala Ser Glu Asp Ala Ala Thr Val Tyr Arg Ala Ala
                245                 250                 255
Ala Met Leu Asn Met Thr Gly Ser Gly Tyr Val Trp Leu Val Gly Glu
            260                 265                 270
Arg Glu Ile Ser Gly Asn Ala Leu Arg Tyr Ala Pro Asp Gly Ile Leu
        275                 280                 285
Gly Leu Gln Leu Ile Asn Gly Lys Asn Glu Ser Ala His Ile Ser Asp
        290                 295                 300
Ala Val Gly Val Val Ala Gln Ala Val His Glu Leu Leu Glu Lys Glu
305                 310                 315                 320
Asn Ile Thr Asp Pro Pro Arg Gly Cys Val Gly Asn Thr Asn Ile Trp
                325                 330                 335
Lys Thr Gly Pro Leu Phe Lys Arg Val Leu Met Ser Ser Lys Tyr Ala
            340                 345                 350
Asp Gly Val Thr Gly Arg Val Glu Phe Asn Glu Asp Gly Asp Arg Lys
        355                 360                 365
Phe Ala Asn Tyr Ser Ile Met Asn Leu Gln Asn Arg Lys Leu Val Gln
        370                 375                 380
Val Gly Ile Tyr Asn Gly Thr His Val Ile Pro Asn Asp Arg Lys Ile
385                 390                 395                 400
Ile Trp Pro Gly Gly Glu Thr Glu Lys Pro Arg Gly Tyr Gln Met Ser
                405                 410                 415
Thr Arg Leu Lys Ile Val Thr Ile His Gln Glu Pro Phe Val Tyr Val
            420                 425                 430
Lys Pro Thr Leu Ser Asp Gly Thr Cys Lys Glu Glu Phe Thr Val Asn
        435                 440                 445
Gly Asp Pro Val Lys Lys Val Ile Cys Thr Gly Pro Asn Asp Thr Ser
        450                 455                 460
Pro Gly Ser Pro Arg His Thr Val Pro Gln Cys Cys Tyr Gly Phe Cys
465                 470                 475                 480
Ile Asp Leu Leu Ile Lys Leu Ala Arg Thr Met Asn Phe Thr Tyr Glu
                485                 490                 495
Val His Leu Val Ala Asp Gly Lys Phe Gly Thr Gln Glu Arg Val Asn
            500                 505                 510
Asn Ser Asn Lys Lys Glu Trp Asn Gly Met Met Gly Glu Leu Leu Ser
        515                 520                 525
Gly Gln Ala Asp Met Ile Val Ala Pro Leu Thr Ile Asn Asn Glu Arg
        530                 535                 540
Ala Gln Tyr Ile Glu Phe Ser Lys Pro Phe Lys Tyr Gln Gly Leu Thr
545                 550                 555                 560
Ile Leu Val Lys Lys Glu Ile Pro Arg Ser Thr Leu Asp Ser Phe Met
                565                 570                 575
Gln Pro Phe Gln Ser Thr Leu Trp Leu Leu Val Gly Leu Ser Val His
            580                 585                 590
Val Val Ala Val Met Leu Tyr Leu Leu Asp Arg Phe Ser Pro Phe Gly
        595                 600                 605
```

```
Arg Phe Lys Val Asn Ser Glu Glu Glu Glu Asp Ala Leu Thr Leu
    610                 615                 620

Ser Ser Ala Met Trp Phe Ser Trp Gly Val Leu Leu Asn Ser Gly Ile
625                 630                 635                 640

Gly Glu Gly Ala Pro Arg Ser Phe Ser Ala Arg Ile Leu Gly Met Val
                645                 650                 655

Trp Ala Gly Phe Ala Met Ile Ile Val Ala Ser Tyr Thr Ala Asn Leu
                660                 665                 670

Ala Ala Phe Leu Val Leu Asp Arg Pro Glu Glu Arg Ile Thr Gly Ile
                675                 680                 685

Asn Asp Pro Arg Leu Arg Asn Pro Ser Asp Lys Phe Ile Tyr Ala Thr
                690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
                740                 745                 750

Asp Ser Ala Val Leu Glu Phe Glu Ala Ser Gln Lys Cys Asp Leu Val
                755                 760                 765

Thr Thr Gly Glu Leu Phe Phe Arg Ser Gly Phe Gly Ile Gly Met Arg
                770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
                805                 810                 815

Gln Glu Cys Asp Ser Arg Ser Asn Ala Pro Ala Thr Leu Thr Phe Glu
                820                 825                 830

Asn Met Ala Gly Val Phe Met Leu Val Ala Gly Gly Ile Val Ala Gly
                835                 840                 845

Ile Phe Leu Ile Phe Ile Glu Ile Ala Tyr Lys Arg His Lys Asp Ala
                850                 855                 860

Arg Arg Lys Gln Met Gln Leu Ala Phe Ala Ala Val Asn Val Trp Arg
865                 870                 875                 880

Lys Asn Leu Gln Gln Tyr His Pro Thr Asp Ile Thr Gly Pro Leu Asn
                885                 890                 895

Leu Ser Asp Pro Ser Val Ser Thr Val Val
                900                 905

(2) INFORMATION FOR SEQ ID NO: 26:

(i) SEQUENCE CHARACTERISTICS:
        (A) LENGTH: 948 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 26:

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gla
                35                  40                  45
```

-continued

```
Ala Asn Lys Arg His Gly Ser Trp Lys Ile Gln Leu Asn Ala Thr Ser
 50                  55                  60

Val Thr His Lys Pro Asn Ala Ile Gln Met Ala Leu Ser Val Cys Glu
65                   70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Ser Gly Tyr Val Trp Leu Val Gly Glu
            260                 265                 270

Arg Glu Ile Ser Gly Asn Ala Leu Arg Tyr Ala Pro Asp Gly Ile Leu
        275                 280                 285

Gly Leu Gln Leu Ile Asn Gly Lys Asn Glu Ser Ala His Ile Ser Asn
290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
            340                 345                 350

Asp Gly Val Thr Gly Arg Val Glu Phe Asn Glu Asp Gly Asp Arg Lys
        355                 360                 365

Phe Ala Asn Tyr Ser Ile Met Asn Leu Gln Asn Arg Lys Leu Val Gln
370                 375                 380

Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Glu Phe Thr Val Asn
        435                 440                 445

Gly Asp Pro Val Lys Lys Val Ile Cys Thr Gly Pro Asn Asp Thr Ser
450                 455                 460

Pro Gly Ser Pro Arg His Thr Val Pro Gln Cys Cys Tyr Gly Phe Cys
```

```
                465                 470                 475                 480
        Ile Asp Leu Leu Ile Lys Leu Ala Arg Thr Met Asn Phe Thr Tyr Glu
                        485                 490                 495

Val His Leu Val Ala Asp Gly Lys Phe Gly Thr Gln Glu Arg Val Asn
                        500                 505                 510

Asn Ser Asn Lys Lys Glu Trp Asn Gly Met Met Gly Glu Leu Leu Ser
                        515                 520                 525

Gly Gln Ala Asp Met Ile Val Ala Pro Leu Thr Ile Asn Asn Glu Arg
                530                 535                 540

Ala Gln Tyr Ile Glu Phe Ser Lys Pro Phe Lys Tyr Gln Gly Leu Thr
        545                 550                 555                 560

Ile Leu Val Lys Lys Glu Ile Pro Arg Ser Thr Leu Asp Ser Phe Met
                        565                 570                 575

Gln Pro Phe Gln Ser Thr Leu Trp Leu Leu Val Gly Leu Ser Val His
                        580                 585                 590

Val Val Ala Val Met Leu Tyr Leu Leu Asp Arg Phe Ser Pro Phe Gly
                        595                 600                 605

Arg Phe Lys Val Asn Ser Glu Glu Glu Glu Asp Ala Leu Thr Leu
                        610                 615                 620

Ser Ser Ala Met Trp Phe Ser Trp Gly Val Leu Leu Asn Ser Gly Ile
        625                 630                 635                 640

Gly Glu Gly Ala Pro Arg Ser Phe Ser Ala Arg Ile Leu Gly Met Val
                        645                 650                 655

Trp Ala Gly Phe Ala Met Ile Ile Val Ala Ser Tyr Thr Ala Asn Leu
                        660                 665                 670

Ala Ala Phe Leu Val Leu Asp Arg Pro Glu Glu Arg Ile Thr Gly Ile
                        675                 680                 685

Asn Asp Pro Arg Leu Arg Asn Pro Ser Asp Lys Phe Ile Tyr Ala Thr
                        690                 695                 700

Val Lys Gln Ser Ser Val Asp Ile Tyr Phe Arg Arg Gln Val Glu Leu
        705                 710                 715                 720

Ser Thr Met Tyr Arg His Met Glu Lys His Asn Tyr Glu Ser Ala Ala
                        725                 730                 735

Glu Ala Ile Gln Ala Val Arg Asp Asn Lys Leu His Ala Phe Ile Trp
                        740                 745                 750

Asp Ser Ala Val Leu Glu Phe Glu Ala Ser Gln Lys Cys Asp Leu Val
                        755                 760                 765

Thr Thr Gly Glu Leu Phe Phe Arg Ser Gly Phe Gly Ile Gly Met Arg
        770                 775                 780

Lys Asp Ser Pro Trp Lys Gln Asn Val Ser Leu Ser Ile Leu Lys Ser
        785                 790                 795                 800

His Glu Asn Gly Phe Met Glu Asp Leu Asp Lys Thr Trp Val Arg Tyr
                        805                 810                 815

Gln Glu Cys Asp Ser Arg Ser Asn Ala Pro Ala Thr Leu Thr Phe Glu
                        820                 825                 830

Asn Met Ala Gly Val Phe Met Leu Val Ala Gly Gly Ile Val Ala Gly
                        835                 840                 845

Ile Phe Leu Ile Phe Ile Glu Ile Ala Tyr Lys Arg His Lys Asp Ala
                        850                 855                 860

Arg Arg Lys Gln Met Gln Leu Ala Phe Ala Ala Val Asn Val Trp Arg
        865                 870                 875                 880

Lys Asn Leu Gln Gln Tyr His Pro Thr Asp Ile Thr Gly Pro Leu Asn
                        885                 890                 895
```

```
Leu Ser Asp Pro Ser Val Ser Thr Val Val Lys Asn Leu Gln Ser Thr
            900                 905                 910
Gly Gly Gly Arg Gly Ala Leu Gln Asn Gln Lys Asp Thr Val Leu Pro
        915                 920                 925
Arg Arg Ala Ile Glu Arg Glu Glu Gly Gln Leu Gln Leu Cys Ser Arg
    930                 935                 940
His Arg Glu Ser
945

(2) INFORMATION FOR SEQ ID NO: 27:

(i) SEQUENCE CHARACTERISTICS:
        (A) LENGTH: 985 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 27:

Met Ser Thr Met Arg Leu Leu Thr Leu Ala Leu Leu Phe Ser Cys Ser
1               5                   10                  15
Val Ala Arg Ala Ala Cys Asp Pro Lys Ile Val Asn Ile Gly Ala Val
            20                  25                  30
Leu Ser Thr Arg Lys His Glu Gln Met Phe Arg Glu Ala Val Asn Gln
        35                  40                  45
Ala Asn Lys Arg His Gly Ser Trp Lys Ile Gln Leu Asn Ala Thr Ser
    50                  55                  60
Val Thr His Lys Pro Asn Ala Ile Gln Met Ala Leu Ser Val Cys Glu
65                  70                  75                  80
Asp Leu Ile Ser Ser Gln Val Tyr Ala Ile Leu Val Ser His Pro Pro
                85                  90                  95
Thr Pro Asn Asp His Phe Thr Pro Thr Pro Val Ser Tyr Thr Ala Gly
            100                 105                 110
Phe Tyr Arg Ile Pro Val Leu Gly Leu Thr Thr Arg Met Ser Ile Tyr
        115                 120                 125
Ser Asp Lys Ser Ile His Leu Ser Phe Leu Arg Thr Val Pro Pro Tyr
    130                 135                 140
Ser His Gln Ser Ser Val Trp Phe Glu Met Met Arg Val Tyr Ser Trp
145                 150                 155                 160
Asn His Ile Ile Leu Leu Val Ser Asp Asp His Glu Gly Arg Ala Ala
                165                 170                 175
Gln Lys Arg Leu Glu Thr Leu Leu Glu Glu Arg Glu Ser Lys Ser Lys
            180                 185                 190
Lys Arg Asn Tyr Glu Asn Leu Asp Gln Leu Ser Tyr Asp Asn Lys Arg
        195                 200                 205
Gly Pro Lys Ala Glu Lys Val Leu Gln Phe Asp Pro Gly Thr Lys Asn
    210                 215                 220
Val Thr Ala Leu Leu Met Glu Ala Lys Glu Leu Glu Ala Arg Val Ile
225                 230                 235                 240
Ile Leu Ser Ala Ser Glu Asp Asp Ala Ala Thr Val Tyr Arg Ala Ala
                245                 250                 255
Ala Met Leu Asn Met Thr Gly Ser Gly Tyr Val Trp Leu Val Gly Glu
            260                 265                 270
Arg Glu Ile Ser Gly Asn Ala Leu Arg Tyr Ala Pro Asp Gly Ile Leu
        275                 280                 285
```

-continued

```
Gly Leu Gln Leu Ile Asn Gly Lys Asn Glu Ser Ala His Ile Ser Asp
    290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
                340                 345                 350

Asp Gly Val Thr Gly Arg Val Glu Phe Asn Glu Asp Gly Asp Arg Lys
            355                 360                 365

Phe Ala Asn Tyr Ser Ile Met Asn Leu Gln Asn Arg Lys Leu Val Gln
    370                 375                 380

Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Glu Phe Thr Val Asn
        435                 440                 445

Gly Asp Pro Val Lys Lys Val Ile Cys Thr Gly Pro Asn Asp Thr Ser
    450                 455                 460

Pro Gly Ser Pro Arg His Thr Val Pro Gln Cys Cys Tyr Gly Phe Cys
465                 470                 475                 480

Ile Asp Leu Leu Ile Lys Leu Ala Arg Thr Met Asn Phe Thr Tyr Glu
                485                 490                 495

Val His Leu Val Ala Asp Gly Lys Phe Gly Thr Gln Glu Arg Val Asn
            500                 505                 510

Asn Ser Asn Lys Lys Glu Trp Asn Gly Met Met Gly Glu Leu Leu Ser
        515                 520                 525

Gly Gln Ala Asp Met Ile Val Ala Pro Leu Thr Ile Asn Asn Glu Arg
    530                 535                 540

Ala Gln Tyr Ile Glu Phe Ser Lys Pro Phe Lys Tyr Gln Gly Leu Thr
545                 550                 555                 560

Ile Leu Val Lys Lys Glu Ile Pro Arg Ser Thr Leu Asp Ser Phe Met
                565                 570                 575

Gln Pro Phe Gln Ser Thr Leu Trp Leu Leu Val Gly Leu Ser Val His
            580                 585                 590

Val Val Ala Val Met Leu Tyr Leu Leu Asp Arg Phe Ser Pro Phe Gly
        595                 600                 605

Arg Phe Lys Val Asn Ser Glu Glu Glu Glu Asp Ala Leu Thr Leu
    610                 615                 620

Ser Ser Ala Met Trp Phe Ser Trp Gly Val Leu Leu Asn Ser Gly Ile
625                 630                 635                 640

Gly Glu Gly Ala Pro Arg Ser Phe Ser Ala Arg Ile Leu Gly Met Val
                645                 650                 655

Trp Ala Gly Phe Ala Met Ile Ile Val Ala Ser Tyr Thr Ala Asn Leu
            660                 665                 670

Ala Ala Phe Leu Val Leu Asp Arg Pro Glu Glu Arg Ile Thr Gly Ile
        675                 680                 685

Asn Asp Pro Arg Leu Arg Asn Pro Ser Asp Lys Phe Ile Tyr Ala Thr
    690                 695                 700
```

-continued

```
Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
            740                 745                 750

Asp Ser Ala Val Leu Glu Phe Glu Ala Ser Gln Lys Cys Asp Leu Val
        755                 760                 765

Thr Thr Gly Glu Leu Phe Phe Arg Ser Gly Phe Gly Ile Gly Met Arg
    770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
                805                 810                 815

Gln Glu Cys Asp Ser Arg Ser Asn Ala Pro Ala Thr Leu Thr Phe Glu
            820                 825                 830

Asn Met Ala Gly Val Phe Met Leu Val Ala Gly Gly Ile Val Ala Gly
        835                 840                 845

Ile Phe Leu Ile Phe Ile Glu Ile Ala Tyr Lys Arg His Lys Asp Ala
    850                 855                 860

Arg Arg Lys Gln Met Gln Leu Ala Phe Ala Ala Val Asn Val Trp Arg
865                 870                 875                 880

Lys Asn Leu Gln Gln Tyr His Pro Thr Asp Ile Thr Gly Pro Leu Asn
                885                 890                 895

Leu Ser Asp Pro Ser Val Ser Thr Val Val Lys Asn Leu Gln Asp Arg
            900                 905                 910

Lys Ser Gly Arg Ala Glu Pro Asp Pro Lys Lys Lys Ala Thr Phe Arg
        915                 920                 925

Ala Ile Thr Ser Thr Leu Ala Ser Ser Phe Lys Arg Arg Arg Ser Ser
    930                 935                 940

Lys Asp Thr Ser Thr Gly Gly Gly Arg Gly Ala Leu Gln Asn Gln Lys
945                 950                 955                 960

Asp Thr Val Leu Pro Arg Arg Ala Ile Glu Arg Glu Glu Gly Gln Leu
                965                 970                 975

Gln Leu Cys Ser Arg His Arg Glu Ser
            980                 985

(2) INFORMATION FOR SEQ ID NO: 28:

(i) SEQUENCE CHARACTERISTICS:
        (A) LENGTH: 985 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 28:

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60
```

-continued

```
Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Ser Gly Tyr Val Trp Leu Val Gly Glu
            260                 265                 270

Arg Glu Ile Ser Gly Asn Ala Leu Arg Tyr Ala Pro Asp Gly Ile Leu
        275                 280                 285

Gly Leu Gln Leu Ile Asn Gly Lys Asn Glu Ser Ala His Ile Ser Asp
    290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
            340                 345                 350

Asp Gly Val Thr Gly Arg Val Glu Phe Asn Glu Asp Gly Asp Arg Lys
        355                 360                 365

Phe Ala Asn Tyr Ser Ile Met Asn Leu Gln Asn Arg Lys Leu Val Gln
    370                 375                 380

Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Glu Phe Thr Val Asn
        435                 440                 445

Gly Asp Pro Val Lys Lys Val Ile Cys Thr Gly Pro Asn Asp Thr Ser
    450                 455                 460

Pro Gly Ser Pro Arg His Thr Val Pro Gln Cys Cys Tyr Gly Phe Cys
465                 470                 475                 480

Ile Asp Leu Leu Ile Lys Leu Ala Arg Thr Met Asn Phe Thr Tyr Glu
```

```
                    485                 490                 495

Val His Leu Val Ala Asp Gly Lys Phe Gly Thr Gln Glu Arg Val Asn
                500                 505                 510

Asn Ser Asn Lys Lys Glu Trp Asn Gly Met Met Gly Glu Leu Leu Ser
            515                 520                 525

Gly Gln Ala Asp Met Ile Val Ala Pro Leu Thr Ile Asn Asn Glu Arg
        530                 535                 540

Ala Gln Tyr Ile Glu Phe Ser Lys Pro Phe Lys Tyr Gln Gly Leu Thr
545                 550                 555                 560

Ile Leu Val Lys Lys Glu Ile Pro Arg Ser Thr Leu Asp Ser Phe Met
                565                 570                 575

Gln Pro Phe Gln Ser Thr Leu Trp Leu Leu Val Gly Leu Ser Val His
            580                 585                 590

Val Val Ala Val Met Leu Tyr Leu Leu Asp Arg Phe Ser Pro Phe Gly
        595                 600                 605

Arg Phe Lys Val Asn Ser Glu Glu Glu Glu Asp Ala Leu Thr Leu
610                 615                 620

Ser Ser Ala Met Trp Phe Ser Trp Gly Val Leu Leu Asn Ser Gly Ile
625                 630                 635                 640

Gly Glu Gly Ala Pro Arg Ser Phe Ser Ala Arg Ile Leu Gly Met Val
            645                 650                 655

Trp Ala Gly Phe Ala Met Ile Ile Val Ala Ser Tyr Thr Ala Asn Leu
                660                 665                 670

Ala Ala Phe Leu Val Leu Asp Arg Pro Glu Glu Arg Ile Thr Gly Ile
            675                 680                 685

Asn Asp Pro Arg Leu Arg Asn Pro Ser Asp Lys Phe Ile Tyr Ala Thr
        690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
            740                 745                 750

Asp Ser Ala Val Leu Glu Phe Glu Ala Ser Gln Lys Cys Asp Leu Val
        755                 760                 765

Thr Thr Gly Glu Leu Phe Phe Arg Ser Gly Phe Gly Ile Gly Met Arg
770                 775                 780

Lys Asp Ser Pro Trp Lys Gln Asn Val Ser Leu Ser Ile Leu Lys Ser
                785                 790                 795                 800

His Glu Asn Gly Phe Met Glu Asp Leu Asp Lys Thr Trp Val Arg Tyr
            805                 810                 815

Gln Glu Cys Asp Ser Arg Ser Asn Ala Pro Ala Thr Leu Thr Phe Glu
        820                 825                 830

Asn Met Ala Gly Val Phe Met Leu Val Ala Gly Gly Ile Val Ala Gly
            835                 840                 845

Ile Phe Leu Ile Phe Ile Glu Ile Ala Tyr Lys Arg His Lys Asp Ala
        850                 855                 860

Arg Arg Lys Gln Met Gln Leu Ala Phe Ala Ala Val Asn Val Trp Arg
865                 870                 875                 880

Lys Asn Leu Gln Gln Tyr His Pro Thr Asp Ile Thr Gly Pro Leu Asn
                885                 890                 895

Leu Ser Asp Pro Ser Val Ser Thr Val Val Lys Asn Leu Gln Asp Arg
            900                 905                 910
```

```
Lys Ser Gly Arg Ala Glu Pro Asp Pro Lys Lys Lys Ala Thr Phe Arg
        915                 920                 925

Ala Ile Thr Ser Thr Leu Ala Ser Ser Phe Lys Arg Arg Arg Ser Ser
    930                 935                 940

Lys Asp Thr Ser Thr Gly Gly Arg Gly Ala Leu Gln Asn Gln Lys
945                 950                 955                 960

Asp Thr Val Leu Pro Arg Arg Ala Ile Glu Arg Glu Glu Gly Gln Leu
                965                 970                 975

Gln Leu Cys Ser Arg His Arg Glu Ser
            980                 985
```